(12) United States Patent
Dizerega

(10) Patent No.: US 11,497,726 B2
(45) Date of Patent: Nov. 15, 2022

(54) TOPICAL THERAPY FOR THE TREATMENT OF CERVICAL INTRAEPITHELIAL NEOPLASIA (CIN) AND CERVICAL CANCER USING NANOPARTICLES OF TAXANES

(71) Applicant: DFB SORIA, LLC, Fort Worth, TX (US)

(72) Inventor: Gere Dizerega, Fort Worth, TX (US)

(73) Assignee: DFB SORIA, LL., Fort Worth, TX (US)

( * ) Notice: Subject to any disclaimer, the term of this patent is extended or adjusted under 35 U.S.C. 154(b) by 0 days.

(21) Appl. No.: 16/978,820

(22) PCT Filed: Mar. 12, 2019

(86) PCT No.: PCT/US2019/021751
§ 371 (c)(1),
(2) Date: Sep. 8, 2020

(87) PCT Pub. No.: WO2019/178024
PCT Pub. Date: Sep. 19, 2019

(65) Prior Publication Data
US 2020/0405682 A1 Dec. 31, 2020

Related U.S. Application Data

(60) Provisional application No. 62/643,861, filed on Mar. 16, 2018.

(51) Int. Cl.
*A61K 31/337* (2006.01)
*A61P 35/00* (2006.01)
*A61K 9/51* (2006.01)
*A61K 47/06* (2006.01)

(52) U.S. Cl.
CPC .............. *A61K 31/337* (2013.01); *A61K 9/51* (2013.01); *A61K 47/06* (2013.01); *A61P 35/00* (2018.01)

(58) Field of Classification Search
CPC ........ A61K 31/337; A61K 9/51; A61K 47/06; A61P 35/00
See application file for complete search history.

(56) References Cited

U.S. PATENT DOCUMENTS

| | | | |
|---|---|---|---|
| 5,399,363 A | 3/1995 | Liversidge et al. | |
| 5,756,537 A | 5/1998 | Gill | |
| 5,833,891 A | 11/1998 | Subramaniam et al. | |
| 5,874,029 A | 2/1999 | Subramaniam et al. | |
| 5,886,026 A | 3/1999 | Hunter et al. | |
| 5,994,341 A | 11/1999 | Hunter et al. | |
| 6,004,573 A | 12/1999 | Rathi et al. | |
| 6,113,795 A | 9/2000 | Subramaniam et al. | |
| 6,117,949 A | 9/2000 | Rathi et al. | |
| 6,322,817 B1 | 11/2001 | Maitra et al. | |
| 6,365,191 B1 | 4/2002 | Burman et al. | |
| 6,406,722 B1 | 6/2002 | Gallaher | |
| 6,515,016 B2 | 2/2003 | Hunter | |
| 6,656,966 B2 | 12/2003 | Garvey et al. | |
| 6,689,803 B2 | 2/2004 | Hunter | |
| 6,749,868 B1 | 6/2004 | Desai et al. | |
| 6,892,091 B1 | 5/2005 | Ben-Haim et al. | |
| 7,217,735 B1 | 5/2007 | Au et al. | |
| 7,361,683 B2 | 4/2008 | Lee et al. | |
| RE40,493 E | 9/2008 | Straub et al. | |
| 7,744,923 B2 | 6/2010 | Rajewski et al. | |
| 7,807,369 B2 | 10/2010 | Van Der Burg et al. | |
| 7,820,788 B2 | 10/2010 | Desai et al. | |
| 7,879,360 B2 | 2/2011 | Cunningham et al. | |
| 7,901,698 B2 | 3/2011 | Zanutto et al. | |
| 8,034,765 B2 | 10/2011 | De et al. | |
| 8,039,494 B1 | 10/2011 | Winckle et al. | |
| 8,062,658 B2 | 11/2011 | Shalaby et al. | |
| 8,178,123 B2 | 5/2012 | Pauletti et al. | |
| 8,221,779 B2 | 7/2012 | Jonas et al. | |
| 8,293,277 B2 | 10/2012 | Swanson et al. | |
| 8,299,088 B2 | 10/2012 | Matteucci et al. | |
| 8,343,962 B2 | 1/2013 | Kisak et al. | |
| 8,486,924 B2 | 7/2013 | Ansell et al. | |
| 8,486,978 B2 | 7/2013 | Winckle et al. | |
| 8,778,181 B1 | 7/2014 | Johnson et al. | |
| 8,846,110 B2 | 9/2014 | Lee et al. | |
| 8,846,771 B2 | 9/2014 | Desai et al. | |
| 8,865,194 B1 | 10/2014 | Gans et al. | |
| 8,906,392 B2 | 12/2014 | Berkland et al. | |
| 9,018,146 B2 | 4/2015 | Wheeler et al. | |
| 9,056,137 B2 | 6/2015 | Hsu | |

(Continued)

FOREIGN PATENT DOCUMENTS

| CN | 101129338 | 2/2008 |
|---|---|---|
| CN | 100544714 | 9/2009 |

(Continued)

OTHER PUBLICATIONS

McGuire et all, Journal of Clinical Oncology 14, No. 3 (Mar. 1, 1996) 792-5. (Year: 1996).*
Alcaraz et al., "Cutaneous metastases from Internal Malignancies: A clinicopathologic and immunohistochemical Review," *Am. J. Dermatopathol*, 34:347-393, 2012.
Ali et al., "Inflammation of actinic keratosis during paclitaxel chemotherapy," *BMJ. Case Rep.*, 2015.
Alvarez-Roman et al., "Skin penetration and distribution of polymeric nanoparticles", *Journal of Controlled Release*, 99:53-62, 2004.
American College of Obstetricians and Gynecologists. "Management of vulvar intraepithelial neoplasia. Committee Opinion No. 675" *Obstet Gynecol.*, 128:178-182, 2016.
Baroli, "Penetration of Nanoparticles and Nanomaterials in the Skin: Fiction or Reality?" Journal of Pharmaceutical Sciences 2010 99(1):21-50 (Year: 2010).

(Continued)

*Primary Examiner* — Robert S Cabral
(74) *Attorney, Agent, or Firm* — Norton Rose Fulbright US LLP

(57) ABSTRACT

Disclosed are methods useful for the topical therapeutic treatment of cervical intraepithelial neoplasia (CIN) and/or cervical cancer using compositions containing nanoparticles of paclitaxel or other taxanes.

18 Claims, 2 Drawing Sheets

(56) References Cited

U.S. PATENT DOCUMENTS

| | | | |
|---|---|---|---|
| 9,149,440 | B2 | 10/2015 | Turos et al. |
| 9,149,455 | B2 | 10/2015 | Desai et al. |
| 9,278,069 | B2 | 3/2016 | Berkland et al. |
| 9,283,284 | B2 | 3/2016 | Renier et al. |
| 9,339,548 | B2 | 5/2016 | Hsu |
| 9,572,790 | B2 | 2/2017 | Ye et al. |
| 9,724,323 | B2 | 8/2017 | Desai et al. |
| 9,763,946 | B2 | 9/2017 | Lin |
| 9,814,685 | B2 | 11/2017 | Baltezor et al. |
| 10,555,898 | B2 | 2/2020 | Dizerega |
| 2001/0029264 | A1 | 10/2001 | McChesney |
| 2002/0013298 | A1 | 1/2002 | Hunter |
| 2004/0033267 | A1 | 2/2004 | Merisko-Liverside et al. |
| 2004/0220081 | A1 | 11/2004 | Kreitz et al. |
| 2005/0129736 | A1 | 6/2005 | Hunter et al. |
| 2005/0281750 | A1 | 12/2005 | Willcox et al. |
| 2006/0104999 | A1 | 5/2006 | Hesson et al. |
| 2006/0147383 | A1 | 7/2006 | Mallard et al. |
| 2006/0188566 | A1 | 8/2006 | Liversidge et al. |
| 2007/0041910 | A1 | 2/2007 | Pitre et al. |
| 2008/0063699 | A1 | 3/2008 | Teifel et al. |
| 2008/0160095 | A1 | 7/2008 | Desai et al. |
| 2008/0220075 | A1 | 9/2008 | Merisko-Liverside et al. |
| 2009/0042950 | A1 | 2/2009 | Pandya |
| 2009/0060870 | A1 | 3/2009 | Van der Burg et al. |
| 2009/0202654 | A1 | 8/2009 | Nixon |
| 2009/0291925 | A1 | 11/2009 | Shalaby |
| 2010/0204175 | A1 | 8/2010 | Renier et al. |
| 2011/0105596 | A1 | 5/2011 | Hosen |
| 2011/0212033 | A1 | 9/2011 | Tamarkin et al. |
| 2012/0134951 | A1 | 5/2012 | Stasko |
| 2012/0237768 | A1 | 9/2012 | Hirokawa et al. |
| 2012/0252897 | A1 | 10/2012 | Mehta et al. |
| 2013/0211384 | A1 | 8/2013 | Raspagliesi |
| 2013/0267490 | A1 | 10/2013 | Gupta et al. |
| 2014/0073615 | A1 | 3/2014 | Carlsson et al. |
| 2014/0199244 | A1 | 7/2014 | Rijcken et al. |
| 2014/0294967 | A1 | 10/2014 | Borbely et al. |
| 2014/0296140 | A1 | 10/2014 | Johnson et al. |
| 2015/0342872 | A1 | 12/2015 | Williamson et al. |
| 2016/0184331 | A1 | 6/2016 | Kanemitsu et al. |
| 2016/0213757 | A1 | 7/2016 | Edelson et al. |
| 2016/0354336 | A1 | 12/2016 | Baltezor et al. |
| 2016/0374953 | A1 | 12/2016 | Baltezor et al. |
| 2017/0333384 | A1 | 11/2017 | Desai et al. |
| 2018/0177739 | A1 | 6/2018 | Johnson et al. |
| 2019/0022081 | A1 | 1/2019 | Baltezor et al. |

FOREIGN PATENT DOCUMENTS

| | | |
|---|---|---|
| CN | 101829061 | 9/2010 |
| CN | 101843582 | 9/2010 |
| CN | 102686205 | 9/2012 |
| CN | 105280869 | 1/2016 |
| GB | 2474930 | 5/2011 |
| JP | 2001503785 | 3/2001 |
| JP | 2010529025 | 8/2010 |
| JP | 2010533163 | 10/2010 |
| JP | 2011508774 | 3/2011 |
| WO | WO 95/03036 | 2/1995 |
| WO | WO 1998/024427 | 6/1998 |
| WO | WO 2000/072827 | 12/2000 |
| WO | WO 2003/032906 | 4/2003 |
| WO | WO 2004/009075 | 1/2004 |
| WO | WO 2006/133271 | 12/2006 |
| WO | WO 2008/150532 | 12/2008 |
| WO | WO 2009/007764 | 1/2009 |
| WO | WO 2009/085314 | 7/2009 |
| WO | WO 2011/039638 | 4/2011 |
| WO | WO 2011/151418 | 12/2011 |
| WO | WO 2012/130314 | 10/2012 |
| WO | WO 2014/091729 | 6/2014 |
| WO | WO 2014/210485 | 12/2014 |
| WO | WO 2016/071365 | 5/2016 |
| WO | WO 2016/197091 | 12/2016 |
| WO | WO 2017/049083 | 3/2017 |

OTHER PUBLICATIONS

Barua et al., "Challenges associated with penetration of nanoparticles across cell and tissue barriers: A review of current status and future prospects." Nano Today, 9: 223-243, 2014.

Batheja et al., "Topical drug delivery by a polymeric nanosphere gel: Formulation optimization and in vitro and in vivo skin distribution studies." J Control Release, 149(2):159-67, 2011.

Bharadwaj et al., "Topical delivery of paclitaxel for treatment of skin cancer", Drug Development And Industrial Pharmacy, 6 (9): 1482-1494, 2016.

Boehncke et al., "Leukocyte extravasation as a target for anti-inflammatory therapy—Which molecule to choose?", Experimental Dermatology, 14:70-80, 2005.

Bos et al., "The 500 Dalton rule for the skin penetration of chemical compounds and drugs." Exp Dermatol,9: 165-169, 2000.

Bubna et al., "Imiquimod—Its role in the treatment of cutaneous malignancies" Indian J. Pharmacol., 47(4):354-359, 2015.

Cabula et al., "Electrochemotherapy in the treatment of cutaneous metastases from Breast Cancer: A multicenter Cohort Analysis," Ann. Surg. Oncol.,22:S442-S450, 2015.

Campaña-Seoane et al., "Bioadhesive emulsions for control release of progesterone resistant to vaginal fluids clearance" International Journal of Pharmaceutics, 477:495-505, 2014.

Chambers et al., "Eruptive purpuric papules on the arms; a case of chemotherapy-induced inflammation of actinic keratosis and review of the literature," Dermatology Online Journal,20(1), 2014.

De Giorgi et al., "Cutaneous manifestations of breast carcinoma," Dermatol Therapy,23:581-589, 2010.

De Smet et al. "Development of a Nanocrystalline Paclitaxel Formulation for Hipec Treatment." Pharmaceutical Research, 29: 2398-2406, 2012.

De Witte et al., "Imiquimod in cervical, vaginal and vulvar intraepithelial neoplasia: A review" Gynecol Oncol.,139:377-384, 2015.

Deng et al. "Understanding the Structure and Stability of Paclitaxel Nanocrystals." Int J Pharm,390(2): 242-249, 2010.

Desai et al. "Interaction of nanoparticles and cell-penetrating peptides with skin for transdermal drug delivery." Mol Membr Biol., 27:247-259, 2010.

Dodds et al., "Actinic Keratosis: Rationale and Management" Dermatol Ther (Heidelb),4:11-31, 2014.

Doge et al., "Identification of polystyrene nanoparticle penetration across intact skin barrier as rare event at sites of focal particle aggregations" Journal of Photonics, 11(e201700169):1-10, 2018.

Ehrlich et al., "Micellar paclitaxel improves severe psoriasis in a prospective phase II pilot study", Journal of the American Academy of Dermatology, 50: 533-540, 2004.

Elstad et al. "OncoGel (ReGel/paclitaxel)—clinical applications for a novel paclitaxel delivery system." Advanced Drug Delivery Reviews, 61: 785-794, 2009.

Feng et al. "A critical review of lipid-based nanoparticles for taxane delivery." Cancer Letters, 334:157-175, 2013.

Fernandez-Anton Martinez et al., "Metastasis cutaneas de origen visceral," Actas Dermosifiliogr.,104(10):841-853, 2013.

Forbes et al. "Non-aqueous silicone elastomer gels as a vaginal microbicide delivery system for the HIV-1 entry inhibitor maraviroc." Journal of Controlled Release,156:161-169, 2011.

Garrido et al., "Cutaneous metastates of lung cancer," Clin. Transl. Oncol., 8(5):330-333, 2006.

Ghosh et al. "Effect of Physicochemical parameters on skin permeability of antihypertensive" Indian Journal of Experimental Biology 39:710-714, 2001.

Ghosh et al. "Nanosuspension for improving the bioavailability of a poorly soluble drug and screening of stabilizing agents to inhibit crystal growth." International Journal of Pharmaceutics, 409:260-268, 2011.

Gu et al., "Nanoformulation of paclitaxel to enhance cancer therapy." J Biomater Appl, 28(2):298-307, 2013.

(56) References Cited

OTHER PUBLICATIONS

Gupta et al., "Possible role of nanocarriers in drug delivery against cervical cancer" *Nano Reviews & Experiments,*8:1-25, 2017.
Halverstam et al., "Nonstandard and off-label therapies for psoriasis." *Clin Dermatol,* 26(5):546-53, 2008.
Hasegawa et al., "The problems of cervical conization for postmenopausal patients" *European Journal of Gynaecological Oncology,* 37(3):327-331, 2016.
Heidenreich et al., "Angiogenesis drives psoriasis pathogenesis", *Int. J. Exp. Path.,* vol. 90: 232-248, 2009.
Henseler et al., "Disease concomitance in psoriasis", *Journal of the American Academy of Dermatology,* 32: 982-986, 1995.
Hosmer et al., "Influence of internal structure and composition of liquid crystalline phases on topical delivery of paclitaxel." *J Pharm Sci,* 100(4):1444-1455, 2010.
Ilyas et al., "Inflammatory Actinic Keratoses Secondary to Systemic Chemotherapy," *Cutis.,*75:167-168, 2005.
Insinga et al., "Epidemiologic natural history and clinical management of human papillomavirus (HPV) disease: *A critical and systematic review of the literature in the development of an HPV dynamic transmission model"* BMC Infectious Disease, 9:119, 2009.
International Preliminary Report on Patentability for PCT/US2016/052133, dated Feb. 1, 2018.
International Search Report & Written Opinion issued in International Patent Application No. PCT/US2016/052133, dated Mar. 24, 2017.
International Search Report and Written Opinion issued in International Patent Application No. PCT/US2018/022540, dated Jun. 18, 2018.
International Search Report and Written Opinion issued in International Patent Application No. PCT/US2018/022553, dated Jun. 18, 2018.
International Search Report and Written Opinion issued in International Patent Application No. PCT/US2018/022557, dated Jun. 18, 2018.
International Search Report and Written Opinion issued in International Patent Application No. PCT/US19/21751, dated Jun. 3, 2019.
Karande et al., "Discovery of transdermal penetration enhancers by high-throughput screening." *Nature Biotechnology* 22 (2), 192-197, 2004.
Khandavilli et al., "Nanoemulsions as versatile formulations for paclitaxel delivery: peroral and dermal delivery studies in rats." *J Invest Dermatol,* 127(1):154-62, 2007.
Kilfoyle et al., "Development of paclitaxel-TyroSpheres for topical skin treatment", *Journal Of Controlled Release,*163(1),18-24, 2012.
Koeneman et al., "TOPical Imiquimod treatment of high-grade Cervical intraepithelial neoplasia (TOPIC trial): study protocol for a randomized controlled trial" *BMC Cancer,* 16:132, 2016.
Lee et al., "Micellar nanoparticles: applications for topical and passive transdermal drug delivery." *Handbook of non-invasive drug delivery,* 2: 37-58, 2010.
Likes et al., "Pilot study of sexual function and quality of life after excision of vulvar intraepithelial neoplasia," *J. Reprod. Med.,* 52(1):23-27, 2007.
Liu et al., "Enabling anticancer therapeutics by nanoparticle carriers: the delivery of Paclitaxel." *Int J Mol Sci,* 12(7):4395-413, 2011.
Lookingbill et al., "Cutaneous metastases in patients with metastatic carcinoma: A retrospective study of 4020 patients" *J. Am. Acad. Dermatol.,* 29:228-236, 1993.
Ma et al., "Paclitaxel Nano-Delivery Systems: A Comprehensive Review", *Journal of Nanomedicine and Nonotechnology,* 4(2):1-35, 2013.
Major et al., "Vaginal drug delivery of the localized treatment of cervical cancer" *Drug Delivery and Translational Research,*7:817-828, 2017.
Mak et al., "Progress in understanding the immunopathogenesis of psoriasis", *Aetas Dermosifiliogr,*100: 2-13, 2009.
Merisko-Liversidge et al., "Formulation and Antitumor Activity Evaluation of Nanocrystalline Suspensions of Poorly Soluble Anticancer Drugs". Pharmaceutical Research,13:(2):272-278, 1996.
Merisko-Liversidge et al., "Nanosizing: a formulation approach for poorly-water-soluble compounds." *European Journal of Pharmaceutical Sciences,* 18:113-120, 2003.
Muller et al. "Challenges and solutions for the delivery of biotech drugs—a review of drug nanocrystal technology and lipid nanoparticles." *Journal of Biotechnology,* 113:151-170, 2004.
Munoz et al., "A phase II trial of the use of 4,4'-dihydroxybenzophenome-2-4-dinitrophenyl-hydrazone (A-007) topical gel in the treatment of high-grade squamous intraepithelial lesions (HSIL) of the cervix" Journal of Clinical Oncology, 2007 ASCO Annual Meeting Proceeds, 25(18S):5593 (Abstract Only).
Narang et al., "Pharmaceutical development and regulatory considerations for nanoparticles and nanoparticulate drug delivery systems." *J Pharm Sci.,* 102(11):3867-82, 2013.
Nickoloff et al., "Recent insights into the immunopathogenesis of psoriasis provide new therapeutic opportunities", The Journal of Clinical Investigation, vol. 113, No. 12, 2004, pp. 1164-1675.
Notice of Reasons for Rejection from the Japanese Patent Office issued in corresponding Patent Application No. 2018-515121 dated Jul. 30, 2020.
Ojima et al., "Taxane anticancer agents: a patient perspective" *Expert Opin. Ther. Patents,*26(1), 20 pages, 2016.
Okabe et al., "Percutaneous absorption enhancing effect and skin irritation of monocyclic monoterpenes" *Drug Des. Deliv.,*6(3):229-238, 1990.
Osborne et al, "Skin Penetration Enhancers Cited in the Technical Literature." *Pharmaceutical Technology November,* 58-66, 1997.
Panchagnula et al., "Effect of lipid bilayer alteration on transdermal delivery of a high-molecular-weight and lipophilic drug: studies with paclitaxel." *J Pharm Sci,* 93(9):2177-83, 2004.
Parisi et al., "Global Epidemiology of Psoriasis: A Systematic Review of Incidence and Prevalence", *Journal of Investigative Dermatology,*133: 377-385, 2013.
Patlolla et al., "Translocation of cell penetrating peptide engrafted nanoparticles across skin layers" *Biomaterials,* 31:5598-5607, 2010.
Pepe et al., "Protein transduction domain-containing microemulsions as cutaneous delivery systems for an anticancer agent." J *Pharm Sci,* 102(5):1476-87, 2013.
Pepe et al., "Transportan in nanocarriers improves skin localization and antitumor activity of paclitaxel" *International Journal of Nanomedicine,*11:2009-2019. 2016.
Petry., "Management options for cervical intraepithelial neoplasia" *Best Pract. Res. Clin. Obstet. Gynaecol.,*25(5):641-651, 2011.
Prow et al.,"Nanoparticles and microparticles for skin drug delivery." Adv Drug Deliv Rev, 63(6):470-91, 2011.
Ranade et al., "Clinical and economic implications of the use of nanoparticle paclitaxel (Nanoxel) in India." Ann Oncol, 24:v6-v12, 2013.
Rancan et al. "Skin Penetration and Cellular Uptake of Amorphous Silica Nanoparticles with Variable Size, Surface Functionalization, and Colloidal Stability" ACS Nano 2012 6(8):6829-6842, 2012.
Reyes et al., "An update on vulvar intraepithelial neoplasia: terminology and practical approach to diagnosis" J. Clin. Pathol., 67:290-294, 2014.
Roberts, "Targeted drug delivery to the skin and deeper tissues: role of physiology, solute structure and disease." Clin Exp Pharmacol Physiol, 24(11):874-9, 1997.
Rowinsky et al., "Clinical toxicities encountered with paclitaxel (Taxol)", Seminars In Oncology, pp. 1-15, 1993.
Santesso et al., "Systematic reviews and meta-analyses of benefits and harms of cryotherapy, LEEP and cold knife conization to treat cervical intraepithelial neoplasia," *Int. J. Gynecol. Obstet.,* 132:266-271, 2016.
Search Report and Written Opinion issued in Corresponding Singapore Patent Application No. 11201801822T, dated Jul. 1, 2019.
Search Report and Written Opinion issued in Singapore Patent Application No. 11201801822T, dated Jul. 1, 2019.
Second Written Opinion for PCT/US2016/052133, dated Oct. 27, 2017.

(56) References Cited

OTHER PUBLICATIONS

Sheihet et al. "Tyrosine-derived nanospheres for enhanced topical skin penetration." *Int J Pharm*, 350:312-319, 2008.
Spratt et al., "Efficacy of Skin-Directed Therapy for Cutaneous Metastaes from Advanced Cancer: A Meta-Analysis," *J. Clin. Oncol.*,32:3144-3155, 2014.
Sun et al. "Application of Nano- and Micro-Particles on the Topical Therapy of Skin-Related Immune Disorders." *Current Pharmaceutical Design*, 21:2643-2667, 2015.
Surapaneni et al. "Designing Paclitaxel Drug Delivery Systems Aimed at Improved Patient Outcomes: Current Status and Challenges." *ISRN Pharmacol.*, 2012:623139, 2012.
Utreja et al., "Localized delivery of paclitaxel using elastic liposomes: Formulation development and evaluation" *Drug Delivery*, 18(5):367-376, 2011.
Van Eerdenbrugh et al., "Top-down production of drug, nanocrystals: Nanosuspension stabilization, miniaturization and transformation into solid products", *International Journal Of Pharmaceutics*, 364(1): 64-75, 2008.
Van Seters et al., "Treatment of vulvar Intraepithelial Neoplasia with Topical Imiquimod" *The New England Journal of Medicine*, 358(14):1465-1473, 2008.
Varma et al. "Enhanced oral paclitaxel absorption with vitamin E-TPGS: effect on solubility and permeability in vitro, in situ and in vivo.." European Journal of Pharmaceutical Sciences, 445-453, 2005.
Vaz Tostav et al., "Paclitaxel-loaded lipid nanoparticles for topical application: the influence of oil content on lipid dynamic behavior, stability, and drug skin penetration" *J. Nanopart. Res.*, 16:2782, 2014.
Watkinson et al., "Nanoparticles Do Not Penetrate Human Skin—A Theoretical Perspective" *Pharmaceutical Research*,30:1943-1946, 2013.
Williamson et al., "A Phase I study of Intraperitoneal nanoparticulate paclitaxel (Nanotax®) in patients with peritoneal malignancies" *Cancer Chemotherapy and Pharmacology*,15 pages, 2015.
Wong et al., "The Presentation, Pathology, and Current Management Strategies of Cutaneous Metastasis" *North American Journal of Medical Science*,5(9):499-504, 2013.
Worley et al., "Docetaxel Accumulates in Lymphatic Circulation Following Subcutaneous Delivery Compared to Intravenous Delivery in Rats" *Anticancer Research*, 36:5071-5078, 2016.
Wu et al., "Physical and chemical stability of drug nanoparticles." *Advanced Drug Delivery Reviews*, 63:456-469, 2011.
Yang et al., "Vaginal Delivery of Paclitaxel via Nanoparticles with Non-mucoadhesive Surfaces Suppresses Cervical Tumor Growth." *Adv. Healthcare Mater.*,3: 1044-1052, 2014.
Zentner et al., "Biodegradable block copolymers for delivery of proteins and water-insoluble drugs." *Journal of Controlled Release*, 72: 203-215, 2001.
Extended European Search Report issued in Corresponding European Application No. 19768522.5, dated Sep. 28, 2021.
Xu et al., "Impact of Surface Polyethylene Glycol (PEG) Density on Biodegradable Nanoparticle Transport in Mucus ex Vivo and Distribution in Vivo" *ACS Nano* 2015, 9(9), 9217-9227.
First Office Action from the China National Intellectual Property Administration issued in corresponding Patent No. 201680065699.7 dated Dec. 31, 2020.
Search Report from the China National Intellectual Property Administration issued in Patent Application No. 2016800656997 dated Dec. 24, 2020.
Konno et al., "Enhanced solubility of paclitaxel using water-soluble and biocompatible 2-methacryloyloxyethyl phosphorylcholine polymers" *Journal of Biomedical Materials Research* 2003, 65A: 209-214.
Lansdown, Alan B.G. "Silver in Medical Devices: Technology and Antimicrobial Efficacy." *Silver in Healthcare: Its Antimicrobial Efficacy and Safety in Use,* Issues in Toxicology No. 6 Royal Society of Chemistry Cambridge, 2010, p. 92 and 110.
Notice of Reasons for Rejection issued in Corresponding Japanese Application 2021-044501, dated Mar. 14, 2022 (English Translation provided).
Office Action issued in corresponding Japanese Application No. 2019550634, dated Jul. 7, 2022.

* cited by examiner

TOPICAL THERAPY FOR THE TREATMENT OF CERVICAL INTRAEPITHELIAL NEOPLASIA (CIN) AND CERVICAL CANCER USING NANOPARTICLES OF TAXANES

CROSS-REFERENCE TO RELATED APPLICATION

This application is a national phase application under 35 U.S.C. § 371 of International Application No. PCT/US2019/021751, filed Mar. 12, 2019, which claims the benefit of U.S. Provisional Application No. 62/643,861, filed Mar. 16, 2018. The contents of each of the referenced applications are incorporated in the present application by reference.

FIELD OF THE INVENTION

The present invention generally relates to the field of topical therapeutic treatment of cervical intraepithelial neoplasia (CIN) and cervical cancer. In particular, the invention relates to the use of topical compositions comprising taxane nanoparticles for treatment of CIN and cervical cancer.

BACKGROUND OF THE INVENTION

Cervical intraepithelial neoplasia (CIN), also known as cervical dysplasia, is a premalignant (precancerous) condition characterized by abnormal cells/cell growths (lesions) on the surface of the cervix (cervical epithelium) including the ectocervix, the squamocolumnar junction of the cervix, and/or the endocervix. The Human Papillomavirus (HPV) is usually the cause for CIN. CIN lesions can be detected by cytologic diagnosis (e.g., Pap smear), colposcopy, and/or histological assessment of a cervical biopsy. After initial detection with a cytologic diagnosis such as an abnormal Pap smear, further diagnosis and grading of CIN is accomplished with colposcopy and/or histological assessment of a cervical biopsy. CIN is generally classified into three histological classifications: CIN 1, CIN 2, and CIN 3. CIN 1 is considered low-grade CIN. CIN 2 and CIN 3 are considered high-grade CIN. An additional histological classification is CIN 2/3, which is a combination of CIN 2 and CIN 3 and has features of both CIN 2 and CIN 3. CIN 2/3 is considered high-grade CIN. The criteria for the histological classification of CIN is as follows:

CIN 1: Mild dysplasia or mild dyskaryosis. Good maturation of cells through the depth of the cervical epithelium, with minimal nuclear abnormalities and few mitotic figures. Undifferentiated cells are confined to the deeper/lower third of the epithelium. Mitotic figures are not very numerous. Cytopathic changes due to HPV infection may be observed in the full thickness of the epithelium.

CIN 2: Moderate dysplasia or moderate dyskaryosis. Dysplastic changes mostly restricted to the lower half or two-thirds of the epithelium, with more marked nuclear abnormalities than CIN 1. Mitotic figures are seen through the lower half of the epithelium.

CIN 3: Severe dysplasia or severe dyskaryosis. Differentiation and stratification may be totally absent or present only in the superficial quarter of the epithelium with numerous mitotic figures. Nuclear abnormalities extend throughout the thickness of the epithelium. Many mitotic figures have abnormal forms.

The histological classifications of CIN corresponds to two cytologic classifications as follows: CIN 1 corresponds to low-grade squamous intraepithelial lesions (LSIL); and CIN 2 and CIN 3, as well as CIN 2/3, correspond to high-grade squamous intraepithelial lesions (HSIL).

Left untreated, CIN can progress to invasive cervical cancer. The vast majority of low-grade CIN (CIN 1) resolves in less than two years without medical intervention; approximately 20% of CIN 2 will progress to CIN 3; and 4-5% of CIN 3 will progress to invasive cancer (Petry, Management options for cervical intraepithelial neoplasia. Best Pract Res Clin Obstet Gynaecol. 2011 October; 25(5):641-51; and Insinga et. al., Epidemiologic natural history and clinical management of human papillomavirus (HPV) disease: A critical and systematic review of the literature in the development of an HPV dynamic transmission model. BMC Infectious Disease. 2009; 9:119).

Given the association between CIN and cervical cancer, and the potential for metastases and death from cervical cancer, most women with high-grade CIN (CIN 2 and/or CIN 3) and in some cases, persistent low-grade CIN (CIN 1), receive treatment. High-grade CIN is most frequently treated with either cryotherapy, loop electrosurgical excision procedure (LEEP), or cold knife conization (CKC) (Santesso et. al., Systematic reviews and meta-analyses of benefits and harms of cryotherapy, LEEP, and cold knife conization to treat cervical intraepithelial neoplasia. Int J Gynecol Obstet. 2016; 132:266-271). These treatments have a high cure rate for CIN; however, they are associated with immediate adverse events such as bleeding or pain, as well as long-term concerns such as infertility, miscarriage and premature delivery (Santesso et al., 2016; and de Witte et. al., Imiquimod in cervical, vaginal and vulvar intraepithelial neoplasia: A review. Gynecol Oncol. 2015; 139:377-384). Imiquimod topically applied to the extocervix has demonstrated some efficacy in the treatment of high-grade CIN and was generally well-tolerated despite frequent adverse effects such as vaginal discharge, vulvar pain, fever, headache, and fatigue. Also, imiquimod can cause local irritation and reactions to skin and other epithelial tissues. US publication 2013/0211384 discloses methods for local delivery of TAXOL to the cervix for the treatment of CIN using a multicomponent implantable medical device having a drug delivery portion which comes into contact with the cervix. However, the implantable device must remain in the cervix for lengthy periods and would create discomfort. Topical formulations are disclosed in U.S. Pat. No. 9,056,137 for the treatment of CIN. The formulations are designed to be solid at room-temperature that melt into flowable compositions in response to physiological temperatures. For instance, a solid rod-shaped formulation was inserted into a cervical canal of a mouse in the examples, which then transformed into a gel-like formulation in situ. The solid-phase formulations in the '137 Patent can include a chemotherapeutic agent, propylene glycol, the penetration enhancer laurocapram (AZONE), and poloxamers. The compositions are designed for transdermal and transmucosal delivery of the chemotherapeutic agent. Local irritation could occur with laurocapram as edema and erythema have been observed with laurocapram in a Draize rabbit skin test model (Okabe et. al., Percutaneous absorption enhancing effect and skin irritation of monocyclic monoterpenes, Drug Des Deliv, 1990 September; 6(3)229-38). Thus, there is a significant unmet need for an effective treatment of CIN without pain and low to negligible local irritation or reactions.

Most cervical cancers are squamous cell carcinomas or adenocarcinomas, however, less common types of cervical cancer include melanoma, sarcoma, and lymphoma. Cervical cancer is staged using the TNM system. Once the TNM scores have been determined, the overall cervical cancer stage is assigned as follows: stage I (stage 1 cervical cancer): stage IA1, IA2, IB1, IB2; stage II (stage 2 cervical cancer): stage IIA, IIB; stage III (stage 3 cervical cancer): stage IIIA, IIIB; stage IV (stage 4 cervical cancer): stage IVA, IVB. Current cervical cancer treatments include surgery (cryosurgery, laser surgery, conization, hysterectomy, trachelectomy, pelvic exenteration), radiation therapy, immunotherapy, IV chemotherapy, and targeted therapy with bevacizumab. Surgical and radiation treatments can have undesirable side effects such as pain and bleeding. Side effects of immunotherapy, IV chemotherapy and targeted therapy can be systemic toxicities such as nausea, vomiting, loss of appetite, hair loss, mouth sores, and fatigue.

Delivery of therapeutic drugs into lesions of the skin and other epithelial tissues can be a challenge due to the barrier properties of the stratum corneum of the skin as well as a thickened epithelium and fibrous growths in lesions of epithelial tissue. The delivery of poorly water soluble drugs into these tissues can be even more of a challenge. Skin penetration enhancers, such as laurocapram (AZONE), diethylene glycol monoethyl ether (DGME or TRANSCUTOL), and isopropyl myristate, have been employed in topical drug formulations to increase the penetration of drugs into the skin and vaginal/cervical epithelial tissues have had some success. However, some penetration enhancers such as solvents and surfactants can be irritating to the skin and vaginal/cervical epithelium. Volatile silicone fluids have been employed in topical formulations to increase the penetration of drugs into the skin; however, high concentrations of volatile silicone fluids, i.e., 25% and greater, and/or combinations of volatile silicone fluids with other potential skin irritating compounds such as alcohols, e.g., $C_1$ to $C_4$ aliphatic alcohols, surfactants, other penetration enhancers, and other volatile solvents have been needed to produce the penetration enhancement effect. Additionally, some penetration enhancers will cause the drug to penetrate transdermally or transport through other epithelial tissues and be systemically absorbed, which is not desirable when only treating a condition of the skin or other epithelial tissues, such as lesions. Other topical delivery systems have been employed where the drug is chemically modified with surfactants, polymers, and other substances, but these materials can also be irritating to the skin and vaginal/cervical epithelial tissues.

Taxanes, including paclitaxel and docetaxel, have been used for the treatment of cancer for many years. These compounds are typically characterized as being poorly water soluble. The cancer treatment formulation initially developed for intravenous (IV) infusion injection, TAXOL® (BMS), is paclitaxel dissolved in a 50:50 v/v mixture of polyethoxylated castor oil (CREMOPHOR® EL) and dehydrated ethanol. However, the systemic use of this formulation results in significant clinical toxicity (Rowinsky et al. 1993). Substantial effort has been devoted to the development of CREMOPHOR EL-free formulations of paclitaxel for systemic use (Ma and Mumper, 2013). One such formulation is disclosed in U.S. Pat. No. 8,221,779, herein incorporated by reference, which discloses injectable aqueous compositions of antimitotic drug microparticles, including paclitaxel, useful for the treatment of cancers by intraperitoneal and intravenous (IV) injection of the compositions. Currently, there are no FDA approved topical taxane formulations for the treatment of CIN or cervical cancer in the U.S.

SUMMARY OF THE INVENTION

The present invention provides solutions to the aforementioned limitations and deficiencies in the art relating to the treatment of cervical intraepithelial neoplasia (CIN) and/or cervical cancer. Disclosed is a topical therapy that utilizes a topical composition with enhanced penetration for the delivery of taxane nanoparticles to the CIN and/or cervical cancer providing effective treatment with low to negligible local irritation. In certain instances, the treatment methods of the present invention can be used without the need to combine them with other known therapies such as those discussed above.

In one aspect of the invention, disclosed is a method of treating cervical intraepithelial neoplasia (CIN) and/or cervical cancer in a subject in need of treatment, the method comprising topically administering (topically applying) to an affected area of the subject a composition comprising a plurality of taxane nanoparticles, thereby treating the CIN and/or cervical cancer. The "affected area" of CIN or cervical cancer includes the area of the cervical epithelium including the ectocervix, squamocolumnar junction, and/or endocervix where one or more CIN lesions or cervical cancer tumors are detectable by cytologic diagnosis (e.g., Pap smear), colposcopy, and/or histological assessment of a cervical biopsy. The affected area can include areas of the cervical epithelium in the proximity of the one or more lesions or tumors likely to contain undetectable preclinical lesions. In some embodiments, the taxane nanoparticles are suspended within the composition. In other embodiments, the taxane nanoparticles have a mean particle size (number) from 0.1 microns to 1.5 microns, or from 0.1 microns to less than 1 micron. In various embodiments, the taxane nanoparticles are paclitaxel nanoparticles, docetaxel nanoparticles, or cabazitaxel nanoparticles, or any combination of such nanoparticles. In some embodiments, the taxane nanoparticles are paclitaxel nanoparticles. In some embodiments, the paclitaxel nanoparticles have a specific surface area (SSA) of at least 18 $m^2/g$, or from 18 $m^2/g$ to 40 $m^2/g$. The concentration of the taxane nanoparticles in the compositions is at a concentration effective to provide a therapeutic improvement (treatment) in the CIN and/or cervical cancer. In some embodiments, the effective concentration of the taxane nanoparticles or paclitaxel nanoparticles is about 0.15 to about 5% w/w. In some embodiments, the composition is anhydrous. In some embodiments, the composition is a hydrophobic composition and can comprise a hydrophobic carrier. In still other embodiments, the hydrophobic carrier is non-volatile and/or is non-polar. In various embodiments, the hydrophobic carrier comprises a hydrocarbon which can be petrolatum, mineral oil, or paraffin wax, or mixtures thereof. In some embodiments, the mineral oil is heavy mineral oil. In some embodiments, the hydrophobic carrier is greater than 50% w/w of the composition. The hydrophobic composition can further comprise one or more volatile silicone fluids. In some embodiments, the volatile silicone fluid is at a concentration of 5 to 24% w/w of the composition and can be cyclomethicone. In some embodiments, the cyclomethicone is cyclopentasiloxane. In various embodiments, the composition is a semi-solid composition and can be an ointment. In various embodiments, the composition does not contain volatile $C_1$-$C_4$ aliphatic alcohols or $C_1$-$C_5$ aliphatic alcohols, and/or does not contain additional penetration enhancers, and/or does not contain laurocapram, and/or does not contain diethylene glycol monoethyl ether, and/or does not contain isopropyl myristate, and/or does not contain alpha tocopherol, and/or does not contain additional volatile solvents, and/or does not contain surfactants, and/or does not contain a protein or albumin, and/or does not contain hyaluronic acid, and/or does not contain a conjugate of hyaluronic acid and a taxane, and/or does not contain a conjugate of hyaluronic acid and paclitaxel, and/or does not contain a polymer or copolymer.

In some embodiments, the CIN is CIN 1. In some embodiments, the CIN is CIN 2. In some embodiments, the CIN is CIN 3. In some embodiments, the CIN is CIN 2/3. In some embodiments, the CIN is CIN 2, CIN 3, or CIN 2/3. In some embodiments, the cervical cancer is squamous cell carcinoma or adenocarcinoma. In some embodiments, the cervical cancer is stage I, II, III, or IV cervical cancer.

In some embodiments, the method further comprises placing a cervical cap over the cervix after administration of the composition to the affected area. In other embodiments, the method does not include placing a cervical cap over the cervix after administration of the composition to the affected area.

In another aspect of the invention, there is disclosed a method of enhancing penetration of taxane nanoparticles into a CIN or cervical cancer of a subject, the method comprising topically applying to the affected area a hydrophobic composition comprising a continuous hydrophobic carrier, one or more volatile silicone fluids, and a plurality of taxane nanoparticles. In some embodiments, the taxane nanoparticles are suspended within the composition. In other embodiments, the taxane nanoparticles have a mean particle size (number) from 0.1 microns to 1.5 microns, or from 0.1 microns to less than 1 micron. In various embodiments, the taxane nanoparticles are paclitaxel nanoparticles, docetaxel nanoparticles, or cabazitaxel nanoparticles, or any combinations of such nanoparticles. In some embodiments, the taxane nanoparticles are paclitaxel nanoparticles. In some embodiments, the paclitaxel nanoparticles have a specific surface area (SSA) of at least 18 $m^2/g$, or from 18 $m^2/g$ to 40 $m^2/g$. In some embodiments, the concentration of the taxane nanoparticles or paclitaxel nanoparticles is about 0.15 to about 2% w/w. In some embodiments, the composition is anhydrous. In some embodiments, the composition is a hydrophobic composition and can comprise a hydrophobic carrier. In still other embodiments, the hydrophobic carrier is non-volatile and/or is non-polar. In various embodiments, the hydrophobic carrier comprises a hydrocarbon which can be petrolatum, mineral oil, or paraffin wax, or mixtures thereof. In some embodiments, the mineral oil is heavy mineral oil. In some embodiments, the hydrophobic carrier is greater than 50% w/w of the composition. The hydrophobic composition can further comprise one or more volatile silicone fluids. In some embodiments, the volatile silicone fluid is at a concentration of 5 to 24% w/w of the composition and can be cyclomethicone. In some embodiments, the cyclomethicone is cyclopentasiloxane. In various embodiments, the composition can be flowable or spreadable when being applied to the affected area. In some aspects, the composition can be a semi-solid composition and/or can be an ointment and can have a viscosity of 25,000 cps to 500,000 cps as measured with a Brookfield RV viscometer on a helipath stand with the helipath on, with a T-E spindle at 10 RPM at room temperature for 45 seconds. In various embodiments, the composition does not contain volatile $C_1$-$C_4$ aliphatic alcohols or $C_1$-$C_5$ aliphatic alcohols, and/or does not contain additional penetration enhancers, and/or does not contain laurocapram, and/or does not contain diethylene glycol monoethyl ether, and/or does not contain isopropyl myristate, and/or does not contain alpha tocopherol, and/or does not contain additional volatile solvents, and/or does not contain surfactants, and/or does not contain a protein or albumin, and/or does not contain hyaluronic acid, and/or does not contain a conjugate of hyaluronic acid and a taxane, and/or does not contain a conjugate of hyaluronic acid and paclitaxel, and/or does not contain a polymer or copolymer.

In some embodiments, the CIN is CIN 1. In some embodiments, the CIN is CIN 2. In some embodiments, the CIN is CIN 3. In some embodiments, the CIN is CIN 2/3. In some embodiments, the CIN is CIN 2, CIN 3, or CIN 2/3. In some embodiments, the cervical cancer is squamous cell carcinoma or adenocarcinoma. In some embodiments, the cervical cancer is stage I, II, III, or IV cervical cancer.

In some embodiments, the method further comprises placing a cervical cap over the cervix after application of the hydrophobic composition to the affected area. In other embodiments, the method does not include placing a cervical cap over the cervix after administration of the composition to the affected area. In some embodiments, the penetration of the taxane nanoparticles from the hydrophobic composition into the CIN or cervical cancer is greater than the penetration of taxane nanoparticles into the CIN or cervical cancer from topically applying a hydrophobic composition that comprises a plurality of taxane nanoparticles and that does not contain one or more volatile silicone fluids.

In another aspect of the inventions, disclosed is a method of enhancing penetration of taxane nanoparticles into a CIN or cervical cancer of a subject, the method comprising topically applying a hydrophobic composition comprising a plurality of taxane nanoparticles to the affected area, wherein the penetration of the taxane nanoparticles from the hydrophobic composition into the CIN or cervical cancer is greater than the penetration of taxane nanoparticles into the CIN or cervical cancer from topically applying an aqueous based composition comprising a plurality of taxane nanoparticles. In some embodiments, the taxane nanoparticles have a mean particle size (number) from 0.1 microns to 1.5 microns, or from 0.1 microns to less than 1 micron. In some embodiments, taxane nanoparticles are paclitaxel nanoparticles, docetaxel nanoparticles, or cabazitaxel nanoparticles, or any combination of such nanoparticles. In some embodiments, hydrophobic composition further comprises a hydrophobic carrier. In some embodiments, the CIN is CIN 1. In some embodiments, the CIN is CIN 2. In some embodiments, the CIN is CIN 3. In some embodiments, the CIN is CIN 2/3. In some embodiments, the CIN is CIN 2, CIN 3, or CIN 2/3. In some embodiments, the cervical cancer is squamous cell carcinoma or adenocarcinoma. In some embodiments, the cervical cancer is stage I, II, III, or IV cervical cancer.

As disclosed in international application PCT/US16/52133 herein incorporated by reference, it was found that hydrophobic compositions of the present invention having a volatile silicone fluid at concentrations less than 25% w/w in combination with an anhydrous hydrophobic carrier exhibited greater skin penetration (i.e., penetration into the epidermal and dermal portions of the skin) of taxane nanoparticles as compared to the skin penetration of taxane nanoparticles from the hydrophobic carrier alone. Surprisingly, it was also discovered that, other than the low amounts of volatile silicone fluid (less than 25 w/w %), the addition of other skin penetration enhancers to the hydrophobic compositions had little or no effect on the skin penetration of the compositions. Therefore, the compositions of the present invention can be free of (do not have to include) these additional skin penetration enhancers (e.g., surfactants, volatile solvents, alcohols, $C_1$-$C_4$ aliphatic alcohols or $C_1$-$C_5$ aliphatic alcohols), which can be helpful in reducing skin or local irritation when the compositions of the present invention are applied to the skin or vaginal/cervical epithelial tissues. Even more surprising is that the enhanced penetration was accomplished with low concentrations of cyclomethicone, i.e., less than 25% w/w. Additionally, the taxane nanoparticles are not transdermally delivered or are not transported through vaginal/cervical epithelial tissue with these compositions initially after administration, which is a favorable feature because transdermal delivery or delivery through epithelial tissue (systemic absorption) is not desired when treating the skin (epidermis and dermis) or other epithelial tissues. Furthermore, the skin penetration (i.e., penetration into the dermal or epidermal portions of the skin) of taxane nanoparticles from the compositions of the present invention was far superior to the skin penetration of taxane nanoparticles from aqueous based compositions, even though the aqueous based compositions contained a skin penetration enhancer. Additionally, it was found that the taxane nanoparticles were stable and did not exhibit crystal grow over time in the hydrophobic compositions of the present invention.

Hydrophobic compositions which comprise nanoparticles of a taxane, e.g., paclitaxel, and a volatile silicone fluid in combination with a hydrophobic carrier, are especially suitable for the topical treatment of CIN and/or cervical cancer because of the aforementioned enhanced penetration properties of these compositions. The hydrophobic carrier can be the continuous phase of the composition with the nanoparticles suspended therein.

Also, disclosed in the context of the present invention are the following embodiments 1 to 80:

Embodiment 1 is a method of treating cervical intraepithelial neoplasia (CIN) or cervical cancer in a subject in need of treatment, the method comprising topically administering to an affected area of the subject a composition comprising a plurality of taxane nanoparticles, thereby treating the CIN and/or cervical cancer.

Embodiment 2 is the method of embodiment 1, wherein the taxane nanoparticles are suspended within the composition.

Embodiment 3 is the method of any one of embodiments 1 to 2, wherein the taxane nanoparticles have a mean particle size (number) from 0.1 microns to 1.5 microns.

Embodiment 4 is the method of embodiment 3, wherein the taxane nanoparticles have a mean particle size (number) from 0.1 microns to less than 1 micron.

Embodiment 5 is the method of any one of embodiments 1 to 4, wherein the taxane nanoparticles are paclitaxel nanoparticles, docetaxel nanoparticles, or cabazitaxel nanoparticles.

Embodiment 6 is the method of embodiment 5, wherein the taxane nanoparticles are paclitaxel nanoparticles.

Embodiment 7 is the method of embodiment 6, wherein the paclitaxel nanoparticles have a specific surface area (SSA) of at least 18 $m^2/g$.

Embodiment 8 is the method of embodiment 7, wherein the paclitaxel nanoparticles have a specific surface area (SSA) of 18 $m^2/g$ to 40 $m^2/g$.

Embodiment 9 is the method of any of embodiments 1 to 8, wherein the concentration of the taxane nanoparticles is at a concentration effective to provide a therapeutic improvement of the CIN or cervical cancer.

Embodiment 10 is the method of embodiment 9, wherein the concentration of the paclitaxel nanoparticles is about 0.15 to about 2% w/w.

Embodiment 11 is the method of any one of embodiments 1 to 10, wherein the composition is anhydrous.

Embodiment 12 is the method of any one of embodiments 1 to 11, wherein the composition is a hydrophobic composition.

Embodiment 13 is the method of embodiment 12, wherein the hydrophobic composition comprises a hydrophobic carrier.

Embodiment 14 is the method of embodiment 13, wherein the hydrophobic carrier is non-volatile.

Embodiment 15 is the method of any one of embodiments 13 to 14, wherein the hydrophobic carrier is non-polar.

Embodiment 16 is the method of any one of embodiments 13 to 15, wherein the hydrophobic carrier comprises a hydrocarbon.

Embodiment 17 is the method of embodiment 16, wherein the hydrocarbon is petrolatum, mineral oil, or paraffin wax, or mixtures thereof.

Embodiment 18 is the method of embodiment 17, wherein the mineral oil is heavy mineral oil.

Embodiment 19 is the method of any one of embodiments 13 to 18, wherein the hydrophobic carrier is greater than 50% w/w of the composition.

Embodiment 20 is the method of any one of embodiments 13 to 19, wherein the hydrophobic composition comprises one or more volatile silicone fluids.

Embodiment 21 is the method of embodiment 20, wherein the concentration of the one or more volatile silicone fluids is from 5 to 24% w/w of the composition.

Embodiment 22 is the method of embodiment 21, wherein the volatile silicone fluid is cyclomethicone.

Embodiment 23 is the method of embodiment 22, wherein the cyclomethicone is cyclopentasiloxane.

Embodiment 24 is the method of any one of embodiments 1 to 23, wherein the composition is a semi-solid composition.

Embodiment 25 is the method of embodiment 24, wherein the semi-solid composition is an ointment.

Embodiment 26 is the method of any one of embodiments 1 to 25, wherein the composition does not contain volatile $C_1$-$C_4$ aliphatic alcohols.

Embodiment 27 is the method of any one of embodiments 1 to 26, wherein the composition does not contain additional penetration enhancers.

Embodiment 28 is the method of any one of embodiments 1 to 27, wherein the composition does not contain additional volatile solvents.

Embodiment 29 is the method of any one of embodiments 1 to 28, wherein the composition does not contain surfactants.

Embodiment 30 is the method of any one of embodiments 1 to 29, wherein the composition does not contain a protein or albumin.

Embodiment 31 is the method of any one of embodiments 1 to 30, wherein the composition does not contain a polymer or copolymer.

Embodiment 32 is the method of any one of embodiments 1 to 31, wherein the subject has CIN, and wherein the CIN is treated.

Embodiment 33 is the method of embodiment 32, wherein the CIN is CIN 1.

Embodiment 34 is the method of embodiment 32, wherein the CIN is CIN 2, CIN 3, or CIN 2/3.

Embodiment 35 is the method of any one of embodiments 1 to 34, wherein the subject has cervical cancer, and wherein the cervical cancer is treated.

Embodiment 36 is the method of any one of embodiments 1 to 35, wherein the method further comprises placing a cervical cap over the cervix after administration of the composition to the affected area.

Embodiment 37 is a method of enhancing penetration of taxane nanoparticles into a cervical intraepithelial neoplasia (CIN) or cervical cancer of a subject, the method comprising topically applying to the affected area a hydrophobic composition comprising a continuous hydrophobic carrier, one or more volatile silicone fluids, and a plurality of taxane nanoparticles.

Embodiment 38 is the method of embodiment 37, wherein the taxane nanoparticles are suspended within the hydrophobic composition.

Embodiment 39 is the method of any one of embodiments 37 to 38, wherein the taxane nanoparticles have a mean particle size (number) from 0.1 microns to 1.5 microns.

Embodiment 40 is the method of embodiment 39, wherein the taxane nanoparticles have a mean particle size (number) from 0.1 microns to less than 1 micron.

Embodiment 41 is the method of any one of embodiments 37 to 40, wherein the taxane nanoparticles are paclitaxel nanoparticles, docetaxel nanoparticles, or cabazitaxel nanoparticles.

Embodiment 42 is the method of embodiment 41, wherein the taxane nanoparticles are paclitaxel nanoparticles.

Embodiment 43 is the method of embodiment 42, wherein the paclitaxel nanoparticles have a specific surface area (SSA) of at least 18 $m^2/g$.

Embodiment 44 is the method of embodiment 43, wherein the paclitaxel nanoparticles have a specific surface area (SSA) of 18 $m^2/g$ to 40 $m^2/g$.

Embodiment 45 is the method of any one of embodiments 42 to 44, wherein the concentration of the paclitaxel nanoparticles is about 0.15 to about 2% w/w.

Embodiment 46 is the method of any one of embodiments 37 to 45, wherein the composition is anhydrous.

Embodiment 47 is the method of any one of embodiments 37 to 46, wherein the hydrophobic carrier is non-volatile.

Embodiment 48 is the method of any one of embodiments 37 to 47, wherein the hydrophobic carrier is non-polar.

Embodiment 49 is the method of any one of embodiments 37 to 48, wherein the hydrophobic carrier comprises a hydrocarbon.

Embodiment 50 is the method of embodiment 49, wherein the hydrocarbon is petrolatum, mineral oil, or paraffin wax, or mixtures thereof.

Embodiment 51 is the method of embodiment 50, wherein the mineral oil is heavy mineral oil.

Embodiment 52 is the method of any one of embodiments 37 to 51, wherein the hydrophobic carrier is greater than 50% w/w of the composition.

Embodiment 53 is the method of any one of embodiments 37 to 52, wherein the concentration of the one or more volatile silicone fluids is from 5 to 24% w/w of the composition.

Embodiment 54 is the method of embodiment 53, wherein the volatile silicone fluid is cyclomethicone.

Embodiment 55 is the method of embodiment 54, wherein the cyclomethicone is cyclopentasiloxane.

Embodiment 56 is the method of any one of embodiments 37 to 55, wherein the composition is a semi-solid composition.

Embodiment 57 is the method of embodiment 56, wherein the semi-solid composition is an ointment.

Embodiment 58 is the method of any one of embodiments 56 to 57, wherein the viscosity of the composition is 25,000 cps to 500,000 cps as measured with a Brookfield RV viscometer on a helipath stand with the helipath on, with a T-E spindle at 10 RPM at room temperature for 45 seconds.

Embodiment 59 is the method of any one of embodiments 37 to 58, wherein the composition does not contain volatile $C_1$-$C_4$ aliphatic alcohols.

Embodiment 60 is the method of any one of embodiments 37 to 59, wherein the composition does not contain additional penetration enhancers.

Embodiment 61 is the method of any one of embodiments 37 to 60, wherein the composition does not contain additional volatile solvents.

Embodiment 62 is the method of any one of embodiments 37 to 61, wherein the composition does not contain surfactants.

Embodiment 63 is the method of any one of embodiments 37 to 62, wherein the composition does not contain a protein or albumin.

Embodiment 64 is the method of any one of embodiments 37 to 62, wherein the composition does not contain a polymer or copolymer.

Embodiment 65 is the method of any one of embodiments 37 to 64, wherein the subject has CIN.

Embodiment 66 is the method of embodiment 65, wherein the CIN is CIN 1.

Embodiment 67 is the method of embodiment 65, wherein the CIN is CIN 2, CIN 3, or CIN 2/3.

Embodiment 68 is the method of any one of embodiments 37 to 67, wherein the subject has cervical cancer.

Embodiment 69 is the method of any one of embodiments 37 to 68, wherein the method further comprises placing a cervical cap over the cervix after application of the hydrophobic composition to the affected area.

Embodiment 70 is the method of any one of embodiments 37 to 69, wherein the penetration of the taxane nanoparticles from the hydrophobic composition into the CIN or cervical cancer is greater than the penetration of taxane nanoparticles into the CIN or cervical cancer from topically applying a hydrophobic composition that comprises a plurality of taxane nanoparticles and that does not contain one or more volatile silicone fluids.

Embodiment 71 is a method of enhancing penetration of taxane nanoparticles into a cervical intraepithelial neoplasia (CIN) or cervical cancer of a subject, the method comprising topically applying a hydrophobic composition comprising a plurality of taxane nanoparticles to the affected area, wherein the penetration of the taxane nanoparticles from the hydrophobic composition into the CIN or cervical cancer is greater than the penetration of taxane nanoparticles into the CIN or cervical cancer from topically applying an aqueous based composition comprising a plurality of taxane nanoparticles.

Embodiment 72 is the method of embodiment 71, wherein the taxane nanoparticles have a mean particle size (number) from 0.1 microns to 1.5 microns.

Embodiment 73 is the method of embodiment 72, wherein the taxane nanoparticles have a mean particle size (number) from 0.1 microns to less than 1 micron.

Embodiment 74 is the method of any one of embodiments 71 to 73, wherein the taxane nanoparticles are paclitaxel nanoparticles, docetaxel nanoparticles, or cabazitaxel nanoparticles.

Embodiment 75 is the method of any one of embodiments 71 to 74, wherein the hydrophobic composition further comprises a hydrophobic carrier.

Embodiment 76 is the method of any one of embodiments 71 to 75, wherein the subject has CIN.

Embodiment 77 is the method of embodiment 76, wherein the CIN is CIN 1.

Embodiment 78 is the method of embodiment 76, wherein the CIN is CIN 2, CIN 3, or CIN 2/3.

Embodiment 79 is the method of any one of embodiments 71 to 78, wherein the subject has cervical cancer.

Embodiment 80 is the method of any one of embodiments 71 to 79, wherein the hydrophobic composition comprises a continuous hydrophobic phase having the plurality of taxane nanoparticles suspended therein.

The terms "nanoparticle", "nanoparticles", and "nanoparticulate", as used herein with regard to taxane particles, represent the mean particle size (based on the number-weighted differential distribution, designated as "number") of the taxane particles which is from 0.01 microns to 1.5 microns (10 nm to 1500 nm) or preferably from 0.1 microns to 1.5 microns (100 nm to 1500 nm), or more preferably from 0.1 microns to less than 1 micron (100 nm to less than 1000 nm).

The term "water soluble," as used herein, describes compounds that have a solubility in water of greater than 10 mg/mL or greater at room temperature.

The term "poorly water soluble," as used herein, describes compounds that have a solubility in water of less than or equal to 10 mg/mL at room temperature.

The term "hydrophobic," as used herein, describes compounds, compositions, or carriers that have a solubility in water of less than or equal to 10 mg/mL at room temperature.

The term "volatile," as used herein, describes compounds, compositions, or carriers that have a vapor pressure greater than or equal to 10 Pa at room temperature.

The term "non-volatile," as used herein, describes compounds, compositions, or carriers that have a vapor pressure less than 10 Pa at room temperature.

The term "anhydrous," as used herein with regard to the compositions or carriers of the invention, means that less than 3% w/w, preferably less than 2% w/w, more preferably less than 1% w/w, or most preferably 0% w/w of water is present in the compositions or carriers. This can account for small amounts of water being present (e.g., water inherently contained in any of the ingredients of the compositions or carriers, water contracted from the atmosphere, etc.).

The terms "skin" or "cutaneous" as used herein mean the epidermis and/or the dermis.

The term "affected area" of cervical intraepithelial neoplasia (CIN) or cervical cancer includes the area of the cervical epithelium including the ectocervix, squamocolumnar junction, and/or endocervix where one or more CIN lesions or cervical cancer tumors are detectable by cytologic diagnosis (e.g., Pap smear), colposcopy, and/or histological assessment of a cervical biopsy. The affected area can include areas of the cervical epithelium in the proximity of the one or more lesions or tumors likely to contain undetectable preclinical lesions.

The terms "subject" or "patient" as used herein mean a vertebrate animal. In some embodiments, the vertebrate animal can be a mammal. In some embodiments, the mammal can be a primate, including a human.

The term "room temperature" (RT) as used herein, means 20-25° C.

The term "penetration enhancer" or "skin penetration enhancer" as used herein, means a compound or a material or a substance that facilitates drug absorption into the skin (epidermis and dermis).

The term "surfactant" or "surface active agent" as used herein, means a compound or a material or a substance that exhibits the ability to lower the surface tension of water or to reduce the interfacial tension between two immiscible substances.

Unless otherwise specified, the percent values expressed herein are weight by weight and are in relation to the weight of the total composition.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

For this application, a number value with one or more decimal places can be rounded to the nearest whole number using standard rounding guidelines, i.e. round up if the number being rounded is 5, 6, 7, 8, or 9; and round down if the number being rounded is 0, 1, 2, 3, or 4. For example, 3.7 can be rounded to 4.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The use of the word "a" or "an" when used in conjunction with the terms "comprising," "having," "including," or "containing" (or any variations of these words) may mean "one," but it is also consistent with the meaning of "one or more," "at least one," and "one or more than one."

The compositions and methods for their use can "comprise," "consist essentially of," or "consist of" any of the ingredients or steps disclosed throughout the specification. With respect to the phrase "consisting essentially of," a basic and novel property of the compositions of the present invention are their ability to topically treat CIN and/or cervical cancer. With respect to hydrophobic compositions of the present invention, a basic and novel property includes the ability to treat CIN or cervical cancer and the ability to penetrate into cervical epithelial tissues with limited to no penetration through the epithelial tissues into the bloodstream. This can be achieved without the use of $C_1$-$C_4$ aliphatic alcohols or $C_1$-$C_5$ aliphatic alcohols, surfactants, and additional skin penetration enhancers and additional volatile solvents other than a volatile silicone fluid(s) (e.g., cyclomethicone or cyclopentasiloxane, or a combination thereof).

"Limited," "reduced," or "minimal" when modifying the phrase "penetration transdermally" means wherein less than 0.01 μg/cm$^2$ of the drug nanoparticles penetrate through human cadaver skin when the composition is applied to the human cadaver skin as determined by an in vitro Franz diffusion cell system.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
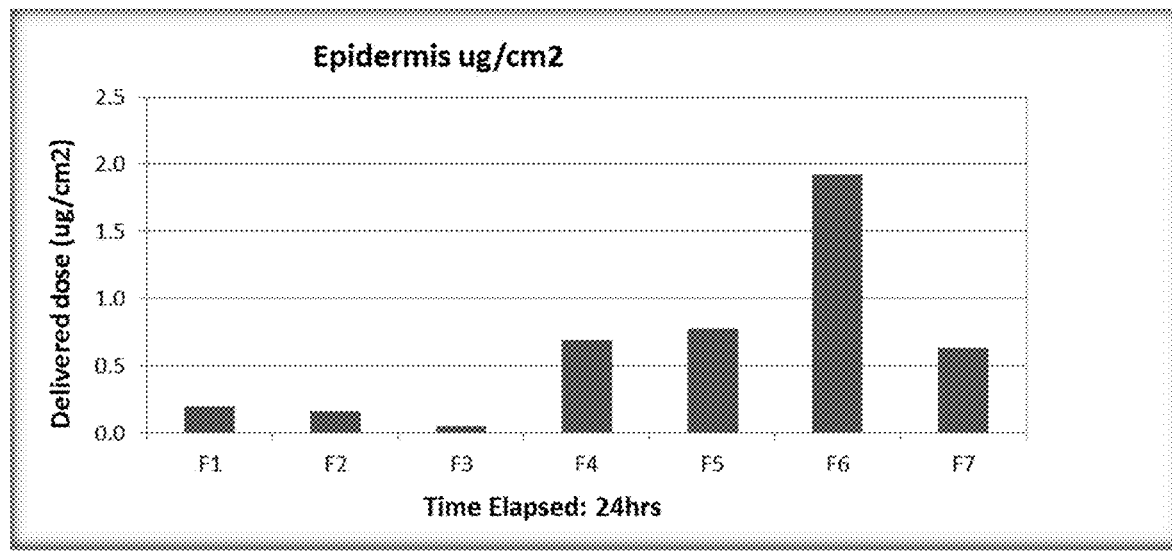
FIG. 1 graphically shows the concentration of paclitaxel (μg/cm2) delivered in vitro into the epidermis for formulas F1 through F7.

In some aspects, the invention relates to methods of treatment of cervical intraepithelial neoplasia (CIN) and/or cervical cancer in a patient by topically applying to the affected area (topical therapy) a composition comprising a taxane(s), thereby treating the CIN and/or cervical cancer. In some embodiments, the taxane is paclitaxel. In other embodiments, the taxane is docetaxel or cabazitaxel. In further embodiments, a combination of taxanes can be used (e.g., paclitaxel and docetaxel, or paclitaxel and cabazitaxel, or docetaxel and cabazitaxel, or paclitaxel, docetaxel, and cabazitaxel). In some embodiments, the composition comprises a carrier. In some embodiments, the carrier is anhydrous and/or hydrophobic. In other aspects, the carrier is aqueous based. In some embodiments, the taxane(s) is a plurality of nanoparticles of the taxane(s). In other embodiments, the taxane(s) is solubilized. Suitable compositions for use in the methods of the invention are disclosed in international patent application number PCT/US16/52133, herein incorporated by reference. In a preferred embodiment, the composition is a hydrophobic composition comprising a continuous hydrophobic carrier, one or more volatile silicone fluids, and a plurality of taxane nanoparticles, wherein the taxane nanoparticles are suspended within the composition and wherein the mean particle size (number) of the taxane nanoparticles is from 0.1 microns to 1.5 microns or from 0.1 microns to less than 1 micron. In some embodiments, the concentration of the one or more volatile silicone fluids is 5 to 24% w/w. In some embodiments, the composition does not contain volatile $C_1$-$C_4$ aliphatic alcohols or $C_1$-$C_5$ aliphatic alcohols. In some embodiments, the concentration of the taxane nanoparticles is at a concentration effective to provide a therapeutic improvement (treatment) in the CIN and/or cervical cancer. In some embodiments, the concentration of the taxane nanoparticles is at a concentration of 0.1 to 5% w/w, about 0.1 to about 2% w/w or about 0.15 to about 2% w/w.

Cervical intraepithelial neoplasia (CIN) includes all histological classifications/gradings of CIN including, but not limited to low-grade CIN (CIN 1) and high grade CIN (CIN 2, CIN 3, and/or CIN 2/3); as well as all cytological classifications of CIN including low-grade squamous intraepithelial lesions (LSIL), and high-grade squamous intraepithelial lesions (HSIL). Cervical cancer includes all types of cervical cancer including, but not limited to squamous cell carcinomas, adenocarcinomas, melanoma, sarcoma, and lymphoma; and all stages of cervical cancer including, but not limited to stage I (stage 1 cervical cancer): stage IA1, IA2, IB1, IB2; stage II (stage 2 cervical cancer): stage IIA, IIB; stage III (stage 3 cervical cancer): stage IIIA, IIIB; stage IV (stage 4 cervical cancer): stage IVA, IVB.

I. Compositions

In one aspect of the invention, the compositions of the present invention are hydrophobic and comprise a continuous hydrophobic carrier, one or more volatile silicone fluids (such as cyclomethicone), and a plurality of taxane nanoparticles. The compositions can be flowable or spreadable when being applied to an affected area. The compositions can be suspensions of a plurality of the taxane nanoparticles within a mixture of the hydrophobic carrier and the volatile silicone fluid. The taxane nanoparticles can be completely dispersed, or partially dispersed and partially dissolved in the compositions. In various embodiments, the taxane nanoparticles are not completely dissolved in the compositions. The hydrophobic compositions can be anhydrous. A hydrophobic composition is a composition in which the total amount of the hydrophobic constituents in the composition is greater than the total amount of the non-hydrophobic constituents in the composition. The hydrophobic carrier can be the continuous phase of the hydrophobic compositions. Therefore, the compositions of the present invention can include at least two phases, a continuous hydrophobic carrier phase and a suspended taxane nanoparticle phase. The volatile silicone fluid can be solubilized and/or dispersed within the continuous phase.

Surprisingly, the hydrophobic compositions of the invention that include volatile silicone fluids at low concentrations, i.e., less than 25% w/w, in combination with a continuous, anhydrous hydrophobic carrier, exhibited greater skin penetration (i.e., penetration into the epidermal and/or dermal portions of the skin) of taxane nanoparticles as compared to the skin penetration of taxane nanoparticles from the hydrophobic carrier alone. In fact, and even more surprising, the addition of other skin penetration enhancers had little or no effect on the skin penetration of these compositions. Notably, however, the taxane nanoparticles did not penetrate through the skin (i.e., transdermal penetration) or only a negligible amount penetrated transdermally through the skin, i.e. less than 0.01 μg/cm². Furthermore, the skin penetration (i.e., epidermal or dermal penetration) of taxane nanoparticles from the anhydrous hydrophobic compositions was far superior to the skin penetration of taxane nanoparticles from aqueous based compositions even though the aqueous based compositions contained a skin penetration enhancer. Additionally, and also surprisingly, the hydrophobic compositions of the invention that include less than 25% of a volatile silicone fluid in combination with a hydrophobic carrier, do not need to contain alcohols, additional volatile solvents, additional penetration enhancers, polymers/copolymers or surfactants to provide enhanced skin penetration, thereby allowing for a most cost-efficient and simplified composition that can have reduced irritancy when topically applied. If desired, however, such components can be included in the compositions of the present invention. In some embodiments, the hydrophobic compositions are free of/do not include or contain additional penetration enhancers. In some embodiments, the hydrophobic compositions are free of/do not include or contain laurocapram. In some embodiments, the hydrophobic compositions are free of/do not include diethylene glycol monoethyl ether (DGME). In some embodiments, the hydrophobic compositions are free of/do not include isopropyl myristate. In other embodiments, the hydrophobic compositions are free of/do not include alpha tocopherol. In other embodiments, the hydrophobic compositions are free of/do not include or contain additional volatile solvents or compounds. In some embodiments, the hydrophobic compositions are free of/do not include or contain any alcohols or $C_1$-$C_4$ aliphatic alcohols. In some embodiments, the hydrophobic compositions are free of/do not include or contain alcohol or $C_1$-$C_5$ aliphatic alcohols. In other embodiments, the hydrophobic compositions are free of/do not include or contain surfactants. In other embodiments, the hydrophobic compositions are free of/do not include polymers/copolymers (or biodegradable polymers/copolymers). In other embodiments, the hydrophobic compositions are free of/do not include poloxamers, styrene-isobutylene-styrene (SIBS), a polyanhydride copolymer, polycaprolactone, polyethylene glycol, Poly (bis(P-carboxyphenoxy)propane-sebacic acid, and/or poly(D, L lactic-co-glycolic acid (PLGA). In various embodiments, the volatile silicone fluid is a cyclomethicone. In other embodiments, the cyclomethicone is cyclopentasiloxane. In some embodiments, the hydrophobic compositions comprise one or more volatile silicone fluids, but do not contain additional silicone materials. In some embodiments, the hydrophobic compositions are semi-solid compositions. In other embodiments the hydrophobic compositions are ointments. In some embodiments, the hydrophobic compositions are not sprays and are not sprayable.

In some embodiments, the hydrophobic compositions are semi-solid compositions, including ointments, and have a viscosity of from 12,500 cps to 247,500 cps, or from 25,000 cps to 150,000 cps as measured at room temperature by a Brookfield RV viscometer using a small sample adapter with a SC4-14 spindle and a 6R chamber at 5 rpm with an equilibration time of 2 minutes. An alternative method for performing viscosity measurements of the hydrophobic, semi-solid compositions is using a Brookfield RV viscometer on a helipath stand with the helipath on, with a T-E spindle at 10 RPM at room temperature for 45 seconds. In some embodiments, the hydrophobic compositions are semi-solid compositions, including ointments, and have a viscosity of from 25,000 cps to 500,000 cps, or from 25,000 cps to 400,000 cps, or from 25,000 cps to 350,000 cps, or from 25,000 cps to 300,000 cps, or from 50,000 cps to 500,000 cps, or from 50,000 cps to 400,000 cps, or from 50,000 cps to 350,000 cps, or from 50,000 cps to 300,000 cps, or from 75,000 cps to 500,000 cps, or from 75,000 cps to 400,000 cps, or from 75,000 cps to 350,000 cps, or from 75,000 cps to 300,000 cps, or from 100,000 cps to 500,000 cps, or from 100,000 cps to 400,000 cps, or from 100,000 cps to 350,000 cps, or from 100,000 cps to 300,000 cps using a Brookfield RV viscometer on a helipath stand with the helipath on, with a T-E spindle at 10 RPM at room temperature for 45 seconds.

In another aspect, the invention relates to compositions that inhibit crystal growth of taxane nanoparticles in carriers. In some embodiments, inhibition of crystal growth of taxane nanoparticles in carriers is accomplished by inclusion of the nanoparticles in a hydrophobic carrier. In some embodiments, the hydrophobic carriers comprise a hydrocarbon. In some embodiments, the hydrophobic carriers comprise petrolatum, mineral oil, and/or paraffin. In some embodiments, the mineral oil is heavy mineral oil. In other embodiments, the hydrophobic carriers further comprise one or more volatile silicone fluids. In still other embodiments, the volatile silicone fluid is cyclomethicone. In other embodiments, the cyclomethicone is cyclopentasiloxane. In other embodiments, inhibition of crystal growth of taxane nanoparticles in aqueous carriers is accomplished by inclusion of the nanoparticles in an aqueous carrier comprising poloxamer 407, a quaternary ammonium compound, or a cross-linked acrylic acid polymer, or mixtures thereof.

The compositions of the present invention can be formulated in various forms suitable for pharmaceutical and topical delivery. Non-limiting examples include semi-solid compositions, lotions, liquid suspensions, emulsions, creams, gels, ointments, pastes, aerosol sprays, aerosol foams, non-aerosol sprays, non-aerosol foams, films, and sheets. Semi-solid compositions include ointments, pastes, and creams. For purposes of this invention, semi-solid compositions are not sprayable. The compositions can be impregnated in gauzes, bandages, or other skin dressing materials. In some embodiments, the compositions are semi-solid compositions. In some embodiments, the compositions are ointments. In other embodiments, the compositions are gels. In still other embodiments, the compositions are liquid suspensions. In some embodiments, the compositions are not sprays and are not sprayable. In some embodiments, the compositions are not dry powders. In some embodiments, the compositions do not solely include the taxane nanoparticles.

The compositions of the present invention can be packaged in any package configuration suitable for topical products. Non-limiting examples include bottles, bottles with pumps, tottles, tubes (aluminum, plastic or laminated), jars, non-aerosol pump sprayers, aerosol containers, pouches, and packets. The packages can be configured for single-dose or multiple-dose administration.

In various embodiments, the compositions of the invention are hydrophobic. In other embodiments, the hydrophobic compositions are anhydrous. In various embodiments, the hydrophobic carriers are non-polar and/or non-volatile. In still other embodiments, the compositions are aqueous based. In other embodiments, the compositions of the invention are sterile. In other embodiments, the hydrophobic compositions are non-sterile. In other embodiments, the hydrophobic compositions have a low bioburden. In various embodiments, the hydrophobic compositions of the invention do not contain additional skin penetration enhancers. In other embodiments, the hydrophobic compositions of the invention do not contain additional volatile solvents. In still other embodiments, the hydrophobic compositions of the invention do not contain surfactants. In other embodiments, the hydrophobic compositions of the invention do not contain alcohols, $C_1$-$C_4$ aliphatic alcohols, or $C_1$-$C_5$ aliphatic alcohols. In other embodiments, the hydrophobic compositions do not contain polymers or copolymers.

A. Taxane Nanoparticles

Taxanes are poorly water soluble drugs having a solubility of less than or equal to 10 mg/mL in water at room temperature. Taxanes are widely used as chemotherapy agents. The term "taxanes" as used herein include paclitaxel (I), docetaxel (II), cabazitaxel (III), and/or any other taxane derivatives.

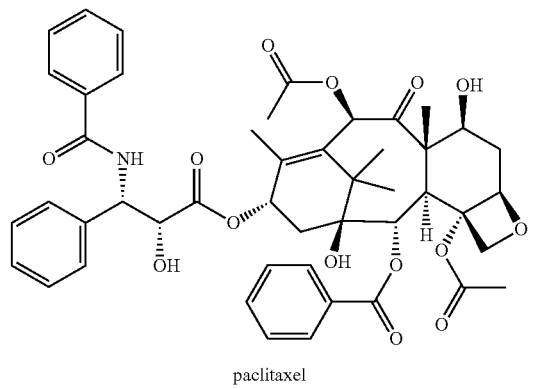

paclitaxel

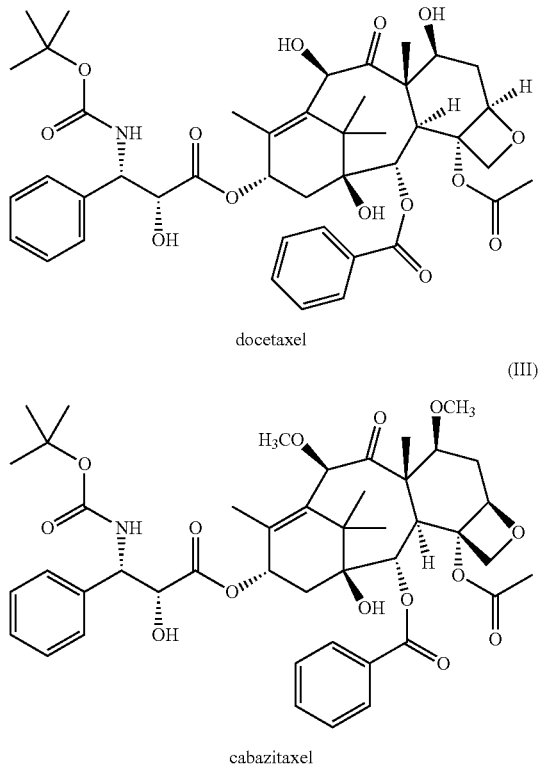

docetaxel cabazitaxel

The taxane nanoparticles can be paclitaxel nanoparticles, docetaxel nanoparticles, or cabazitaxel nanoparticles, or nanoparticles of other taxane derivatives. Paclitaxel and docetaxel active pharmaceutical ingredients (APIs) are commercially available from Phyton Biotech LLC, Vancouver, Canada. The docetaxel API and nanoparticles contain not less than 90%, or not less than 95%, or not less than 97.5% docetaxel calculated on the anhydrous, solvent-free basis. The paclitaxel API and nanoparticles contain not less than 90%, or not less than 95%, or not less than 97% paclitaxel calculated on the anhydrous, solvent-free basis. Paclitaxel API and nanoparticles can be prepared from a semisynthetic chemical process or from a natural source such as plant cell fermentation or extraction. Paclitaxel is also sometimes referred to by the trade name TAXOL, although this is a misnomer because TAXOL is the trade name of a solution of paclitaxel in polyoxyethylated castor oil and ethanol intended for dilution with a suitable parenteral fluid prior to intravenous infusion. Paclitaxel is a poorly water soluble drug. The solubility of paclitaxel in water is less than 0.05 ppm as determined experimentally by the solubility method described in Example 1. The taxane nanoparticles can be in a crystalline form or in an amorphous form or a combination of both.

In various embodiments of the present invention, the taxane or paclitaxel nanoparticles are uncoated (neat) individual particles; the taxane or paclitaxel nanoparticles are not bound to or conjugated to any substance; no substances are absorbed or adsorbed onto the surface of the taxane or paclitaxel nanoparticles; the taxane or paclitaxel nanoparticles are not encapsulated in any substance; the taxane or paclitaxel nanoparticles are not coated with any substance; the taxane or paclitaxel nanoparticles are not microemulsions, nanoemulsions, microspheres, or liposomes of a taxane or paclitaxel; the taxane or paclitaxel particles are not bound to, attached to, encapsulated in, or coated with a monomer, a polymer (or biocompatible polymer), a protein, a surfactant, or albumin; and/or a monomer, a polymer (or biocompatible polymer), a protein, a surfactant, or albumin is not absorbed or adsorbed onto the surface of the taxane or paclitaxel nanoparticles. In some embodiments, the compositions are free of/do not include or contain a polymer/copolymer or biocompatible polymer/copolymer. In some embodiments, the compositions are free of/do not include or contain a protein. In some aspects of the invention, the compositions are free of/do not include or contain albumin. In some aspects of the invention, the compositions are free of/do not include or contain hyaluronic acid. In some aspects of the invention, the compositions are free of/do not include or contain a conjugate of hyaluronic acid and a taxane. In some aspects of the invention, the compositions are free of/do not include or contain a conjugate of hyaluronic acid and paclitaxel. In some aspects of the invention, the compositions are free of/do not include or contain poloxamers, styrene-isobutylene-styrene (SIBS), a polyanhydride copolymer, polycaprolactone, polyethylene glycol, Poly (bis(P-carboxyphenoxy)propane-sebacic acid, and/or poly(D, L lactic-co-glycolic acid (PLGA).

The taxane nanoparticles, including paclitaxel nanoparticles, docetaxel nanoparticles, or cabazitaxel nanoparticles, can have a mean particle size (number) of from 0.01 microns to 1.5 microns, or from 0.01 microns to 1.2 microns, or from 0.01 microns to 1 micron, or from 0.01 microns to less than 1 micron, or from 0.01 microns to 0.9 microns, or from 0.01 microns to 0.8 microns, or from 0.01 microns to 0.7 microns, or from 0.1 microns to 1.5 microns, or from 0.1 microns to 1.2 microns, or from 0.1 microns to 1 micron, or from 0.1 microns to less than 1 micron, or from 0.1 microns to 0.9 microns, or from 0.1 microns to 0.8 microns, or from 0.1 to 0.7 microns, or from 0.2 microns to 1.5 microns, or from 0.2 microns to 1.2 microns, or from 0.2 microns to 1 micron, or from 0.2 microns to less than 1 micron, or from 0.2 microns to 0.9 microns, or from 0.2 microns to 0.8 microns, or from 0.2 microns to 0.7 microns, or from 0.3 microns to 1.5 microns, or from 0.3 microns to 1.2 microns, or from 0.3 microns to 1 micron, or from 0.3 microns to less than 1 micron, or from 0.3 microns to 0.9 microns, or from 0.3 microns to 0.8 microns, or from 0.3 microns to 0.7 microns, or from 0.4 microns to 1.5 microns, or from 0.4 microns to 1.2 microns, or from 0.4 microns to 1 micron, or from 0.4 microns to less than 1 micron, or from 0.4 microns to 0.9 microns, or from 0.4 microns to 0.8 microns, or from 0.4 microns to 0.7 microns, or from 0.5 microns to 1.5 microns, or from 0.5 microns to 1.2 microns, or from 0.5 microns to 1 micron, or from 0.5 microns to less than 1 micron, or from 0.5 microns to 0.9 microns, or from 0.5 microns to 0.8 microns, or form 0.5 microns to 0.7 microns, or from 0.6 microns to 1.5 microns, or from 0.6 microns to 1.2 microns, or from 0.6 microns to 1 micron, or from 0.6 microns to less than 1 micron, or from 0.6 microns to 0.9 microns, or from 0.6 microns to 0.8 microns, or from 0.6 microns to 0.7 microns.

The particle size of the taxane when incorporated in a composition is determined by a particle size analyzer instrument and the measurement is expressed as the mean diameter based on a number distribution. A suitable particle size analyzer instrument is one which employs the analytical technique of light obscuration, also referred to as photozone or single particle optical sensing (SPOS). A suitable light obscuration particle size analyzer instrument is the ACCU-SIZER available from Particle Sizing Systems, Port Richey, Fla.

In various embodiments, the mean particle size of the taxane nanoparticles incorporated in a composition does not grow larger than 20% of the initial mean particle size when the composition is stored at room temperature for at least 1 month, or for at least 3 months, or for at least 6 months or for at least 12 months. The term "initial mean particle size", as used herein with regard to the particle size of taxane nanoparticles, is the mean particle size of the taxane incorporated in the composition when measured by a particle size analyzer instrument within 45 days after the completion of manufacture of the composition (date of manufacture), and the initial mean particle size is from 0.1 microns to 1.5 microns (number) or from 0.01 microns to 1.5 microns (number).

Nanoparticles of taxanes can be manufactured using various particle size-reduction methods and equipment known in the art. Such methods include, but are not limited to, wet or dry milling, micronizing, disintegrating, pulverizing, and supercritical carbon dioxide particle size reduction methods. In various embodiments, the taxane or paclitaxel nanoparticles are made by a supercritical carbon dioxide particle reduction method (also known as "precipitation with compressed anti-solvents" or "PCA") as disclosed in U.S. Pat. Nos. 5,874,029, 5,833,891, 6,113,795, 7,744,923, 8,778,181, US publication 2014/0296140, US publication 2016/0354336, US publication 2016/0374953, and international patent application publication WO 2016/197091 (application no. PCT/US16/35993) all of which are herein incorporated by reference.

In the supercritical carbon dioxide particle size reduction method, supercritical carbon dioxide (anti-solvent) and solvent, e.g. acetone or ethanol, are employed to generate uncoated taxane nanoparticles within a well-characterized particle-size distribution. The carbon dioxide and acetone are removed during processing (up to 0.5% residual solvent may remain), leaving taxane nanoparticle powder generally ranging in size from about 200 nm to about 800 nm. Stability studies show that the powder is stable in a vial dose form when stored at controlled room temperature (25° C./60% relative humidity) for up to 59 months and under accelerated conditions (40° C./75% relative humidity) for up to six months.

Taxane nanoparticles produced by various supercritical carbon dioxide particle size reduction methods can have unique physical characteristics as compared to taxane nanoparticles produced by conventional particle size reduction methods using physical impacting or grinding, e.g., wet or dry milling, micronizing, disintegrating, comminuting, microfluidizing, or pulverizing. As disclosed in US publication 2016/0354336 and international patent application publication WO 2016/197091 all of which are herein incorporated by reference, such unique characteristics include a bulk density (not tapped) between 0.05 g/cm$^3$ and 0.15 g/cm$^3$ and a specific surface area (SSA) of at least 18 m$^2$/g of taxane (paclitaxel and docetaxel) nanoparticles, which are produced by the supercritical carbon dioxide particle size reduction methods described in US publication 2016/0354336 and international patent application publication WO 2016/197091 and as described below. This bulk density range is generally lower than the bulk density of taxane particles produced by conventional means, and the SSA is generally higher than the SSA of taxane particles produced by conventional means. These unique characteristics result in significant increases in dissolution rates in water/methanol media as compared to taxanes produced by conventional means. As used herein, the "specific surface area (SSA)" is the total surface area of the taxane nanoparticle per unit of taxane mass as measured by the Brunauer-Emmett-Teller ("BET") isotherm by the following method: a known mass between 200 and 300 mg of the analyte is added to a 30 mL sample tube. The loaded tube is then mounted to a Porous Materials Inc. SORPTOMETER®, model BET-202A. The automated test is then carried out using the BETWIN® software package and the surface area of each sample is subsequently calculated. The bulk density measurement can be conducted by pouring the taxane nanoparticles into a graduated cylinder without tapping at room temperature, measuring the mass and volume, and calculating the bulk density.

As disclosed in US publication 2016/0354336 and international patent application publication WO 2016/197091, studies showed a SSA of 15.0 m$^2$/g and a bulk density of 0.31 g/cm$^3$ for paclitaxel nanoparticles produced by milling paclitaxel in a Deco-PBM-V-0.41 ball mill suing a 5 mm ball size, at 600 RPM for 60 minutes at room temperature. Also disclosed in US publication 2016/0354336 and international patent application publication WO 2016/197091, one lot of paclitaxel nanoparticles had a SSA of 37.7 m$^2$/g and a bulk density of 0.085 g/cm$^3$ when produced by a supercritical carbon dioxide method using the following method: a solution of 65 mg/ml of paclitaxel was prepared in acetone. A BETE MicroWhirl® fog nozzle (BETE Fog Nozzle, Inc.) and a sonic probe (Qsonica, model number Q700) were positioned in the crystallization chamber approximately 8 mm apart. A stainless steel mesh filter with approximately 100 nm holes was attached to the crystallization chamber to collect the precipitated paclitaxel nanoparticles. The supercritical carbon dioxide was placed in the crystallization chamber of the manufacturing equipment and brought to approximately 1200 psi at about 38° C. and a flow rate of 24 kg/hour. The sonic probe was adjusted to 60% of total output power at a frequency of 20 kHz. The acetone solution containing the paclitaxel was pumped through the nozzle at a flow rate of 4.5 mL/minute for approximately 36 hours. Additional lots of paclitaxel nanoparticles produced by the supercritical carbon dioxide method described above had SSA values of: 22.27 m$^2$/g, 23.90 m$^2$/g, 26.19 m$^2$/g, 30.02 m$^2$/g, 31.16 m$^2$/g, 31.70 m$^2$/g, 32.59 m$^2$/g, 33.82 m$^2$/g, 35.90 m$^2$/g, 38.22 m$^2$/g, and 38.52 m$^2$/g.

As disclosed in US publication 2016/0354336 and international patent application publication WO 2016/197091, studies showed a SSA of 15.2 m$^2$/g and a bulk density of 0.44 g/cm$^3$ for docetaxel nanoparticles produced by milling docetaxel in a Deco-PBM-V-0.41 ball mill suing a 5 mm ball size, at 600 RPM for 60 minutes at room temperature. Also disclosed in US publication 2016/0354336 and international patent application publication WO 2016/197091, docetaxel nanoparticles had a SSA of 44.2 m$^2$/g and a bulk density of 0.079 g/cm$^3$ when produced by a supercritical carbon dioxide method using the following method: A solution of 79.32 mg/ml of docetaxel was prepared in ethanol. The nozzle and a sonic probe were positioned in the pressurizable chamber approximately 9 mm apart. A stainless steel mesh filter with approximately 100 nm holes was attached to the pressurizable chamber to collect the precipitated docetaxel nanoparticles. The supercritical carbon dioxide was placed in the pressurizable chamber of the manufacturing equipment and brought to approximately 1200 psi at about 38° C. and a flow rate of 68 slpm. The sonic probe was adjusted to 60% of total output power at a frequency of 20 kHz. The ethanol solution containing the docetaxel was pumped through the nozzle at a flow rate of 2 mL/minute for approximately 95 minutes). The precipitated docetaxel agglomerates and particles were then collected from the supercritical carbon dioxide as the mixture is pumped through the stainless steel mesh filter. The filter containing the nanoparticles of docetaxel was opened and the resulting product was collected from the filter.

As disclosed in US publication 2016/0354336 and international patent application publication WO 2016/197091, dissolution studies showed an increased dissolution rate in methanol/water media of paclitaxel and docetaxel nanoparticles made by the supercritical carbon dioxide methods described in US publication 2016/0354336 and international patent application publication WO 2016/197091 as compared to paclitaxel and docetaxel nanoparticles made by milling paclitaxel and docetaxel using a Deco-PBM-V-0.41 ball mill suing a 5 mm ball size, at 600 RPM for 60 minutes at room temperature. The procedures used to determine the dissolution rates are as follows. For paclitaxel, approximately 50 mg of material were coated on approximately 1.5 grams of 1 mm glass beads by tumbling the material and beads in a vial for approximately 1 hour. Beads were transferred to a stainless steel mesh container and placed in the dissolution bath containing methanol/water 50/50 (v/v) media at 37° C., pH 7, and a USP Apparatus II (Paddle), operating at 75 rpm. At 10, 20, 30, 60, and 90 minutes, a 5 mL aliquot was removed, filtered through a 0.22 μm filter and analyzed on a UV/VIS spectrophotometer at 227 nm. Absorbance values of the samples were compared to those of standard solutions prepared in dissolution media to determine the amount of material dissolved. For docetaxel, approximately 50 mg of material was placed directly in the dissolution bath containing methanol/water 15/85 (v/v) media at 37° C., pH 7, and a USP Apparatus II (Paddle), operating at 75 rpm. At 5, 15, 30, 60, 120 and 225 minutes, a 5 mL aliquot was removed, filtered through a 0.22 μm filter, and analyzed on a UV/VIS spectrophotometer at 232 nm. Absorbance values of the samples were compared to those of standard solutions prepared in dissolution media to determine the amount of material dissolved. For paclitaxel, the dissolution rate was 47% dissolved in 30 minutes for the nanoparticles made by the supercritical carbon dioxide method versus 32% dissolved in 30 minutes for the nanoparticles made by milling. For docetaxel, the dissolution rate was 27% dissolved in 30 minutes for the nanoparticles made by the supercritical carbon dioxide method versus 9% dissolved in 30 minutes for the nanoparticles made by milling.

In some embodiments, the paclitaxel nanoparticles have an SSA of at least 18, at least 19, at least 20, at least 21, at least 22, at least 23, at least 24, at least 25, at least 26, at least 27, at least 28, at least 29, at least 30, at least 31, at least 32, at least 33, at least 34, or at least 35 $m^2/g$. In other embodiments, the paclitaxel nanoparticles have an SSA of 18 $m^2/g$ to 50 $m^2/g$, or 20 $m^2/g$ to 50 $m^2/g$, or 22 $m^2/g$ to 50 $m^2/g$, or 25 $m^2/g$ to 50 $m^2/g$, or 30 $m^2/g$ to 50 $m^2/g$, or 18 $m^2/g$ to 45 $m^2/g$, or 20 $m^2/g$ to 45 $m^2/g$, or 22 $m^2/g$ to 45 $m^2/g$, or 25 $m^2/g$ to 45 $m^2/g$, or 30 $m^2/g$ to 45 $m^2/g$, or 18 $m^2/g$ to 40 $m^2/g$, or 20 $m^2/g$ to 40 $m^2/g$, or 22 $m^2/g$ to 40 $m^2/g$, or 25 $m^2/g$ to 40 $m^2/g$, or 30 $m^2/g$ to 40 $m^2/g$.

In some embodiments, the paclitaxel nanoparticles have a bulk density (not-tapped) of 0.05 $g/cm^3$ to 0.15 $g/cm^3$, or 0.05 $g/cm^3$ to 0.20 $g/cm^3$.

In some embodiments, the paclitaxel nanoparticles have a dissolution rate of at least 40% w/w dissolved in 30 minutes or less in a solution of 50% methanol/50% water (v/v) in a USP II paddle apparatus operating at 75 RPM, at 37° C., and at a pH of 7.

In some embodiments, the docetaxel nanoparticles have an SSA of at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, or at least 42 $m^2/g$. In other embodiments, the docetaxel nanoparticles have an SSA of 18 $m^2/g$ to 60 $m^2/g$, or 22 $m^2/g$ to 60 $m^2/g$, or 25 $m^2/g$ to 60 $m^2/g$, or 30 $m^2/g$ to 60 $m^2/g$, or 40 $m^2/g$ to 60 $m^2/g$, or 18 $m^2/g$ to 50 $m^2/g$, or 22 $m^2/g$ to 50 $m^2/g$, or 25 $m^2/g$ to 50 $m^2/g$, or 30 $m^2/g$ to 50 $m^2/g$, or 40 $m^2/g$ to 50 $m^2/g$.

In some embodiments, the docetaxel nanoparticles have a bulk density (not-tapped) of 0.05 $g/cm^3$ to 0.15 $g/cm^3$.

In some embodiments, the docetaxel nanoparticles have a dissolution rate of at least 20% w/w dissolved in 30 minutes or less in a solution of 15% methanol/85% water (v/v) in a USP II paddle apparatus operating at 75 RPM, at 37° C., and at a pH of 7.

It was found that paclitaxel nanoparticle crystals have a tendency to grow in suspensions of water or saline solutions over time forming large needle-like crystals. A crystal growth study was conducted and the results are shown in Table 2 in Example 2 below. It was found that the nanoparticle crystals did not grow in the hydrophobic materials. Also, and surprisingly, the nanoparticle crystals did not grow in aqueous solutions of benzalkonium chloride, CARBOPOL ULTREZ 10, or poloxamer 407.

B. Hydrophobic Carriers

The hydrophobic carriers of the present invention can comprise substances from plant, animal, paraffinic, and/or synthetically derived sources. Hydrophobic substances are generally known as substances that lack an affinity for and repel water. The hydrophobic carrier can be the continuous phase of the compositions. In various embodiments, the hydrophobic carriers are non-polar and/or non-volatile. Non-limiting examples include fats, butters, greases, waxes, solvents, and oils; mineral oils; vegetable oils; petrolatums; water insoluble organic esters and triglycerides; and fluorinated compounds. The hydrophobic carriers can also comprise silicone materials. Silicone materials are defined as compounds based on polydialkylsiloxanes and include polymers, elastomers (crosslinked silicones), and adhesives (branched silicones). Non-limiting examples of silicone materials include dimethicone (polydimethylsiloxane), dimethicone copolyol, cyclomethicone, simethicone, silicone elastomers such as ST-elastomer 10 (DOW CORNING), silicone oils, silicone polymers, volatile silicone fluids, and silicone waxes. In some embodiments, the hydrophobic carrier does not comprise silicone materials.

Plant derived materials include, but are not limited to, arachis (peanut) oil, balsam Peru oil, carnauba wax, candellila wax, castor oil, hydrogenated castor oil, cocoa butter, coconut oil, corn oil, cotton seed oil, jojoba oil, macadamia seed oil, olive oil, orange oil, orange wax, palm kernel oil, rapeseed oil, safflower oil, sesame seed oil, shea butter, soybean oil, sunflower seed oil, tea tree oil, vegetable oil, and hydrogenated vegetable oil.

Non-limiting examples of animal derived materials include beeswax (yellow wax and white wax), cod liver oil, emu oil, lard, mink oil, shark liver oil, squalane, squalene, and tallow. Non-limiting examples of paraffinic materials include isoparaffin, microcrystalline wax, heavy mineral oil, light mineral oil, ozokerite, petrolatum, white petrolatum, and paraffin wax.

Non-limiting examples of organic esters and triglycerides include $C_{12}$-15 alkyl benzoate, isopropyl myristate, isopropyl palmitate, medium chain triglycerides, mono- and di-glycerides, trilaurin, and trihydroxystearin.

A non-limiting example of a fluorinated compound is perfluoropolyether (PFPE), such as FOMBLIN®HC04 commercially available from Solvay Specialty Polymers.

The hydrophobic carriers of the present invention can comprise pharmaceutical grade hydrophobic substances. In various embodiments of the present invention the hydrophobic carriers comprise petrolatum, mineral oil, or paraffin, or mixtures thereof. In some embodiments, the mineral oil is heavy mineral oil. In some embodiments, the hydrophobic carriers are not polymeric matrices and do not contain a polymer or biodegradable polymer, such as styrene-isobutylene-styrene (SIBS), a polyanhydride copolymer, polycaprolactone, polyethylene glycol, Poly (bis(P-carboxyphenoxy) propane-sebacic acid, and/or poly(D, L lactic-co-glycolic acid (PLGA), and/or do not contain a copolymer such as a poloxamer.

In some embodiments, the concentration of the hydrophobic carrier in the compositions is greater than 10% w/w of the total composition weight. In other embodiments, the concentration of the hydrophobic carrier in the compositions is greater than 15%, or greater than 20%, or greater than 25%, or greater than 30%, or greater than 35%, or greater than 40%, or greater than 45%, or greater than 50%, or greater than 55%, or greater than 60%, or greater than 65%, or greater than 70%, or greater than 75%, or greater than 80%, or greater than 82%, or greater than 85%, or greater than 87%, or greater than 90% w/w of the total composition weight. In other embodiments, the concentration of the hydrophobic carrier in the compositions is from greater than 10% w/w to 95% w/w of the total composition weight. In other embodiments, the concentration of the hydrophobic carrier in the compositions is from 11% w/w to 95% w/w, or from 12% w/w to 95% w/w, or from 13% w/w to 95% w/w, or from 14% w/w to 95% w/w, or from 15% w/w to 95% w/w, or from 16% w/w to 95% w/w, or from 17% w/w to 95% w/w, or from 18% w/w to 95% w/w, or from 19% w/w to 95% w/w, or from 20% w/w to 95% w/w of the total composition weight.

(i) Petrolatum

Petrolatum is a purified mixture of semi-solid saturated hydrocarbons obtained from petroleum, and varies from dark amber to light yellow in color. White petrolatum is wholly or nearly decolorized and varies from cream to snow white in color. Petrolatums are available with different melting point, viscosity, and consistency characteristics. Petrolatums may also contain a stabilizer such as an antioxidant. Pharmaceutical grades of petrolatum include Petrolatum USP and White Petrolatum USP.

Various petrolatums are available commercially from the Penreco Corporation under the trade names: ULTIMA, SUPER, SNOW, REGENT, LILY, CREAM, ROYAL, BLOND, and AMBER. Various grades of petrolatum are also available commercially from the Sonneborn Corporation under the trade names: ALBA, SUPER WHITE PROTOPET, SUPER WHITE FONOLINE, WHITE PROTOPET 1S, WHITE PROTOPET 2L, WHITE PROTOPET 3C, WHITE FONOLINE, PERFECTA, YELLOW PROTOPET 2A, YELLOW FONOLINE, PROTOLINE, SONOJELL #4, SONOJELL #9, MINERAL JELLY #10, MINERAL JELLY #14, MINERAL JELLY #17, AND CARNATION TROUGH GREASE. Petrolatums are also available from the Spectrum Chemical Mfg. Corp.

(ii) Mineral Oil

Mineral oil is a mixture of liquid hydrocarbons obtained from petroleum. Mineral oil is available in various viscosity grades, such as light mineral oil, heavy mineral oil, and extra heavy mineral oil. Light mineral oil has a kinematic viscosity of not more than 33.5 centistokes at 40° C. Heavy mineral oil has a kinematic viscosity of not less than 34.5 centistokes at 40° C. Mineral oil may contain a suitable stabilizer. Pharmaceutical grades of mineral oil include Mineral Oil USP, which is heavy mineral oil, and Light Mineral Oil NF, which is light mineral oil. Mineral oil is commercially available from the Penreco Corporation under the DRAKEOL trade name, and the Sonneborn Corporation under the trade names BENOL, BLANDOL, BRITOL, CARNATION, ERVOL, GLORIA, KAYDOL, KLEAROL, PROTOL, and RUDOL. Mineral oil is also commercially available from the Spectrum Chemical Mfg. Corp.

(iii) Paraffin Wax

Paraffin wax is a purified mixture of solid hydrocarbons obtained from petroleum. It may also be synthetically derived by the Fischer-Tropsch process from carbon monoxide and hydrogen which are catalytically converted to a mixture of paraffin hydrocarbons. Paraffin wax may contain an antioxidant. Pharmaceutical grades of paraffin wax include Paraffin NF and Synthetic Paraffin NF. Paraffin waxes are commercially available from the Spectrum Chemical Mfg. Corp, Koster Keunen, Inc. and Frank B. Ross, Inc.

C. Volatile Silicone Fluids

Volatile silicone fluids, also known as volatile silicone oils, are volatile liquid polysiloxanes which can by cyclic or linear. They are liquid at room temperature. Volatile silicone fluids are hydrophobic materials. Linear volatile silicone fluids include polydimethylsiloxane, hexamethyldisiloxane and octamethyltrisiloxane and are commercially available from Dow Corning under the trade names DOW CORNING Q7-9180 Silicone Fluid 0.65 cSt and DOW CORNING Q7-9180 Silicone Fluid 1.0 cSt, respectively. Cyclic volatile silicone fluids are generally known as cyclomethicones.

(i) Cyclomethicone

Cyclomethicone is a fully methylated cyclic siloxane containing repeating units of formula (IV):

$$[-(CH_3)_2SiO-]_n \qquad (IV)$$

in which n is 3, 4, 5, 6, or 7; or mixtures thereof. Cyclomethicone is a clear, colorless volatile liquid silicone fluid. Cyclomethicone has emollient properties and helps to improve the tactile feel of an oil based product by making it feel less greasy on the skin. Pharmaceutical grade cyclomethicone includes Cyclomethicone NF. Cyclomethicone NF is represented by formula (IV) in which n is 4 (cyclotetrasiloxane), 5 (cyclopentasiloxane), or 6 (cyclohexasiloxane); or mixtures thereof. Cyclopentasiloxane, also known as decamethylcylcopentasiloxane, cyclomethicone D5, or cyclomethicone 5, is the cyclomethicone represented by formula (IV) in which n is 5 (pentamer), but it can contain small amounts (generally less than 1%) of one or more of the other cyclic chain length cyclomethicones. Cyclopentasiloxane is available in a pharmaceutical grade as Cyclomethicone NF. Cyclomethicones are commercially available from Dow Corning under the trade names DOW CORNING ST-Cyclomethicone 5-NF, DOW CORNING ST-Cyclomethicone 56-NF, and XIAMETER PMX-0245. It is also commercially available from the Spectrum Chemical Mfg. Corp. Cyclopentasiloxane has a vapor pressure of about 20 to about 27 Pa at 25° C.

Cyclomethicone has been shown to be non-irritating to vaginal tissues. A 2011 study by Forbes et. al., (Forbes et. al., Non-aqueous silicone elastomer gels as a vaginal microbicide delivery system for the HIV-1 entry inhibitor maraviroc, Journal of Controlled Release, 156 (2011), 161-169) compared a silicone elastomer gel containing 20% cyclomethicone and 80% ST-Elastomer-10 to hydroxyethylcellulose (HEC) as a vehicle for vaginal administration of maraviroc (an HIV-1 entry inhibitor). A PK study was performed in rhesus macaques to determine plasma, vaginal fluid and vaginal tissue levels. Three milliliters of silicone elastomer gel or HEC, both containing 100 mg maraviroc, were vaginally administered to 12 non-infected, female macaques. Vaginal fluids were collected at time points up to 3 days post-application. A single vaginal pinch-biopsy was taken from each macaque at 24 hours post-application. All time points after 4 hours showed higher concentrations of maraviroc for the silicone elastomer gel. Vaginal biopsy samples showed maraviroc levels were seven times higher for the silicone elastomer gel than HEC. There was no mention of vaginal irritation or ulceration in macaques receiving the elastomer/cyclomethicone gel. To test mucosal toxicity/irritability, the authors performed a slug mucosal irritation test. LDH and other proteins are released from the foot of a slug in response to cell damage, and serve as markers for mucosal toxicity. The test was performed by placing a slug on top of a sample for 30 minutes. The slug was subsequently transferred to a petri dish containing PBS for 60 minutes, and then a second PBS petri dish for an additional 60 minutes. The amounts of LDH protein and mucous left behind in the PBS were measured to determine irritability of the samples. LDH and mucus levels of the silicone elastomer gel and HEC were both comparable to the negative control.

In one embodiment, the concentration of cyclomethicone in the composition is less than 25% w/w. In another embodiment, the cyclomethicone in the composition is at a concentration from 5 to 24% w/w. In another embodiment, the concentration of cyclomethicone is from 5 to 20% w/w. In another embodiment, the cyclomethicone is at a concentration of from 5 to 18% w/w. In another embodiment, the concentration of cyclomethicone is 13% w/w. In various embodiments, the concentration of cyclomethicone can be 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, or 24% w/w or any percentage derivable therein of the total composition weight. In one embodiment, the cyclomethicone is cyclopentasiloxane.

D. Aqueous Based Compositions

Aqueous based compositions of the invention comprise taxane nanoparticles and an aqueous carrier. The aqueous formulations are dispersions (suspensions) of the taxane nanoparticles in an aqueous carrier. The taxane nanoparticles can be completely dispersed, partially dispersed and partially dissolved, but not completely dissolved in the aqueous carrier. An aqueous based composition is a composition in which water is the major constituent. Aqueous carriers can include single phase aqueous solutions, and multi-phase aqueous based emulsions such oil-in-water and water-in-oil emulsions.

It was observed that taxane nanoparticle crystals, such as paclitaxel nanoparticles, rapidly grew in water and in aqueous based carriers. In many cases, the growth was observed in as little as 3 days at room temperature, and some cases in 24 hours. Many of the crystals were needle-like in shape and were larger than 5 μm in length. A study was conducted and the results are shown in Table 2 in Example 2. Surprisingly, the taxane nanoparticle crystal growth was inhibited by the addition of poloxamer 407, a quaternary ammonium compound, or a cross-linked acrylic acid polymer to the aqueous based carrier during processing. The addition of poloxamer 188 did not inhibit the growth of the nanoparticle crystals.

It was also observed that the presence of a quaternary ammonium compound, or a cross-linked acrylic acid polymer, or mixtures thereof in an aqueous carrier comprising taxane nanoparticle crystals prevented growth of the nanoparticle crystals over time. A study was conducted and the results are shown in Table 11 in Example 8 revealing that the mean particle size of poorly water soluble taxane nanoparticles (paclitaxel) in an aqueous composition comprising poloxamer 407, a quaternary ammonium compound, or a cross-linked acrylic acid polymer, or mixtures thereof does not grow larger than 20% of the initial mean particle size when the aqueous composition is stored at room temperature for 6 months. In some embodiments, there is disclosed an aqueous based composition comprising an aqueous carrier; a plurality of taxane nanoparticles; and a quaternary ammonium compound, or a cross-linked acrylic acid polymer, or mixtures thereof; wherein the mean particle size of the taxane nanoparticles is from 0.1 microns to 1.5 microns (number) or from 0.01 microns to 1.5 microns (number), and wherein the mean particle size of the taxane nanoparticles does not grow larger than 20% of the initial mean particle size when the composition is stored at room temperature for at least 6 months. In other embodiments, the composition further comprises poloxamer 407.

In one aspect of the invention, disclosed are compositions comprising taxane nanoparticles, an aqueous carrier, and poloxamer 407, a quaternary ammonium compound, or a cross-linked acrylic acid polymer, or mixtures thereof. It was surprisingly found that the addition of poloxamer 407, a quaternary ammonium compound, or a cross-linked acrylic acid polymer inhibited the crystal growth of the taxane nanoparticles in aqueous carriers. The aqueous based compositions of the invention are suitable for topical, injectable, (IV) infusion, or oral liquid dosage forms. In one embodiment, the additive to inhibit crystal growth is poloxamer 407. In various embodiments, the quaternary ammonium compound is the additive to inhibit crystal growth and is benzalkonium chloride or benzethonium chloride. In other embodiments, the quaternary ammonium compound is benzalkonium chloride. In other embodiments, the cross-linked acrylic acid polymer is the additive to inhibit crystal growth and is Carbomer.

In one aspect of the invention, the composition comprises poloxamer 407 and taxane nanoparticles in an aqueous carrier suitable for injection delivery including (IV) infusion. In various embodiments, the taxane nanoparticles are docetaxel nanoparticles, paclitaxel nanoparticles, or cabazitaxel nanoparticles.

In another aspect of the invention, the composition comprises a quaternary ammonium compound and taxane nanoparticles in an aqueous carrier suitable for injection delivery including (IV) infusion. In various embodiments, the taxane nanoparticles are docetaxel nanoparticles, paclitaxel nanoparticles, or cabazitaxel nanoparticles. In other embodiments, the quaternary ammonium compounds are benzalkonium chloride or benzethonium chloride.

In one aspect of the invention, disclosed are methods of inhibiting the growth of a dispersion of crystalline taxane nanoparticles in an aqueous based carrier, the method comprising adding poloxamer 407, a quaternary ammonium compound, or a cross-linked acrylic acid polymer, or mixtures thereof, to the aqueous based carrier during processing, wherein the mean particle size of the taxane nanoparticles is from 0.1 microns to 1.5 microns (number) or from 0.01 microns to 1.5 microns (number). In some embodiments, the quaternary ammonium compound is benzalkonium chloride or benzethonium chloride. In some embodiments, the cross-linked acrylic acid polymer is carbomer. In some embodiments, the taxane nanoparticles are paclitaxel nanoparticles, docetaxel nanoparticles, or cabazitaxel nanoparticles. In still other embodiments, the taxane nanoparticles are paclitaxel nanoparticles.

(i) Poloxamer 407

Poloxamer 407 is a solid, hydrophilic, nonionic, synthetic block copolymer of ethylene oxide and propylene oxide conforming to the general formula (V)

$$HO(C_2H_4O)_a(C_3H_6O)_b(C_2H_4O)_aH \quad (V)$$

where a is 101 and b is 56. Poloxamer 407 has an average molecular weight of 9840-14600. The term "poloxamer" is the nonproprietary name of the copolymer. Poloxamers are available in several types which have various physical forms and various average molecular weights. Each specific poloxamer type is identified by the nonproprietary name "poloxamer" followed by a three digit number, the first two digits of which when multiplied by 100 correspond to the approximate average molecular weight of the polyoxypropylene portion of the copolymer; and the third digit, when multiplied by 10, corresponds to the percentage by weight of the polyoxyethylene portion. Poloxamers are available in pharmaceutical, cosmetic, and industrial grades. Pharmaceutical grade poloxamers are listed in recognized pharmaceutical compendia such as USP/NF and European Pharmacopeia (PhEur). According to the USP/NF and PhEur, a suitable antioxidant may be added. Poloxamer 407 is commercially available from BASF under the trade name PLURONIC® F127. The addition of poloxamer 188 to an aqueous carrier did not inhibit crystal growth of the taxane nanoparticles. Suitable concentrations of Poloxamer 407 are at least 2% w/w, or from 0.1 to 25% w/w, or from 0.1 to 20% w/w, or from 0.1 to 15% w/w, or from 0.1 to 10% w/w, or from 1 to 25% w/w, or from 1 to 20% w/w, or from 1 to 15% w/w, or from 1 to 10% w/w, or from 2 to 25% w/w, or from 2 to 20% w/w, or from 2 to 15% w/w, or from 2 to 10% w/w.

(ii) Quaternary Ammonium Compounds

Quaternary ammonium compounds (including salts) are positively charged tetra-substituted nitrogen derivatives of formula (VI)

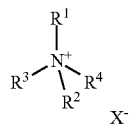

(VI)

In which $R^1$, $R^2$, $R^3$, and $R^4$ may be the same or different, but may not be hydrogen. $X^-$ represents a typical anion such as chloride. Suitable quaternary ammonium compounds include benzalkonium chloride and benzethonium chloride. Benzalkonium chloride is commercially available in a 100% powder or a 50% aqueous solution. Other examples of quaternary ammonium compounds are disclosed in the International Cosmetic Ingredient Dictionary and Handbook, 12th edition, 2008 herein incorporated by reference. Suitable concentrations of quaternary ammonium compounds are at least 0.05% w/w, or at least 0.1% w/w, or at least 1% w/w, or at least 2% w/w, or from 0.05 to 5% w/w, or from 0.1 to 5% w/w, or from 1 to 5% w/w, or from 2 to 5% w/w.

(iii) Cross-Linked Acrylic Acid Polymers

Cross-linked acrylic acid polymers are high molecular weight homo- and co-polymers of acrylic acid cross-linked with a polyalkenyl polyether. Suitable cross-linked acrylic acid polymers include Carbomer (INCI name), Acrylates Copolymer (INCI name), Acrylates/$C_{10}$-30 Alkyl Acrylate Crosspolymer (INCI name), Acrylates Crosspolymer-4 (INCI name), and Polyacrylate-1 Crosspolymer (INCI name). The above mentioned polymers are all commercially available from the Lubrizol Corporation under the CARBOPOL® trade name. Examples of Carbomer available from the Lubrizol Corporation include CARBOPOL 934, CARBOPOL 934P, CARBOPOL 940, CARBOPOL 941, CARBOPOL 980, CARBOPOL 981, CARBOPOL 2984, CARBOPOL 5984, CARBOPOL SILK 100, CARBOPOL ETD 2050, ULTREZ 10, and ULTREZ 30. Examples of Acrylates Copolymer available from the Lubrizol Corporation include CARBOPOL AQUA SF-1, and CARBOPOL AQUA SF-1 OS. Examples of Acrylates/$C_{10}$-30 Alkyl Acrylate Crosspolymer available from the Lubrizol Corporation include CARBOPOL ULTREZ 20, CARBOPOL ULTREZ 21, CARBOPOL ETD 2020, CARBOPOL 1342, CARBOPOL 1382, and CARBOPOL SC-200. An example of Acrylates Crosspolymer-4 is CARBOPOL AQUA SF-2. An example of Polyacrylate-1 Crosspolymer is CARBOPOL AQUA CC. Suitable concentrations of cross-linked acrylic acid polymers are at least 0.1% w/w, or 0.5% w/w, or from 0.1 to 5% w/w, or from 0.5 to 5% w/w.

E. Additional Ingredients and Adjuvants

The compositions of the invention can further comprise functional ingredients suitable for use in pharmaceutical compositions. Non-limiting examples include absorbents, acidifying agents, antimicrobial agents, antioxidants, binders, biocides, buffering agents, bulking agents, crystal growth inhibitors, chelating agents, colorants, deodorant agents, emulsion stabilizers, film formers, fragrances, humectants, lytic agents, enzymatic agents, opacifying agents, oxidizing agents, pH adjusters, plasticizers, preservatives, reducing agents, emollient skin conditioning agents, humectant skin conditioning agents, moisturizers, surfactants, emulsifying agents, cleansing agents, foaming agents, hydrotopes, solvents, suspending agents, viscosity control agents (rheology modifiers), viscosity increasing agents (thickeners), and propellants. Listings and monographs of the examples of the functional ingredients described herein are disclosed in The International Cosmetic Ingredient Dictionary and Handbook (INCI), 12$^{th}$ Edition, 2008, herein incorporated by reference.

The compositions of the invention can further comprise additional pharmaceutically active ingredients, cosmetically active ingredients, and veterinary agents suitable for topical use.

Although, the hydrophobic compositions of the present invention can further comprise additional penetration enhancers, it was found that it was not necessary to include additional penetration enhancers to increase the skin penetration (i.e., into the epidermal and dermal portions of skin) of the taxane nanoparticles in hydrophobic compositions comprising a hydrophobic carrier and one or more volatile silicone fluids. In fact, the additions of skin penetration enhancers had little or no effect on the skin penetration of the hydrophobic compositions.

The term "penetration enhancer" has been used to describe compounds or materials or substances that facilitate drug absorption through the skin. These compounds or materials or substances can have a direct effect on the permeability of the skin, or they can augment percutaneous absorption by increasing the thermodynamic activity of the penetrant, thereby increasing the effective escaping tendency and concentration gradient of the diffusing species. The predominant effect of these enhancers is to either increase the stratum corneum' s degree of hydration or disrupt its lipoprotein matrix, the net result in either case being a decrease in resistance to drug (penetrant) diffusion (Remington, The Science and Practice of Pharmacy, $22^{nd}$ ed.).

Non-limiting examples of skin penetration enhancers include oleyl alcohol, isopropyl myristate, dimethyl isosorbide (DMI) available under the tradename ARLASOLVE DMI, and Diethylene Glycol Monoethyl Ether (DGME) which is available under the trade name TRANSCUTOL P. Other examples of skin penetration enhancers can be found in "Skin Penetration Enhancers Cited in the Technical Literature", Osborne, David W., and Henke, Jill J., Pharmaceutical Technology, November 1997, herein incorporated by reference. Such examples include: Fatty alcohols such as aliphatic alcohols, Decanol, Lauryl alcohol (dodecanol), Linolenyl alcohol, Nerolidol, 1-Nonanol, n-Octanol, Oleyl alcohol, Fatty acid esters, Butylacetate, Cetyl lactate, Decyl N,N-dimethylamino acetate, Decyl N,N-dimethylamino isopropionate, Diethyleneglycol oleate, Diethyl sebacate, Diethyl succinate, Diisopropyl sebacate, Dodecyl N,N-dimethylamino acetate, Dodecyl (N,N-dimethylamino)-butyrate, Dodecyl N,N-dimethylamino isopropionate, Dodecyl 2-(dimethylamino) propionate, EO-5-oleyl ester, Ethyl acetate, Ethylaceto acetate, Ethyl propionate, Glycerol monoethers, Glycerol monolaurate, Glycerol monooleate, Glycerol monolinoleate, Isopropyl isostearate, Isopropyl linoleate, Isopropyl myristate, Isopropyl myristate/fatty acid monoglyceride combination, Isopropyl myristate/ethanol/L-lactic acid (87:10:3) combination, Isopropyl palmitate, Methyl acetate, Methyl caprate, Methyl laurate, Methyl propionate, Methyl valerate, 1-Monocaproyl glycerol, Monoglycerides (medium chain length), Nicotinic esters (benzyl), Octyl acetate, Octyl N,N-dimethylamino acetate, Oleyl oleate, n-Pentyl N-acetylprolinate, Propylene glycol monolaurate, Sorbitan dilaurate, Sorbitan dioleate, Sorbitan monolaurate, Sorbitan monooleates, Sorbitan trilaurate, Sorbitan trioleate, Sucrose coconut fatty ester mixtures, Sucrose monolaurate, Sucrose monooleate, and Tetradecyl N,N-dimethylamino acetate; Fatty acids such as Alkanoic acids, Capric acid, Diacid, Ethyloctadecanoic acid, Hexanoic acid, Lactic acid, Lauric acid, Linoelaidic acid, Linoleic acid, Linolenic acid, Neodecanoic acid, Oleic acid, Palmitic acid, Pelargonic acid, Propionic acid, and Vaccenic acid; Fatty alcohol ethers such as α-Monoglyceryl ether, EO-2-oleyl ether, EO-5-oleyl ether, EO-10-oleyl ether, and Ether derivatives of polyglycerols and alcohols (1-O-dodecyl-3-O-methyl-2-O-(2',3'-dihydroxypropyl) glycerol); Biologics such as L-α-amino-acids, Lecithin, Phospholipids, Saponin/phospholipids, Sodium deoxycholate, Sodium taurocholate, and Sodium tauroglycocholate; Enzymes such as Acid phosphatase, Calonase, Orgelase, Papain, Phospholipase A-2, Phospholipase C, and Triacylglycerol hydrolase; Amines and Amides such as Acetamide derivatives, Acyclic amides, N-Adamantyl n-alkanamides, Clofibric acid amides, N,N-Didodecyl acetamide, Di-2-ethylhexylamine, Diethyl methyl benzamide, N,N-Diethyl-m-toluamide, N,N-Dimethyl-m-toluarnide, Ethomeen S12 [bis-(2-hydroxyethyl) oleylamine], Hexamethylene lauramide, Lauryl-amine (dodecylamine), Octyl amide, Oleylamine, Unsaturated cyclic ureas, and Urea; Complexing Agents such as, β- and γ-cyclodextrin complexes, Hydroxypropyl methylcellulose, Liposomes, Naphthalene diamide diimide, and Naphthalene diester diimide; Macrocyclics such as Macrocyclic lactones, ketones, and anhydrides (optimum ring-16), and Unsaturated cyclic ureas; Classical surfactants such as Brij 30, Brij 35, Brij 36T, Brij 52, Brij 56, Brij 58, Brij 72, Brij 76, Brij 78, Brij 92, Brij 96, Brij 98, Cetyl trimethyl ammonium bromide, Empicol ML26/F, HCO-60 surfactant, Hydroxypolyethoxydodecane, Ionic surfactants (ROONa, $ROSO_3Na$, $RNH_3Cl$, R=8-16), Lauroyl sarcosine, Nonionic surface active agents, Nonoxynol, Octoxynol, Phenylsulfonate CA, Pluronic F68, Pluronic F 127, Pluronic L62, Polyoleates (nonionic surfactants), Rewopal HV 10, Sodium laurate, Sodium Lauryl sulfate (sodium dodecyl sulfate), Sodium oleate, Sorbitan dilaurate, Sorbitan dioleate, Sorbitan monolaurate, Sorbitan monooleates, Sorbitan trilaurate, Sorbitan trioleate, Span 20, Span 40, Span 85, Synperonic NP, Triton X-100, Tween 20, Tween 40, Tween 60, Tween 80, and Tween 85; N-methyl pyrrolidone and related compounds such as N-Cyclohexyl-2-pyrrolidone, 1-Butyl-3-dodecyl-2-pyrrolidone, 1,3-Dimethyl-2-imidazolikinone, 1,5 Dimethyl-2-pyrrolidone, 4,4-Dimethyl-2-undecyl-2-oxazoline, 1-Ethyl-2-pyrrolidone, 1-Methyl-2-pyrrolidone, 1-Hexyl-4-methyloxycarbonyl-2-pyrrolidone, 1-Hexyl-2-pyrrolidone, 1-(2-Hydroxyethyl) pyrrolidinone, 3-Hydroxy-N-methyl-2-pyrrolidinone, 1-Isopropyl-2-undecyl-2-imidazoline, 1-Lauryl-4-methyloxycarbonyl-2-pyrrolidone, N-Methyl-2-pyrrolidone, Poly(N-vinylpyrrolidone), Pyroglutamic acid esters, and 2-Pyrrolidone (2-pyrrolidinone); Ionic compounds such as Ascorbate, Amphoteric cations and anions, Calcium thioglycolate, Cetyl trimethyl ammonium bromide, 3,5-Diiodosalicylate sodium, Lauroylcholine iodide, 5-Methoxysalicylate sodium, Monoalkyl phosphates, 2-PAM chloride, 4-PAM chloride (derivatives of N-methyl picolinium chloride), Sodium carboxylate, and Sodium hyaluronate; Dimethyl sulfoxide and related compounds such as Cyclic sulfoxides, Decylmethyl sulfoxide, N-Decyl methyl sulfoxide, Dimethyl sulfoxide (DMSO), and 2-Hydroxyundecyl methyl sulfoxide; Solvents and related compounds such as Acetone, n-Alkanes (chain length between 7 and 16), Cyclohexyl-1,1-dimethylethanol, Dimethylacetamide, Dimethyl formamide, Ethanol, Ethanol/d-limonene combination, 2-Ethyl-1,3-hexanediol, Ethoxydiglycol (TRANSCUTOL), Glycerol, Glycols, Lauryl chloride, Limonene, N-Methylformamide, 2-Phenylethanol, 3-Phenyl-1-propanol, 3-Phenyl-2-propen-1-ol, Polyethylene glycol, Polyoxyethylene sorbitan monoesters, Polypropylene glycol, Primary alcohols (tridecanol), Propylene glycol, Squalene, Triacetin, Trichloroethanol, Trifluoroethanol, Trimethylene glycol, and Xylene; Azone and related compounds such as N-Acylhexahydro-2-oxo-1H-azepines, N-Alkyl-dihydro-1,4-oxazepine-5,7-diones, N-Alkylmorpholine-2,3-diones, N-Alkylmorpholine-3,5-diones, Azacycloalkane derivatives (-ketone, -thione), Azacycloalkenone derivatives, 1-[2-(Decylthio)ethyl]azacyclopentan-2-one (HPE-101), N-(2,2-Dihydroxyethyl)dodecylamine, 1-Dodecanoylhexahydro-1-H-azepine, 1-Dodecyl azacycloheptan-2-one (AZONE or Laurocapram), N-Dodecyl diethanolamine, N-Dodecyl-hexahydro-2-thio-1H-azepine, N-Dodecyl-N-(2-methoxyethyl)acetamide, N-Dodecyl-N-(2-methoxyethyl) isobutyramide, N-Dodecyl-piperidine-2-thione, N-Dodecyl-2-piperidinone, N-Dodecyl pyrrolidine-3,5-dione, N-Dodecyl pyrrolidine-2-thione, N-Dodecyl-2-pyrrolidone, 1-Famesylazacycloheptan-2-one, 1-Farnesylazacyclopentan-2-one, 1-Geranylazacycloheptan-2-one, 1-Geranylazacyclopentan-2-one, Hexahydro-2-oxo-azepine-1-acetic acid esters, N-(2-Hydroxyethyl)-2-pyrrolidone, 1-Laurylazacycloheptane, 2-(1-Nonyl)-1,3-dioxolane, 1-N-Octylazacyclopentan-2-one, N-(1-Oxododecyl)-hexahydro-1H-azepine, N-(1-Oxododecyl)-morpholines, 1-Oxohydrocarbyl-substituted azacyclohexanes, N-(1-Oxotetradecyl)-hexahydro-2-oxo-1H-azepine, and N-(1-Thiododecyl)-morpholines; and others such as Aliphatic thiols, Alkyl N,N-dialkyl-substituted amino acetates, Anise oil, Anticholinergic agent pretreatment, Ascaridole, Biphasic group derivatives, Bisabolol, Cardamom oil, 1-Carvone, Chenopodium (70% ascaridole), Chenopodium oil, 1,8 Cineole (eucalyptol), Cod liver oil (fatty acid extract), 4-Decyloxazolidin-2-one, Dicyclohexylmethylamine oxide, Diethyl hexadecylphosphonate, Diethyl hexadecylphosphoramidate, N,N-Dimethyl dodecylamine-N-oxide, 4, 4-Dimethyl-2-undecyl-2-oxazoline, N-Dodecanoyl-L-amino acid methyl esters, 1,3-Dioxacycloalkanes (SEPAs), Dithiothreitol, Eucalyptol (cineole), Eucalyptus oil, Eugenol, Herbal extracts, Lactam N-acetic acid esters, N-Hydroxyethalaceamide, N-Hydroxyethylacetamide, 2-Hydroxy-3-oleoyloxy-1-pyroglutamyloxypropane, Menthol, Menthone, Morpholine derivatives, N-Oxide, Nerolidol, Octyl-β-D-(thio)glucopyranosides, Oxazolidinones, Piperazine derivatives, Polar lipids, Polydimethylsiloxanes, Poly [2-(methylsulfinyl)ethyl acrylate], Polyrotaxanes, Polyvinylbenzyldimethylalkylammonium chloride, Poly(N-vinyl-N-methyl acetamide), Sodium pyroglutaminate, Terpenes and azacyclo ring compounds, Vitamin E (α-tocopherol), Vitamin E TPGS, and Ylang-ylang oil. Additional examples of penetration enhancers not listed above can be found in "Handbook of Pharmaceutical Excipients", Fifth edition, and include glycofurol, lanolin, light mineral oil, myristic acid, polyoxyethylene alky ethers, and thymol. Other examples of penetration enhancers include ethanolamine, diethanolamine, triethanolamine, diethylene glycol, monoethyl ether, citric acid, succinic acid, borage oil, tetrahydropiperine (THP), methanol, ethanol, propanol, octanol, benzyl alcohol, myristyl alcohol, cetyl alcohol, stearyl alcohol, and polyethylene glycol monolaurate.

Although the hydrophobic compositions of the invention can further comprise alcohols, it is not necessary for the compositions to contain alcohols, $C_1$-$C_4$ aliphatic alcohols, or $C_1$-$C_5$ aliphatic alcohols. In some aspects of the invention, the compositions are free of/do not include or contain $C_1$-$C_4$ aliphatic alcohols, or $C_1$-$C_5$ aliphatic alcohols.

Although the hydrophobic compositions of the invention can further comprise additional volatile solvents, it is not necessary for the hydrophobic compositions to contain additional volatile solvents. Volatile solvents are also known as "fugitive" solvents. Non-limiting examples of volatile solvents include volatile alcohols, such as $C_1$ to $C_4$ aliphatic alcohols; and volatile $C_1$ to $C_4$ aliphatic ketones, such as acetone. In some aspects of the inventions, the compositions are free of/do not include or contain volatile $C_1$ to $C_4$ aliphatic ketones. In some aspects of the inventions, the compositions are free of/do not include or contain volatile $C_1$ to $C_4$ aliphatic alcohols.

Although the hydrophobic compositions of the invention can further comprise surfactants, it is not necessary for the hydrophobic compositions to contain surfactants. The term "surfactant" or "surface active agent" means a compound or material or substance that exhibits the ability to lower the surface tension of water or to reduce the interfacial tension between two immiscible substances and includes anionic, cationic, nonionic, amphoteric, and/or phospholipid surfactants. Non-limiting examples of surfactants can be found in McCutcheon's Emulsifiers & Detergents, 2001 North American Edition herein incorporated by reference and also in the International Cosmetic Ingredient Dictionary and Handbook (INCI), 12th Edition, 2008, herein incorporated by reference. Such examples include, but are not limited to, the following: block polymers, e.g., Poloxamer 124; ethoxylated alcohols e.g., Ceteth-2, Ceteareth-20, Laureth-3; ethoxylated fatty esters and oils, e.g., PEG-40 Hydrogenated Castor Oil, PEG-36 Castor Oil, PEG-150 Distearate; glycerol esters, e.g., Polyglyceryl-3 Diisostearate, Glyceryl Stearate; glycol esters, PEG-12 Dioleate, LEXEMUL P; phosphate esters, e.g., Cetyl Phosphate; polymeric surfactants, e.g., PVM/MA Copolymer, Acrylates/C10-30 Alkyl Acrylate Crosspolymer; quaternary surfactants, e.g., Cetrimonium Chloride; Silicone Based Surfactants, e.g., PEG/PPG-20/6 Dimethicone; Sorbitan Derivatives, e.g., Sorbitan Stearate, Polysorbate 80; sucrose and glucose esters and derivatives, e.g., PEG-20 Methyl Glucose Sesquistearate; and sulfates of alcohols, e.g., Sodium Lauryl Sulfate. More generally, surfactants can be classified by their ionic type such as anionic, cationic, nonionic, or amphoteric. They can also be classified by their chemical structures, such as block polymers, ethoxylated alcohols, ethoxylated fatty esters and oils, glycerol esters, glycol esters, phosphate esters, polymeric surfactants, quaternary surfactants, silicone-based surfactants, sorbitan derivatives, sucrose and glucose esters and derivatives, and sulfates of alcohols.

F. Manufacture

The compositions of the invention may be manufactured by methods and equipment known in the art for manufacture of pharmaceutical products including topical, injectable, and oral liquid products. Such methods include, but are not limited to the use of mechanical mixers, dissolvers, dispersers, homogenizers, and mills. Non-limiting examples include LIGHTNIN propeller mixers, COWLES dissolvers, IKA ULTRA TURRAX dispersers, SILVERSON homogenizers, LEE counter-rotating side-scraping mixers, in-line and in-tank rotor-stator homogenizers, 3-roll mills, ointment mills, and rotor-stator mills. "All-in-one" vacuum mixing systems that have a rotating side-scraping mixer plus an in-tank homogenizer may also be used. Such mixers include, but are not limited to OLSA mixers, FRYMA-KORUMA mixers, and LEE TRI-MIX TURBO-SHEAR kettles. The compositions of the invention can be manufactured from small laboratory scale batches using laboratory mixing equipment to full-scale production batches.

II. Enhanced Topical Delivery Methods

In one aspect of the invention, there is disclosed a method for enhancing penetration of taxane nanoparticles into cervical intraepithelial neoplasia (CIN) or cervical cancer of a subject, the method comprising applying to the affected area of the CIN or cervical cancer the topical compositions disclosed herein. In a preferred embodiment, the method comprises applying to the affected area of the CIN or cervical cancer a hydrophobic composition which comprises a hydrophobic carrier, one or more volatile silicone fluids, and a plurality of taxane nanoparticles. In some embodiments, the taxane nanoparticles are paclitaxel nanoparticles, docetaxel nanoparticles, or cabazitaxel nanoparticles. In some embodiments, the taxane nanoparticles, including paclitaxel nanoparticles, docetaxel nanoparticles, or cabazitaxel nanoparticles, have a mean particle size (number) of from 0.01 microns to 1.5 microns, or from 0.01 microns to 1.2 microns, or from 0.01 microns to 1 micron, or from 0.01 microns to less than 1 micron, or from 0.01 microns to 0.9 microns, or from 0.01 microns to 0.8 microns, or from 0.01 microns to 0.7 microns, or from 0.1 microns to 1.5 microns, or from 0.1 microns to 1.2 microns, or from 0.1 microns to 1 micron, or from 0.1 microns to less than 1 micron, or from 0.1 microns to 0.9 microns, or from 0.1 microns to 0.8 microns, or from 0.1 to 0.7 microns, or from 0.2 microns to 1.5 microns, or from 0.2 microns to 1.2 microns, or from 0.2 microns to 1 micron, or from 0.2 microns to less than 1 micron, or from 0.2 microns to 0.9 microns, or from 0.2 microns to 0.8 microns, or from 0.2 microns to 0.7 microns, or from 0.3 microns to 1.5 microns, or from 0.3 microns to 1.2 microns, or from 0.3 microns to 1 micron, or from 0.3 microns to less than 1 micron, or from 0.3 microns to 0.9 microns, or from 0.3 microns to 0.8 microns, or from 0.3 microns to 0.7 microns, or from 0.4 microns to 1.5 microns, or from 0.4 microns to 1.2 microns, or from 0.4 microns to 1 micron, or from 0.4 microns to less than 1 micron, or from 0.4 microns to 0.9 microns, or from 0.4 microns to 0.8 microns, or from 0.4 microns to 0.7 microns, or from 0.5 microns to 1.5 microns, or from 0.5 microns to 1.2 microns, or from 0.5 microns to 1 micron, or from 0.5 microns to less than 1 micron, or from 0.5 microns to 0.9 microns, or from 0.5 microns to 0.8 microns, or form 0.5 microns to 0.7 microns, or from 0.6 microns to 1.5 microns, or from 0.6 microns to 1.2 microns, or from 0.6 microns to 1 micron, or from 0.6 microns to less than 1 micron, or from 0.6 microns to 0.9 microns, or from 0.6 microns to 0.8 microns, or from 0.6 microns to 0.7 microns. In other embodiments, the taxane nanoparticles are paclitaxel nanoparticles. In some embodiments, the paclitaxel nanoparticles have an SSA of at least 18, at least 19, at least 20, at least 21, at least 22, at least 23, at least 24, at least 25, at least 26, at least 27, at least 28, at least 29, at least 30, at least 31, at least 32, at least 33, at least 34, or at least 35 $m^2/g$. In other embodiments, the paclitaxel nanoparticles have an SSA of 18 $m^2/g$ to 50 $m^2/g$, or 20 $m^2/g$ to 50 $m^2/g$, or 22 $m^2/g$ to 50 $m^2/g$, or 25 $m^2/g$ to 50 $m^2/g$, or 30 $m^2/g$ to 50 $m^2/g$, or 18 $m^2/g$ to 45 $m^2/g$, or 20 $m^2/g$ to 45 $m^2/g$, or 22 $m^2/g$ to 45 $m^2/g$, or 25 $m^2/g$ to 45 $m^2/g$, or 30 $m^2/g$ to 45 $m^2/g$, or 18 $m^2/g$ to 40 $m^2/g$, or 20 $m^2/g$ to 40 $m^2/g$, or 22 $m^2/g$ to 40 $m^2/g$, or 25 $m^2/g$ to 40 $m^2/g$, or 30 $m^2/g$ to 40 $m^2/g$. In some embodiments, the paclitaxel nanoparticles have a bulk density (not-tapped) of 0.05 $g/cm^3$ to 0.15 $g/cm^3$, or 0.05 $g/cm^3$ to 0.20 $g/cm^3$. In various embodiments, the hydrophobic carriers are non-polar and/or non-volatile. In some embodiments, the hydrophobic carriers comprise a hydrocarbon. In other embodiments, the hydrophobic carriers comprise petrolatum, mineral oil, and paraffin. In some embodiments, the mineral oil is heavy mineral oil. In some embodiments, the concentration of the volatile silicone fluid in the composition formulation is at an amount effective to enhance skin penetration of the taxane nanoparticles as compared to the formulation without the volatile silicone fluid. A suitable method for measuring penetration into CIN or cervical cancer can be by use of an in vitro Franz diffusion cell (FDC) system using human cadaver skin or other suitable membrane. A suitable in vitro Franz diffusion cell system is described in Example 9 below. In some embodiments, the one or more volatile silicone fluid is at a concentration from 5 to 24% w/w. In other embodiments, the concentration of the one or more volatile silicone fluid is from 5 to 20% w/w. In other embodiments, the one or more volatile silicone fluid is at a concentration of from 5 to 18% w/w. In still other embodiments, the concentration of the one or more volatile silicone fluid is 13% w/w. In various embodiments, the concentration of the one or more volatile silicone fluid can be 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, or 24% w/w or any percentage derivable therein of the total composition weight. In various embodiments, the one or more volatile silicone fluid is cyclomethicone. In other embodiments, the cyclomethicone is cyclopentasiloxane. In some embodiments, the hydrophobic compositions do not contain additional penetration enhancers. In some embodiments, the hydrophobic compositions do not contain laurocapram and/or diethylene glycol monoethyl ether (DGME), and/or isopropyl myristate, and/or alpha tocopherol. In other embodiments, the hydrophobic compositions do not contain additional volatile solvents. In still other embodiments, the hydrophobic compositions do not contain a surfactant. In other embodiments, the hydrophobic compositions are free of/do not include or contain alcohols, or $C_1$ to $C_4$ aliphatic alcohols, or $C_1$ to $C_5$ aliphatic alcohols. In some embodiments, the hydrophobic compositions comprise one or more volatile silicone fluids, but do not contain additional silicone materials. In some embodiments, the compositions do not contain hyaluronic acid, and/or do not contain a conjugate of hyaluronic acid and a taxane, and/or do not contain a conjugate of hyaluronic acid and paclitaxel. In some embodiments, the compositions do not contain a polymer or a biodegradable polymer. In some embodiments, the compositions do not contain a poloxamer, styrene-isobutylene-styrene (SIBS), a polyanhydride copolymer, polycaprolactone, polyethylene glycol, Poly (bis(P-carboxyphenoxy) propane-sebacic acid, and/or poly(D, L lactic-co-glycolic acid. In various embodiments, the taxane can be paclitaxel, docetaxel, or cabazitaxel. In some embodiments, the CIN is CIN 1. In some embodiments, the CIN is CIN 2. In some embodiments, the CIN is CIN 3. In some embodiments, the CIN is CIN 2/3. In some embodiments, the CIN is CIN 2, CIN 3, or CIN 2/3. In some embodiments, the method further comprises placing a cervical cap over the cervix after administration of the composition to the affected area. In other embodiments, the hydrophobic compositions are sterile. In other embodiments, the hydrophobic compositions are non-sterile. In other embodiments, the hydrophobic compositions have a low bioburden. In some embodiments, the hydrophobic compositions are semi-solid compositions. In still other embodiments, the hydrophobic compositions are ointments. In some embodiments, the hydrophobic compositions are semi-solid compositions, including ointments, and have a viscosity of from 12,500 cps to 247,500 cps, or from 25,000 cps to 150,000 cps as measured at room temperature by a Brookfield RV viscometer using a small sample adapter with a SC4-14 spindle and a 6R chamber at 5 rpm with an equilibration time of 2 minutes. An alternative method for performing viscosity measurements of the hydrophobic, semi-solid compositions is using a Brookfield RV viscometer on a helipath stand with the helipath on, with a T-E spindle at 10 RPM at room temperature for 45 seconds. In some embodiments, the hydrophobic compositions are semi-solid compositions, including ointments, and have a viscosity of from 25,000 cps to 500,000 cps, or from 25,000 cps to 400,000 cps, or from 25,000 cps to 350,000 cps, or from 25,000 cps to 300,000 cps, or from 50,000 cps to 500,000 cps, or from 50,000 cps to 400,000 cps, or from 50,000 cps to 350,000 cps, or from 50,000 cps to 300,000 cps, or from 75,000 cps to 500,000 cps, or from 75,000 cps to 400,000 cps, or from 75,000 cps to 350,000 cps, or from 75,000 cps to 300,000 cps, or from 100,000 cps to 500,000 cps, or from 100,000 cps to 400,000 cps, or from 100,000 cps to 350,000 cps, or from 100,000 cps to 300,000 cps using a Brookfield RV viscometer on a helipath stand with the helipath on, with a T-E spindle at 10 RPM at room temperature for 45 seconds. In some embodiments, the hydrophobic compositions are not sprays and are not sprayable.

In another aspect of the inventions, disclosed is a method of enhancing penetration of taxane nanoparticles into a CIN or cervical cancer of a subject, the method comprising topically applying a hydrophobic composition comprising a plurality of taxane nanoparticles to the affected area of the CIN or cervical cancer, wherein the penetration of the taxane nanoparticles from the hydrophobic composition is greater than the penetration of taxane nanoparticles from a suspension of taxane nanoparticles in an aqueous based composition. A suitable method for determining penetration of taxane nanoparticles in CIN or cervical cancer is by an in vitro Franz diffusion cell (FDC) system using human cadaver skin or other suitable membrane. A suitable in vitro Franz diffusion cell system is described in Example 9 below. In some embodiments, the taxane nanoparticles have a mean particle size (number) from 0.1 microns to 1.5 microns. In other embodiments, the taxane nanoparticles have a mean particle size (number) from 0.1 microns to less than 1 micron. In other embodiments, the taxane nanoparticles are paclitaxel nanoparticles, docetaxel nanoparticles, or cabazitaxel nanoparticles. In other embodiments, the hydrophobic composition further comprises a hydrophobic carrier. In some embodiments, the CIN is CIN 1. In some embodiments, the CIN is CIN 2. In some embodiments, the CIN is CIN 3. In some embodiments, the CIN is CIN 2/3. In some embodiments, the CIN is CIN 2, CIN 3, or CIN 2/3. In some embodiments, the method further comprises placing a cervical cap over the cervix after administration of the composition to the affected area.

III. Methods for the Inhibition of Crystal Growth in Formulations

In one aspect of the invention, disclosed are methods of inhibiting the growth of crystalline taxane nanoparticles, the method comprising contacting the taxane nanoparticles with a hydrophobic carrier. In some embodiments, the taxane nanoparticles are paclitaxel nanoparticles, docetaxel nanoparticles, or cabazitaxel nanoparticles. In some embodiments, the taxane nanoparticles are paclitaxel nanoparticles. In other embodiments the composition is anhydrous. In other embodiments, the hydrophobic carriers comprise a hydrocarbon. In other embodiments, the hydrocarbon is petrolatum, mineral oil, or paraffin wax, or mixtures thereof. In some embodiments, the mineral oil is heavy mineral oil. In some embodiments, the compositions further comprises one or more volatile silicone fluids. In other embodiments, the volatile silicone fluid is cyclomethicone. In other embodiments, the cyclomethicone is cyclopentasiloxane.

In another aspect of the invention, disclosed are methods of inhibiting the growth of a dispersion of crystalline taxane nanoparticles in an aqueous based carrier, the method comprising adding poloxamer 407, a quaternary ammonium compound, or a cross-linked acrylic acid polymer to the aqueous based carrier at the time of manufacture. In some embodiments, the additive is poloxamer 407. In various embodiments, the quaternary ammonium compound is the additive and is benzalkonium chloride or benzethonium chloride. In some embodiments, the quaternary ammonium compound is benzalkonium chloride. In some embodiments, the cross-linked acrylic acid polymer is the additive and is Carbomer. In some embodiments, the taxane nanoparticles are paclitaxel nanoparticles, docetaxel nanoparticles, or cabazitaxel nanoparticles.

IV. Topical Treatment Cervical Intraepithelial Neoplasia (CIN) and Cervical Cancer The methods of the invention include methods of treatment of cervical intraepithelial neoplasia (CIN) and/or cervical cancer in a subject/patient by topically administering to the affected area (topical therapy) compositions disclosed herein comprising taxanes, thereby treating the CIN and/or cervical cancer. The "affected area" of CIN or cervical cancer includes the area of the cervical epithelium including the ectocervix, squamocolumnar junction, and/or endocervix where one or more CIN lesions or cervical cancer tumors are detectable by cytologic diagnosis (e.g., Pap smear), colposcopy, and/or histological assessment of a cervical biopsy. The affected area can include areas of the cervical epithelium in the proximity of the one or more lesions likely to contain undetectable preclinical lesions. The composition can be topically applied directly to the cervical epithelium including the ectocervix, squamocolumnar junction, and/or endocervix. In some embodiments, the composition is applied to the ectocervix. In some embodiments, the composition is applied to the squamocolumnar junction. In some embodiments, the composition is applied to the endocervix. In some embodiments, the composition is applied to the ectocervix, squamocolumnar junction, or endocervix, or a combination thereof. The composition can be applied by a medical practitioner or nurse using a gloved hand, spatula, or other means of cervical administration. An appropriately sized cervical cap can be placed over the cervix after administration of the composition to maintain localization of the formulation to the cervix for the treatment period. The cervical cap can be removed at any time during the treatment period to inspect the cervix and then can be re-applied if further treatment is needed or can be permanently removed.

The compositions can be topically administered to CIN that has been histologically assessed (cervical biopsy) as CIN 1, CIN 2, CIN 3, or CIN 2/3, or combinations thereof, using the following criteria:

CIN 1: Mild dysplasia or mild dyskaryosis. Good maturation of cells through the depth of the cervical epithelium, with minimal nuclear abnormalities and few mitotic figures. Undifferentiated cells are confined to the deeper/lower third of the epithelium. Mitotic figures are not very numerous. Cytopathic changes due to HPV infection may be observed in the full thickness of the epithelium.

CIN 2: Moderate dysplasia or moderate dyskaryosis. Dysplastic changes mostly restricted to the lower half or two-thirds of the epithelium, with more marked nuclear abnormalities than CIN 1. Mitotic figures are seen through the lower half of the epithelium.

CIN 3: Severe dysplasia or severe dyskaryosis. Differentiation and stratification may be totally absent or present only in the superficial quarter of the epithelium with numerous mitotic figures. Nuclear abnormalities extend throughout the thickness of the epithelium. Many mitotic figures have abnormal forms.

CIN 2/3: Features of both CIN 2 and CIN 3.

The compositions can be topically administered to CIN that has been given a histological classification (i.e., CIN 1, CIN 2, CIN 3, and/or CIN 2/3) after colposcopic examination using scoring of the modified Reid Colposcopic Index (RCI) (see Table 21 below). The overall RCI score can predictively correlate to a histological diagnosis based on guidelines from the WHO International Agency for Research on Cancer (2017) as follows: A score of 0-2 is likely CIN 1. A score of 3-4 is likely CIN 1 or CIN 2. A score of 5-8 is likely CIN 2 or CIN 3.

The compositions can be topically administered to CIN that has been cytologically assessed as low-grade squamous intraepithelial lesions (LSIL) or high-grade squamous intraepithelial lesions (HSIL).

The compositions can be topically administered to cervical cancer tumors that have been classified as any of the following stages:

Stage I (stage 1 cervical cancer): In stage I cervical cancer, the cancer is confined to the cervix, but has not spread beyond it. This stage is further separated into subcategories:

Stage IA1: There is a very small amount of cancer, less than 3 mm deep (about ⅛-inch) and less than 7 mm wide, that can only be seen under a microscope.

Stage IA2: The cancer is between 3 mm and 5 mm (about ⅕-inch) deep and less than 7 mm (about ¼-inch) wide.

Stage IB1: The cancer can be seen without a microscope, but it is not larger than 4 cm (about 1⅗ inches).

Stage IB2: The cancer can be seen without a microscope and measures greater than 4 cm.

Stage II (stage 2 cervical cancer): Stage II cervical cancer means that the cancer has grown beyond the cervix and uterus but has not reached the walls of the pelvis or the lower part of the vagina. In this stage of cervical cancer, the disease has not spread to lymph nodes or distant sites. Stage II has two additional subcategories:

Stage IIA: The cancer has not spread into the tissues next to the cervix, the parametria, but it may have grown into the upper part of the vagina.

Stage IIB: The cancer has spread into the tissues next to the cervix, the parametria.

Stage III (stage 3 cervical cancer): Stage III cervical cancer means that the cancer has spread to the lower part of the vagina or the walls of the pelvis, but not to distant sites. This stage is separated into two subcategories:

Stage IIIA: The cancer has spread to the lower part of the vagina or the walls of the pelvis. The cancer may be blocking the ureters (tubes that carry urine from the kidneys to the bladder). It may have spread to the lymph nodes.

Stage IIIB: The cancer has grown into the walls of the pelvis and/or has blocked both ureters, but it has not spread to distant sites.

Stage IV (stage 4 cervical cancer): In this cervical cancer stage, the disease has spread to nearby organs or other parts of the body. Stage IV is separated into two subcategories:

Stage IVA: The cancer has spread to the bladder or rectum, but not to distant sites.

Stage IVB: The cancer has spread to organs beyond the pelvis, such as the lungs or liver.

The amount of the hydrophobic composition topically applied to the affected area of the CIN or cervical cancer can vary depending on the size of the affected area/number of CIN lesions or cervical cancer tumors, and the concentration of the paclitaxel in the composition, but generally a quantity of ≤1 ml can be applied.

The dosing of the composition can vary, but generally can include daily or weekly administrations until a therapeutic improvement or elimination of the CIN or cervical cancer is achieved.

In some embodiments, the taxane is paclitaxel. In other embodiments, the taxane is docetaxel or cabazitaxel. In some aspects, the compositions are hydrophobic and can comprise a hydrophobic carrier. In other aspects, the compositions are aqueous based compositions and can comprise an aqueous carrier. In some embodiments, the carrier is anhydrous. In some embodiments, the taxanes are a plurality of taxane nanoparticles. In some embodiments, the plurality of taxane nanoparticles are suspended within the compositions. In other aspects, the taxanes are solubilized in the compositions.

A preferred method for the topical treatment of CIN or cervical cancer in a subject need of treatment comprises topically administering to an affected area of the subject a hydrophobic composition comprising a continuous hydrophobic carrier, one or more volatile silicone fluids, and a plurality of taxane nanoparticles, wherein the taxane nanoparticles are suspended within the composition, wherein the mean particle size (number) of the taxane nanoparticles is from 0.1 microns to 1.5 microns or from 0.1 microns to less than 1 micron, and wherein the concentration of the taxane nanoparticles is at an amount effective to provide a therapeutic improvement (treatment) in the condition of the CIN or cervical cancer. In some embodiments, the taxane nanoparticles are paclitaxel nanoparticles, docetaxel nanoparticles, or cabazitaxel nanoparticles. In some embodiments, the taxane nanoparticles, including paclitaxel nanoparticles, docetaxel nanoparticles, or cabazitaxel nanoparticles, have a mean particle size (number) of from 0.01 microns to 1.5 microns, or from 0.01 microns to 1.2 microns, or from 0.01 microns to 1 micron, or from 0.01 microns to less than 1 micron, or from 0.01 microns to 0.9 microns, or from 0.01 microns to 0.8 microns, or from 0.01 microns to 0.7 microns, or from 0.1 microns to 1.5 microns, or from 0.1 microns to 1.2 microns, or from 0.1 microns to 1 micron, or from 0.1 microns to less than 1 micron, or from 0.1 microns to 0.9 microns, or from 0.1 microns to 0.8 microns, or from 0.1 to 0.7 microns, or from 0.2 microns to 1.5 microns, or from 0.2 microns to 1.2 microns, or from 0.2 microns to 1 micron, or from 0.2 microns to less than 1 micron, or from 0.2 microns to 0.9 microns, or from 0.2 microns to 0.8 microns, or from 0.2 microns to 0.7 microns, or from 0.3 microns to 1.5 microns, or from 0.3 microns to 1.2 microns, or from 0.3 microns to 1 micron, or from 0.3 microns to less than 1 micron, or from 0.3 microns to 0.9 microns, or from 0.3 microns to 0.8 microns, or from 0.3 microns to 0.7 microns, or from 0.4 microns to 1.5 microns, or from 0.4 microns to 1.2 microns, or from 0.4 microns to 1 micron, or from 0.4 microns to less than 1 micron, or from 0.4 microns to 0.9 microns, or from 0.4 microns to 0.8 microns, or from 0.4 microns to 0.7 microns, or from 0.5 microns to 1.5 microns, or from 0.5 microns to 1.2 microns, or from 0.5 microns to 1 micron, or from 0.5 microns to less than 1 micron, or from 0.5 microns to 0.9 microns, or from 0.5 microns to 0.8 microns, or form 0.5 microns to 0.7 microns, or from 0.6 microns to 1.5 microns, or from 0.6 microns to 1.2 microns, or from 0.6 microns to 1 micron, or from 0.6 microns to less than 1 micron, or from 0.6 microns to 0.9 microns, or from 0.6 microns to 0.8 microns, or from 0.6 microns to 0.7 microns. In other embodiments, the taxane nanoparticles are paclitaxel nanoparticles. In some embodiments, the paclitaxel nanoparticles have an SSA of at least 18, at least 19, at least 20, at least 21, at least 22, at least 23, at least 24, at least 25, at least 26, at least 27, at least 28, at least 29, at least 30, at least 31, at least 32, at least 33, at least 34, or at least 35 $m^2/g$. In other embodiments, the paclitaxel nanoparticles have an SSA of 18 $m^2/g$ to 50 $m^2/g$, or 20 $m^2/g$ to 50 $m^2/g$, or 22 $m^2/g$ to 50 $m^2/g$, or 25 $m^2/g$ to 50 $m^2/g$, or 30 $m^2/g$ to 50 $m^2/g$, or 18 $m^2/g$ to 45 $m^2/g$, or 20 $m^2/g$ to 45 $m^2/g$, or 22 $m^2/g$ to 45 $m^2/g$, or 25 $m^2/g$ to 45 $m^2/g$, or 30 $m^2/g$ to 45 $m^2/g$, or 18 $m^2/g$ to 40 $m^2/g$, or 20 $m^2/g$ to 40 $m^2/g$, or 22 $m^2/g$ to 40 $m^2/g$, or 25 $m^2/g$ to 40 $m^2/g$, or 30 $m^2/g$ to 40 $m^2/g$. In some embodiments, the paclitaxel nanoparticles have a bulk density (not-tapped) of 0.05 $g/cm^3$ to 0.15 $g/cm^3$, or 0.05 $g/cm^3$ to 0.20 $g/cm^3$. In various embodiments, the hydrophobic carriers are nonpolar and/or non-volatile. In some embodiments, the hydrophobic carriers comprise a hydrocarbon. In other embodiments, the hydrophobic carriers comprise petrolatum, mineral oil, and paraffin. In some embodiments, the mineral oil is heavy mineral oil. In some embodiments, the volatile silicone fluid is at a concentration of from 5 to 24% w/w. In other embodiments, the volatile silicone fluid is at a concentration of from 5 to 20% w/w. In other embodiments, the volatile silicone fluid is at a concentration of from 5 to 18% w/w. In other embodiments, the concentration of the volatile silicone fluid is 13% w/w. In some embodiments, the volatile silicone fluid is cyclomethicone. In other embodiments, the cyclomethicone is cyclopentasiloxane. In various embodiments, the hydrophobic compositions are free of/do not include or contain additional penetration enhancers. In some embodiments, the hydrophobic compositions are free of/do not include or contain laurocapram, and/or diethylene glycol monoethyl ether (DGME), and/or isopropyl myristate, and/or alpha tocopherol. In other embodiments, the hydrophobic compositions are free of/do not include or contain additional volatile solvents. In other embodiments, the hydrophobic compositions are free of/do not include or contain a surfactant. In other embodiments, the hydrophobic compositions are free of/do not include or contain alcohols, $C_1$-$C_4$ aliphatic alcohols, or $C_1$ to $C_5$ aliphatic alcohols. In some embodiments, the hydrophobic compositions comprise one or more volatile silicone fluids, but do not contain additional silicone materials. In some embodiments, the hydrophobic compositions are free of/do not include hyaluronic acid; and/or are free of/do not include a conjugate of hyaluronic acid and a taxane; and/or are free of/do not include a conjugate of hyaluronic acid and paclitaxel; and/or are free of/do not include a polymer or a biodegradeable polymer; and/or are free of/do not include a poloxamer, styrene-isobutylene-styrene (SIBS), a polyanhydride copolymer, polycaprolactone, polyethylene glycol, Poly (bis(P-carboxyphenoxy)propane-sebacic acid, and/or poly(D, L lactic-co-glycolic acid) (PLGA).

The concentration of the taxane nanoparticles is at an amount effective to treat the CIN or cervical cancer. Treatment of CIN provides a therapeutic improvement (treatment) in the condition of the CIN. This improvement can be indicated by one or more of the following scenarios: (a) a lowering of the histological grade as determined by histological assessment of a cervical biopsy; (b) a lowering of the cytological grade as determined by a cytological diagnosis; (c) a lowering of the modified Reid Colposcopic Index (RCI) score as determined by colposcopic examination; (d) a reduction in size of the CIN lesion(s), measured as a reduction of the longest diameter of the lesion, or sum of longest diameters of the lesions; (e) complete elimination of the CIN lesion(s); (f) a reduction or elimination of pain. Treatment of cervical cancer provides one or more of the following: (a) reducing a cervical cancer tumor size; (b) reducing a cervical cancer tumor growth; (c) reducing or limiting development and/or spreading of metastases, or eliminating metastases; (d) eliminating a cervical cancer tumor; (e) reducing or eliminating pain.

The concentration of the taxane nanoparticles can be from 0.05 to 10% w/w, or the concentration of the taxane nanoparticles can be from 0.05 to 5% w/w, or the concentration of the taxane nanoparticles can be from 0.1 to 5% w/w, or the concentration of the taxane nanoparticles can be 0.05, 0.1, 0.15, 0.2, 0.25, 0.3, 0.4, 0.5, 0.6, 0.7, 0.75, 0.8, 0.9, 1.0, 1.1, 1.2, 1.25, 1.3, 1.4, 1.5, 1.6, 1.7, 1.75, 1.8, 1.9, 2.0, 2.1, 2.2, 2.25, 2.3, 2.4, 2.5, 2.6, 2.7, 2.75, 2.8, 2.9, 3.0, 3.1, 3.2, 3.25, 3.3, 3.4, 3.5, 3.6, 3.7, 3.75, 3.8, 3.9, 4.0, 4.1, 4.2, 4.25, 4.3, 4.4, 4.5, 4.6, 4.7, 4.75, 4.8, 4.9, 5, 6, 7, 8, 9, or 10% w/w or any percentage derivable therein of the total composition weight. In some embodiments, the taxane nanoparticles are paclitaxel nanoparticles, docetaxel nanoparticles, or cabazitaxel nanoparticles. In other embodiments, the taxane nanoparticles are paclitaxel nanoparticles. In some embodiments, the paclitaxel nanoparticles are at a concentration of about 0.05 to less than 3% w/w, or about 0.05 to about 2% w/w, or about 0.05 to about 1% w/w, or about 0.05 to about 0.3% w/w, or about 0.05 to about 0.2% w/w, or about 0.05 to about 0.15% w/w, or about 0.1 to about 2% w/w, or about 0.1 to about 1% w/w, or about 0.1 to about 0.3% w/w, or about 0.1 to about 0.2% w/w, or about 0.15 to about 2% w/w, or about 0.15 to about 1% w/w, or about 0.15 to about 0.3% w/w, or about 0.3 to about 2% w/w, or about 0.3 to about 1% w/w, or about 1 to about 2% w/w, or about 0.2 to about 0.4% w/w, or about 0.5 to about 1.5% w/w, or about 1.5 to about 2.5% w/w in the compositions. In other embodiments, the concentration of the paclitaxel nanoparticles is 80 to 120% of 1% w/w (i.e., 0.8 to 1.2% w/w), or 80 to 120% of 0.05% w/w, or 80 to 120% of 0.1% w/w, or 80 to 120% of 0.15% w/w, or 80 to 120% of 0.2% w/w, or 80 to 120% of 0.25% w/w, or 80 to 120% of 0.3% w/w, or 80 to 120% of 0.35% w/w, or 80 to 120% of 0.4% w/w, or 80 to 120% of 0.45% w/w, or 80 to 120% of 0.5% w/w, or 80 to 120% of 0.55% w/w, or 80 to 120% of 0.6% w/w, or 80 to 120% of 0.65% w/w, or 80 to 120% of 0.7% w/w, or 80 to 120% of 0.75% w/w, or 80 to 120% of 0.8% w/w, or 80 to 120% of 0.85% w/w, or 80 to 120% of 0.9% w/w, or 80 to 120% of 0.95% w/w, or 80 to 120% of 1.5% w/w, or 80 to 120% of 2% w/w, or 80 to 120% of 2.5% w/w.

In some embodiments, the hydrophobic compositions are sterile. In other embodiments, the hydrophobic compositions are non-sterile. In other embodiments, the hydrophobic compositions have a low bioburden. In other embodiments, the hydrophobic compositions are anhydrous. In some embodiments, the hydrophobic compositions are semi-solid compositions. In still other embodiments, the hydrophobic compositions are ointments. In some embodiments, the hydrophobic compositions are semi-solid compositions, including ointments, and have a viscosity of from 12,500 cps to 247,500 cps, or from 25,000 cps to 150,000 cps as measured at room temperature by a Brookfield RV viscometer using a small sample adapter with a SC4-14 spindle and a 6R chamber at 5 rpm with an equilibration time of 2 minutes. The compositions can be spreadable or flowable when being applied to an affected area. An alternative method for performing viscosity measurements of the hydrophobic, semi-solid compositions is using a Brookfield RV viscometer on a helipath stand with the helipath on, with a T-E spindle at 10 RPM at room temperature for 45 seconds. In some embodiments, the hydrophobic compositions are semi-solid compositions, including ointments, and have a viscosity of from 25,000 cps to 500,000 cps, or from 25,000 cps to 400,000 cps, or from 25,000 cps to 350,000 cps, or from 25,000 cps to 300,000 cps, or from 50,000 cps to 500,000 cps, or from 50,000 cps to 400,000 cps, or from 50,000 cps to 350,000 cps, or from 50,000 cps to 300,000 cps, or from 75,000 cps to 500,000 cps, or from 75,000 cps to 400,000 cps, or from 75,000 cps to 350,000 cps, or from 75,000 cps to 300,000 cps, or from 100,000 cps to 500,000 cps, or from 100,000 cps to 400,000 cps, or from 100,000 cps to 350,000 cps, or from 100,000 cps to 300,000 cps using a Brookfield RV viscometer on a helipath stand with the helipath on, with a T-E spindle at 10 RPM at room temperature for 45 seconds. In some embodiments, the hydrophobic compositions are not sprays and are not sprayable. In some embodiments, the compositions are not dry powders. In some embodiments, the compositions do not solely include the taxane nanoparticles.

EXAMPLES

The present invention will be described in greater detail by way of specific examples. The following examples are offered for illustrative purposes only, and are not intended to limit the invention in any manner. Those of skill in the art will readily recognize a variety of noncritical parameters, which can be changed or modified to yield essentially the same results.

Example 1—Solubility of Paclitaxel in Various Solvents

The solubility of paclitaxel was determined in various solvents by the following method: (a) for each solvent, about 2 g of the solvent was weighed into a clear glass vial, (b) approximately 0.1 g of paclitaxel was added to each vial, (c) each vial was mixed with a stir bar on a magnetic stirrer for 2 hours at room temperature, (d) each vial was then checked every 1-2 hours to see if the solution became clear. If yes, an additional approximately 0.1 g of paclitaxel was added to the vial and mixing was continued. Step "d" was continued for each vial for a total of 48 hours.

The solution from each vial was measured for paclitaxel concentration using an HPLC method based on Agilent Technical Application Note for Paclitaxel "Analysis of Taxol by HPLC", 2002, and modified to use a 227 nm detection wavelength, rather than 204 nm (the 227 nm wavelength is used in the USP paclitaxel monograph, and reduces the solvent effects seen at lower wavelengths).

The solubility values are shown in Table 1.

TABLE 1

| Solvent | Paclitaxel Solubility at RT |
| --- | --- |
| Hexylene Glycol | 4.07% w/w |
| Diethylene Glycol Monoethyl Ether, NF (TRANSCUTOL P) | 33.10% w/w |
| Propylene Carbonate | 4.74% w/w |
| Super Refined Oleic Acid, NF | 0.041% w/w |
| Super Refined Oleyl Alcohol, NF | 0.38% w/w |
| Diisopropyl Adipate (CERAPHYL 230) | 3.51% w/w |
| Medium Chain Triglycerides, NF | 0.32% w/w |
| Propylene Glycol, USP | 0.88% w/w |
| Polyethylene Glycol 400, NF | 22.30% w/w |
| Benzyl Alcohol, NF | 17.02% w/w |
| Isopropyl Myristate, NF | 0.048% w/w |
| Mineral Oil, USP (heavy) | 0.3 ppm |
| Dimethyl Isosorbide | 38.22% w/w |
| Purified Water, USP | |

Example 2 Observations of Paclitaxel Nanoparticle Crystals in Various Substances and Solutions of Substances Paclitaxel nanoparticles were dispersed in various substances and aqueous solutions of substances and observed for crystal growth. The results are shown in Table 2.

TABLE 2

| Substance | Concentration | Visual observation by light microscopy- Needle shaped crystals observed? |
| --- | --- | --- |
| Aqueous Based Carriers | | |
| Purified Water | 100% | Yes, >5 μm, @ 5 days, RT & 60 C. |
| Polysorbate 80 | 0.5% in water | Yes, <5 μm @ 22 days, RT & 60 C. |
| PEG 400 | 10% in water | Yes, >5 μm @ 22 days, RT & 60 C. |
| Benzalkonium chloride (50%) | 2% in water | No, <5 μm @ 7 days & 21 days, RT |
| Magnesium nitrate | 5% in water | Yes, >5 μm, @ 3 days, RT |
| Mannitol | 5% in water | Yes, >5 μm, @ 7 days, RT |
| Sorbitol | 5% in water | Yes, >5 μm, @ 7 days, RT |
| Povidone | 1% in water | Yes, <5 μm, @ 7 days & 21 days, RT |
| Lecithin | 1% in water | Yes, >10 μm, @ 24 hrs, RT |
| Sodium lauryl sulfate | 2% in water | Yes, >5 μm, @ 7 days, RT |
| Ammonium lauryl sulfate | 2% in water | Yes, >5 μm, @ 3 days, RT |
| Aluminum sulfate | 0.1-0.2% in water | Yes, >5 μm, @ 7 days, RT |
| Sodium phosphate monobasic | 0.75% in water | Yes, >5 μm, @ 7 days, RT |
| Zinc acetate | 1.2% in water | Yes, >5 μm, @ 7 days, RT |
| Proline | 3% in water | Yes, >5 μm, @ 7 days, RT |
| Hydroxyethyl cellulose | 1% in water | Yes, >5 μm, @ 7 days, RT |
| CARBOPOL ULTREZ 10 (with Ammonium hydroxide as neutralizer) | 0.5% in water | No, <5 μm, @ 8 days & 21 days, RT |
| Hydroxypropyl methylcellulose | 1% in water | Yes, >5 μm @ 3 days, RT |
| Saline | 0.9% NaCl in water | Yes, >10 μm, @ 7 days , RT & 60 C. |
| Polysorbate 80 | 0.5% in Saline | Yes, >5 μm @ 7 days, RT & 60 C. |
| Poloxamer 407 | 2% in water | No, <5 μm @ 5 & 7 days, RT |
| Poloxamer 188 | 2% in water | Yes, >5 μm @ 7 days, RT |

TABLE 2-continued

| Substance | Concentration | Visual observation by light microscopy- Needle shaped crystals observed? |
|---|---|---|
| Polyoxyl 40 Hydrogenated Castor Oil (KOLLIPHOR RH40) | 1% in water | Yes, <5 μm @ 6 days, RT |
| Vitamin E TPGS | 0.5% in water | Yes, <5 μm @ 6 days, RT |
| Hydrophobic Carriers | | |
| Mineral Oil USP (heavy) | 100% | No, <5 μm @ 3 days, RT & 40 C. |
| Light Mineral Oil NF | 100% | No, <5 μm @ 3 days, RT & 40 C. |
| FOMBLIN HC04 | 100% | No, <5 μm @ 4, 7 & 13 days, RT |
| ST-Cyclomethicone 5 NF | 100% | No, <5 μm @ 24 hrs & 13 days, RT |
| Dimethicone, 1000 cSt | 100% | No, <5 μm @ 24 hrs & 6 days, RT |
| Castor Oil | 100% | No, <5 μm @ 24 hrs & 9 days, RT |

The paclitaxel nanoparticle crystals did not grow in any of the hydrophobic carriers. Also, the nanoparticles did not grow in aqueous solutions of benzalkonium chloride, CARBOPOL ULTREZ 10, or poloxamer 407.

Example 3 Particle Size, SSA, and Bulk Density Analysis of Paclitaxel Nanoparticles The particle size of the paclitaxel nanoparticle lots used in the formulas listed in Table 3 and Tables 16-19 were analyzed by the following particle size method using an ACCUSIZER 780:

Instrument parameters: Max. Concentration: 9000 particles/mL, No. containers: 1, Sensor Range: Summation, Lower Detection Limit: 0.5 μm, Flow Rate: 30 mL/min, No. Analysis pulls: 4, Time between pulls: 1 sec, Pull volume: 10 mL, Tare Volume: 1 mL, Prime volume: 1 mL, Include First Pull: Not Selected.

Sample preparation: Placed a scoop of paclitaxel nanoparticle API into a clean 20 mL vial and added approximately 3 mL of a filtered (0.22 μm) 0.1% w/w solution of SDS to wet the API, then filled the remainder of the vial with the SDS solution. Vortexed for 5-10 minutes and sonicated in a water batch for 1 minute.

Method: Filled a plastic bottle with filtered (0.22 μm) 0.1% w/w SDS solution and analyzed the Background. Pipetted a small amount of the paclitaxel nanoparticles sample suspension, <100 μL, into the bottle of 0.1% w/w SDS solution while stirring; placed the ACCUSIZER inlet tube into the bottle and ran sample through instrument. As necessary, added more SDS solution or paclitaxel sample suspension to reach a desired run concentration of 6000-8000 particle count.

Particles size results (based on number-weighted differential distribution): Paclitaxel nanoparticles lot used in formulas listed in Table 3: Mean: 0.861 μm, Mode: 0.572 μm, Median: 0.710 μm. Paclitaxel nanoparticles lot used in formulas listed in Tables 16-19: Mean: 0.83 μm.

The specific surface area (SSA) of the paclitaxel nanoparticles lots used in the formulas listed in Table 3 and Tables 16-19 were analyzed by the Brunauer-Emmett-Teller ("BET") isotherm method described above. The paclitaxel nanoparticles lot used in the formulas listed in Table 3 had an SSA of 41.24 $m^2/g$. The paclitaxel nanoparticles lot used in the formulas listed in Tables 16-19 had an SSA of 26.72 $m^2/g$.

The bulk density (not-tapped) of the paclitaxel nanoparticles lot used in the formulas listed in Table 3 was 0.05 $g/cm^3$. The bulk density (not-tapped) of the paclitaxel nanoparticles lot used in the formulas listed in Tables 16-19 was 0.09 $g/cm^3$.

Example 4 Anhydrous Hydrophobic Compositions of Paclitaxel Nanoparticles with Hydrophobic Carriers Anhydrous hydrophobic compositions of paclitaxel nanoparticles with hydrophobic carriers are listed in Table 3.

TABLE 3

| Component (% w/w) | Formula Number | | | | | | | | | | | | |
|---|---|---|---|---|---|---|---|---|---|---|---|---|---|
| | F4 | F5 | F6 | F7 | F8 | F9 | F10 | F11 | F12 | F13 | A | B | C |
| Paclitaxel Particles | 1.0 | 1.0 | 1.0 | 1.0 | 0.5 | 2.0 | 1.0 | 1.0 | 1.0 | 1.0 | 0.5 | 0.5 | 0.5 |
| FOMBLIN HC04 | — | — | — | 15.0 | — | — | — | — | — | — | — | — | — |
| Mineral Oil USP | 10.0 | — | 5.0 | — | 5.0 | 5.0 | — | — | — | — | — | — | — |
| ST-Cyclomethicone 5 NF (Dow Corning) | — | 5.0 | 13.0 | — | 13.0 | 13.0 | 13.0 | 13.0 | 18.0 | 15.0 | qs ad 100 | qs ad 100 | qs ad 100 |
| Oleyl Alcohol | — | 5.0 | — | — | — | — | 1.0 | — | — | — | — | 5.0 |
| Isopropyl Myristate NF | — | 5.0 | — | — | — | — | 5.0 | 1.0 | — | 3.0 | — | 35 | 5.0 |

TABLE 3-continued

| Component (% w/w) | F4 | F5 | F6 | F7 | F8 | F9 | F10 | F11 | F12 | F13 | A | B | C |
|---|---|---|---|---|---|---|---|---|---|---|---|---|---|
| Dimethicone | — | — | — | — | — | — | — | — | — | — | 5.0 | 5.0 | 5.0 |
| Fumed Silica | — | — | — | — | — | — | — | — | — | — | 5.5 | 5.5 | 2.8 |
| Cetostearyl Alcohol NF | — | — | — | — | — | — | — | — | 0.5 | — | — | — | — |
| Paraffin Wax NF | 5.0 | 5.0 | 5.0 | 5.0 | 5.0 | 5.0 | 5.0 | 5.0 | 5.0 | 5.0 | — | — | — |
| White Petrolatum USP (Spectrum) | qs ad 100 | qs ad 100 | qs ad 100 | qs ad 100 | qs ad 100 | qs ad 100 | qs ad 100 | qs ad 100 | qs ad 100 | qs ad 100 | — | — | — |

Procedure for F4-F13: Prepared a slurry of the paclitaxel nanoparticles with a portion of the cyclomethicone (or mineral oil (F4) or FOMBLIN (F7)). Heated the petrolatum to 52±3° C. and added the remaining ingredients and mixed until melted and homogeneous. Added the paclitaxel slurry and mixed until homogenous. Mixed and allowed the batch to cool to 35° C. or below. An ointment was formed.

le;.3qExample 5 Physical and Chemical Stability of Anhydrous Compositions of Paclitaxel Nanoparticles with Hydrophobic Carriers The anhydrous hydrophobic composition samples were stored at 25° C. and 30° C. in 20 mL glass scintillation vials. The assay of paclitaxel was conducted using HPLC. The results of the assay and appearance stability studies are shown in Table 4 and Table 5 below. The viscosity was measured at room temperature with a Brookfield RV viscometer using a small sample adapter with a SC4-14 spindle and a 6R chamber at 5 rpm with an equilibration time of 2 minutes. The viscosity results are shown in Table 6 below.

TABLE 4

| | Stability at 25° C. | | | | | | | |
|---|---|---|---|---|---|---|---|---|
| | Assay (% of target) | | | | Appearance | | | |
| Formula | T = 0 | 1 month | 2 month | 3 month | T = 0 | 1 month | 2 month | 3 month |
| F4 | 95.3 | 99.6 | 100.3 | 99.5 | Off-white ointment | Off-white to yellow ointment | Off-white to yellow ointment | Off-white to yellow ointment |
| F5 | 98.2 | 101.7 | 101.0 | 100.9 | Off-white ointment | Off-white to yellow ointment | Off-white to yellow ointment | Off-white to yellow ointment |
| F6 | 97.2 | 100.5 | 97.9 | 98.4 | Off-white ointment | Off-white to yellow ointment | Off-white to yellow ointment | Off-white to yellow ointment |
| F6** | 98.0 | 98.5 | 100.2 | NP | Off-white to yellow ointment | Off-white to yellow ointment | Off-white to yellow ointment | NP |
| F8 | 107.6 | 100.5 | 101.1 | NP | Off-white to yellow ointment | Off-white to yellow ointment | Off-white to yellow ointment | NP |
| F9 | 95.6 | 98.3 | 101.2 | NP | Off-white to yellow ointment | Off-white to yellow ointment | Off-white to yellow ointment | NP |
| F10 | 98.6 | 103.8 | 101.2 | NP | Off-white to yellow ointment | Off-white to yellow ointment | Off-white to yellow ointment | NP |
| F11 | 99.8 | 99.8 | 100.9 | NP | Off-white to yellow ointment | Off-white to yellow ointment | Off-white to yellow ointment | NP |
| F12 | 98.7 | 98.3 | 99.1 | NP | Off-white to yellow ointment | Off-white to yellow ointment | Off-white to yellow ointment | NP |
| F13 | 96.5 | 93.9 | 96.0 | NP | Off-white to yellow ointment | Off-white to yellow ointment | Off-white to yellow ointment | NP |

**repeat batch

TABLE 5

Stability at 30° C.

| Formula | Assay (% of target) | | | | Appearance | | | |
|---|---|---|---|---|---|---|---|---|
| | T = 0 | 1 month | 2 month | 3 month | T = 0 | 1 month | 2 month | 3 month |
| F4 | 95.3 | 99.5 | 100.1 | 99.7 | Off-white ointment | Off-white to yellow ointment | Off-white to yellow ointment | Off-white to yellow ointment |
| F5 | 98.2 | 103.2 | 101.3 | 99.2 | Off-white ointment | Off-white to yellow ointment | Off-white to yellow ointment | Off-white to yellow ointment |
| F6 | 97.2 | 102.1 | 98.0 | 95.0 | Off-white ointment | Off-white to yellow ointment | Off-white to yellow ointment | Off-white to yellow ointment |
| F6** | 98.0 | 98.7 | 102.0 | NP | Off-white to yellow ointment | Off-white to yellow ointment | Off-white to yellow ointment | NP |
| F8 | 107.6 | 99.9 | 103.0 | NP | Off-white to yellow ointment | Off-white to yellow ointment | Off-white to yellow ointment | NP |
| F9 | 95.6 | 101.4 | 101.9 | NP | Off-white to yellow ointment | Off-white to yellow ointment | Off-white to yellow ointment | NP |
| F10 | 98.6 | 100.9 | 102.9 | NP | Off-white to yellow ointment | Off-white to yellow ointment | Off-white to yellow ointment | NP |
| F11 | 99.8 | 99.8 | 99.1 | NP | Off-white to yellow ointment | Off-white to yellow ointment | Off-white to yellow ointment | NP |
| F12 | 98.7 | 99.8 | 99.5 | NP | Off-white to yellow ointment | Off-white to yellow ointment | Off-white to yellow ointment | NP |
| F13 | 96.5 | 95.6 | 96.5 | NP | Off-white to yellow ointment | Off-white to yellow ointment | Off-white to yellow ointment | NP |

**repeat batch

TABLE 6

Viscosity Stability

| | Viscosity (cps) | | | |
|---|---|---|---|---|
| | F4 | F5 | F6 | F7 |
| T = 0 | 87,500 | 44,300 | 49,500 | 81,800 |
| 1 month @ 25° C. | 90,300 | 68,800 | 57,000 | NP |
| 3 month @ 25° C. | 101,000 | 47,800 | 38,000 | NP |
| 1 month @ 30° C. | 123,300 | 49,300 | 50,800 | NP |
| 2 month @ 30° C. | 112,300 | 53,500 | 38,000 | NP |
| 3 month @ 30° C. | 121,300 | 60,500 | 54,000 | NP |

Example 6 Particle Size Analysis of Paclitaxel Nanoparticles in Anhydrous Compositions with Hydrophobic Carriers Particle Size Method Using an ACCUSIZER Model 770/770A.

Instrument parameters: Sensor: LE 0.5 µm-400 µm, Sensor Range: Summation, Lower Detection Limit: 0.5 µm, Collection time: 60 sec, Number Channels: 128, Vessel Fluid Vol: 100 mL, Flow Rate: 60 mL/min, Max Coincidence: 8000 particles/mL, Sample Vessel: Accusizer Vessel, Sample Calculation: None, Voltage Detector: greater than 10 V, Particle Concentration Calculation: No, Concentration Range: 5000 to 8000 particles/mL, Automatic Data Saving: Selected, Subtract Background: Yes, Number of Autocycles: 1.

Sample Preparation: Added an aliquot of the sample formulation into a scintillation vial. Using a spatula, smeared the sample along the inner walls of the vial. Added about 20 mL of 2% Lecithin in ISOPAR-G™ (C10-11 isoparaffin) solution to the vial. Sonicated the vial for 1 minute. Insured that the sample had adequately dispersed in the solution.

Method: Filled the sample vessel with a filtered (0.22 µm) 2% Lecithin in ISOPAR-G solution and analyzed the background. Using a pipette, transferred a portion of the prepared sample to the vessel while stirring. Diluted or added sample to the vessel as necessary to provide a coincidence level between 5000 to 8000 particles/mL. Initiated the analysis through the instrument and verified that the coincidence level was 5000 to 8000 particles/mL for the analysis.

The results of the particle size analysis are shown in Table 7 and Table 8 below.

TABLE 7

Particle size stability at 25° C.

| | Mean particle size, µm (number) | | | | |
|---|---|---|---|---|---|
| Formula | Initial | 1 month | 3 month | 6 month | 12 month |
| F4 | 0.77 | 0.71 | NP | NP | NP |
| F5 | 0.72 | 0.71 | NP | NP | NP |
| F6 | 0.72 | 0.71 | NP | 0.71 | 0.72 |
| F6** | 0.70 | NP | 0.70 | NP | NP |
| F8 | 0.71 | NP | 0.71 | NP | NP |
| F9 | 0.70 | NP | 0.70 | NP | NP |
| F10 | 0.69 | NP | 0.69 | NP | NP |
| F11 | 0.69 | NP | 0.69 | NP | NP |

TABLE 7-continued

Particle size stability at 25° C.

| | | Mean particle size, μm (number) | | | |
|---|---|---|---|---|---|
| Formula | Initial | 1 month | 3 month | 6 month | 12 month |
| F12 | 0.70 | NP | 0.70 | NP | NP |
| F13 | 0.69 | NP | 0.70 | NP | NP |
| A | 0.72 | NP | NP | NP | NP |
| B | 0.77 | NP | NP | NP | NP |
| C | 0.84 | NP | NP | NP | NP |

**repeat batch

TABLE 8

Particle size stability at 30° C.

| | | Mean particle size, μm (number) | | | |
|---|---|---|---|---|---|
| Formula | Initial | 1 month | 3 month | 6 month | 12 month |
| F4 | 0.77 | 0.73 | NP | NP | NP |
| F5 | 0.72 | 0.70 | NP | NP | NP |

TABLE 8-continued

Particle size stability at 30° C.

| | | Mean particle size, μm (number) | | | |
|---|---|---|---|---|---|
| Formula | Initial | 1 month | 3 month | 6 month | 12 month |
| F6 | 0.72 | 0.70 | NP | 0.70 | 0.73 |
| F6** | 0.70 | NP | 0.72 | NP | NP |
| F8 | 0.71 | NP | 0.71 | NP | NP |
| F9 | 0.70 | NP | 0.71 | NP | NP |
| F10 | 0.69 | NP | 0.69 | NP | NP |
| F11 | 0.69 | NP | 0.70 | NP | NP |
| F12 | 0.70 | NP | 0.71 | NP | NP |
| F13 | 0.69 | NP | 0.71 | NP | NP |

**repeat batch

As can be seen by the data, the particle size of paclitaxel nanoparticles in samples F4 through F6 did not grow larger than 20% of the initial mean particle size when stored at room temperature (25° C.) and at 30° C. for 1 month. The particle size of paclitaxel nanoparticles in sample F6 did not grow larger than 20% of the initial mean particle size when stored at room temperature (25° C.) and at 30° C. for 6 months and for 12 months. The particle size of paclitaxel nanoparticles in samples F6**(repeat batch with the same formula as F6) and F8 through F13 did not grow larger than 20% of the initial mean particle size when stored at room temperature (25° C.) and at 30° C. for 3 months.

Example 7 Aqueous Based Compositions of Paclitaxel Nanoparticles

Aqueous based compositions of paclitaxel nanoparticles are shown in Table 9.

TABLE 9

| Component (% w/w) | Formula Number | | | | | | | |
|---|---|---|---|---|---|---|---|---|
| | F1 | F2 | F3 | D | E | F | G | H |
| Paclitaxel Particles | 1.0 | 1.0 | 1.0 | 0.5 | 0.5 | 0.5 | 0.5 | 0.5 |
| DGME (TRANSCUTOL P) | 5.0 | 5.0 | — | 5.0 | 5.0 | 5.0 | 5.0 | 5.0 |
| PEG 400 | 5.0 | 5.0 | 5.0 | 5.0 | 5.0 | 5.0 | 5.0 | 5.0 |
| Glycerin | 10.0 | 10.0 | 10.0 | 5.0 | 5.0 | 5.0 | 5.0 | 5.0 |
| Polysorbate 80 | 1.0 | 1.0 | 1.0 | 0.1 | 0.1 | 0.1 | 0.1 | 0.1 |
| Poloxamer 407 | 2.0 | 2.0 | 2.0 | — | — | — | — | — |
| Povidone K90 | 0.15 | 0.15 | 0.15 | 0.1 | 0.1 | 0.1 | 0.1 | 0.1 |
| Benzyl Alcohol | 0.5 | 0.5 | 0.5 | — | — | — | — | — |
| Methylparaben | 0.15 | 0.15 | 0.15 | 0.15 | 0.15 | 0.15 | 0.15 | 0.15 |
| Propylparaben | 0.02 | 0.02 | 0.02 | 0.02 | 0.02 | 0.02 | 0.02 | 0.02 |
| Benzalkonium Chloride (50%) | — | 1.0 | 1.0 | — | — | 0.1 | 0.1 | — |
| CARBOPOL 974 P | — | — | — | 0.75 | — | — | — | — |
| CARBOPOL ULTREZ 10 | 0.5 | — | — | — | 0.5 | — | — | — |
| Trolamine Solution (10%) | qs pH 5.5 | — | — | qs pH 5.5 | qs pH 5.5 | — | — | — |
| Hydroxypropyl Methylcellulose (K200M Pharm) | — | 1.0 | 1.0 | — | — | 2.0 | — | — |
| Purified Water | qs ad 100 | qs ad 100 | qs ad 100 | qs ad 100 | qs ad 100 | qs ad 100 | qs ad 100 | qs ad 100 |

Samples were observed for crystal growth of the paclitaxel nanoparticles. The results are shown in Table 10 below.

TABLE 10

| Formula Number | Visual observation by light microscopy- Needle shaped crystals observed? |
|---|---|
| D | No, <5 μm @ 24 hrs & 6 days, RT |
| E | No, <5 μm @ 24 hrs & 6 days, RT |
| F | No, <5 μm @ 24 hrs & 6 days, RT |
| G | No, <5 μm @ 24 hrs & 6 days, RT |
| H | Yes, >5 μm @ 24 hrs & 6 days, RT |

As can be seen by the data, the presence of benzalkonium chloride, CARBOPOL 974P, or CARBOPOL ULTREZ 10 inhibited the growth of crystals in the aqueous based compositions.

Example 8 Particle Size Analysis of Paclitaxel Nanoparticles in Aqueous Based Compositions Particle Size Method Using an ACCUSIZER Model 770/770A.

Instrument parameters: Sensor: LE 0.5 µm-400 µm, Sensor Range: Summation, Lower Detection Limit: 0.5 µm, Collection time: 60 sec, Number Channels: 128, Vessel Fluid Vol: 100 mL, Flow Rate: 60 mL/min, Max Coincidence: 8000 particles/mL, Sample Vessel: Accusizer Vessel, Sample Calculation: None, Voltage Detector: greater than 10 V, Particle Concentration Calculation: No, Concentration Range: 5000 to 8000 particles/mL, Automatic Data Saving: Selected, Subtract Background: Yes, Number of Autocycles: 1.

Sample Preparation: Added an aliquot of the sample formulation into a scintillation vial. Using a spatula, smeared the sample along the inner walls of the vial. Added about 20 mL of 0.2 µm filtered distilled water to the vial. Sonicated the vial for 1 minute. Insured that the sample had adequately dispersed in the solution.

Method: Filled the sample vessel with 0.2 µm filtered distilled water and analyzed the background. Using a pipette, transferred a portion of the prepared sample to the vessel while stirring. Diluted or added sample to the vessel as necessary to provide a coincidence level between 5000 to 8000 particles/mL. Initiated the analysis through the instrument and verified that the coincidence level was 5000 to 8000 particles/mL for the analysis.

The results of the particle size analysis are shown in Table 11 below.

TABLE 11

Particle size of aqueous based compositions

| | Mean particle size, µm (number) | |
|---|---|---|
| Formula | Initial | 6 month at RT |
| F1 | 1.06 | 0.82 |
| F2 | 0.74 | 0.77 |
| F3 | 0.70 | 0.77 |
| D | 0.80 | NP |
| E | 0.79 | NP |
| F | 0.85 | NP |

As can be seen by the data of formulas F1, F2, and F3 in Table 11, the presence of benzalkonium chloride, CARBOPOL 974P, or CARBOPOL ULTREZ 10 inhibited the growth of crystals in the aqueous based compositions such that the mean particle size of the drug nanoparticles did not grow larger than 20% of the initial mean particle size when the composition was stored at room temperature for 6 months.

Example 9 In Vitro Skin Penetration Diffusion Study

A study to determine the rate and extent of in vitro skin permeation of the formulas F1 through F13 into and through intact human cadaver skin using a Franz diffusion cell system was conducted. Concentrations of paclitaxel were measured in the receptor chamber of the diffusion cell at varying time points. Upon conclusion of the diffusion study, the skin was tape stripped and split into epidermal and dermal layers. The paclitaxel in the epidermal and dermal tissue was extracted using an extraction solvent and also analyzed.

Analytical Method: A Mass spectrometry (MS) method was developed for analyzing the paclitaxel. The MS conditions were as follows in Table 12 below.

TABLE 12

| Instrument: | Agilent 1956B MS (TM-EQ-011) | |
|---|---|---|
| Column: | XBridge C18 4.6 × 100 mm, 5µm | |
| Mobile Phase: | A: Acetonitrile B: 0.1% Formic acid in water | |
| Gradient: | Time (minutes) | % B |
| | 0 | 50% |
| | 2 | 5% |
| | 5 | 5% |
| Flow Rate: | 1 mL/min | |
| Column Temperature: | 30° C. | |
| MS Detection: | SIM 854.4 + Frag 180, Gain 20 | |
| Injection Volume: | 20 µL | |
| Retention time: | ~2.86 min | |

Franz Diffusion Cell (FDC) Study—Methodology

Skin Preparation: Intact human cadaver skin was purchased from New York Firefighters Tissue Bank (NFFTB). The skin was collected from the upper back and dermatomed by the tissue bank to a thickness of ~500 µm. Upon receipt of the skin from the tissue bank, the skin was stored frozen at −20° C. until the morning of the experiment. Prior to use, the skin was removed from the freezer and allowed to fully thaw at room temperature. The skin was then briefly soaked in a PBS bath to remove any residual cryoprotectants and preservatives. Only areas of the skin that were visually intact were used during the experiment. For each study, two separate donors were used, each donor having a corresponding three replicates.

Receptor Fluid Preparation: Based on the results of preliminary solubility data, a receptor fluid of 96 wt % phosphate buffered saline ("PBS") at pH 7.4 and 4 wt % hydroxyl propyl beta cyclodextrin (HPBCD) was chosen. The solubility of the active in the receptor fluid (~0.4 µg/mL) was shown to be adequate to maintain sink conditions during the studies. The receptor fluid was degassed by filtering the receptor fluid through a ZapCap CR 0.2 µm membrane while pulling vacuum. The filtered receptor fluid was stirred for an additional 20 minutes while maintaining vacuum to ensure complete degassing.

Diffusion Cell Assembly: The cadaver skin was removed from the freezer and allowed to defrost in a bio-safety hood for 30 minutes. The skin was thoroughly defrosted prior to opening the package. The cadaver skin was removed from the package and placed on the bio-safety hood countertop with the stratum corneum side up. The skin was patted dry with a Kim Wipe, then sprayed with fresh PBS and patted dry again. This process was repeated 3 more times to remove any residues present on the skin. The receptor wells were then filled with the degassed receptor fluid. A Teflon coated stir bar was added to each receptor well. The defrosted cadaver skin was examined and only areas with even thickness and no visible damage to the surface were used. The skin was cut into ~2 cm×2 cm squares. The skin piece was centered on the donor wells, stratum corneum (SC) side up. The skin was centered and the edges flattened out. The donor and receptor wells were then aligned and clamped together with a clamp. Additional receptor fluid was added where necessary. Any air bubbles present were removed by tilting the cell, allowing air to escape along the sample port. Diffusion cells were then placed in to the stirring dry block heaters and allowed to rehydrate for 20 minutes from the receptor fluid. The block heaters were maintained at 32° C. throughout the experiment with continuous stirring. The skin was allowed to hydrate for 20 minutes and the barrier integrity of each skin section was tested. Once the membrane integrity check study was complete, the entire receptor chamber volume was replaced with the receptor fluid.

Formulation Application Procedure: The formulations were applied to the stratum corneum of the skin. A one-time dosing regimen was used for this study. The test articles were applied as 10 µl doses to the skin using a positive displacement Nichiryo pipetter. The formulations were then spread across the surface of the skin using a glass rod. Cells were left uncapped during the experiment. The theoretical dose of paclitaxel per cell is shown in Table 13 below.

TABLE 13

| Formula Number | % w/w Paclitaxel in formula | Nominal formulation dose per cell | Theoretical Paclitaxel dose per cell |
|---|---|---|---|
| F1 | 1.0 wt % | 10 µl | 182 µg/cm² |
| F2 | 1.0 wt % | 10 µl | 182 µg/cm² |
| F3 | 1.0 wt % | 10 µl | 182 µg/cm² |
| F4 | 1.0 wt % | 10 µl | 182 µg/cm² |
| F5 | 1.0 wt % | 10 µl | 182 µg/cm² |
| F6 | 1.0 wt % | 10 µl | 182 µg/cm² |
| F7 | 1.0 wt % | 10 µl | 182 µg/cm² |
| F6* | 1.0 wt % | 10 µl | 182 µg/cm² |
| F8 | 0.5 wt % | 10 µl | 91 µg/cm² |
| F9 | 2.0 wt % | 10 µl | 364 µg/cm² |
| F10 | 1.0 wt % | 10 µl | 182 µg/cm² |
| F11 | 1.0 wt % | 10 µl | 182 µg/cm² |
| F12 | 1.0 wt % | 10 µl | 182 µg/cm² |
| F13 | 1.0 wt % | 10 µl | 182 µg/cm² |

*repeat analysis

Sampling of Receptor Fluid: At 3, 6, 12 and 24 hours, 300 µL sample aliquots were drawn from the receptor wells using a graduated Hamilton type injector syringe. Fresh receptor medium was added to replace the 300 µL sample aliquot.

Tape Stripping and Heat Splitting: At 24 hours, the skin was wiped clean using PBS/ethanol soaked KimWipes. After the residual formulation was wiped off and the skin dried with KimWipes, the stratum corneum was tape stripped three times—each tape stripping consisting of applying cellophane tape to the skin with uniform pressure and peeling the tape off. The tape strips were collected and frozen for future analysis. The first three tape strips remove the uppermost layer of the stratum corneum and act as an extra skin cleaning step. The active is typically not considered fully absorbed in this area. These tape strips are usually only analyzed for a mass balance assay. After the skin was tape stripped, the epidermis of each piece was then separated from the underlying dermal tissue using tweezers or a spatula. The epidermis and dermal tissue were collected and placed in 4 mL borosilicate glass vials. After all the skin pieces were separated, an aliquot of the extraction solvent was added to the glass vial. This process consisted of adding 2 mL of DMSO to the vial and incubating for 24 hours at 32° C. After the extraction time was over, 300 µL sample aliquots of the extraction fluid were collected and filtered.

Figure 2:
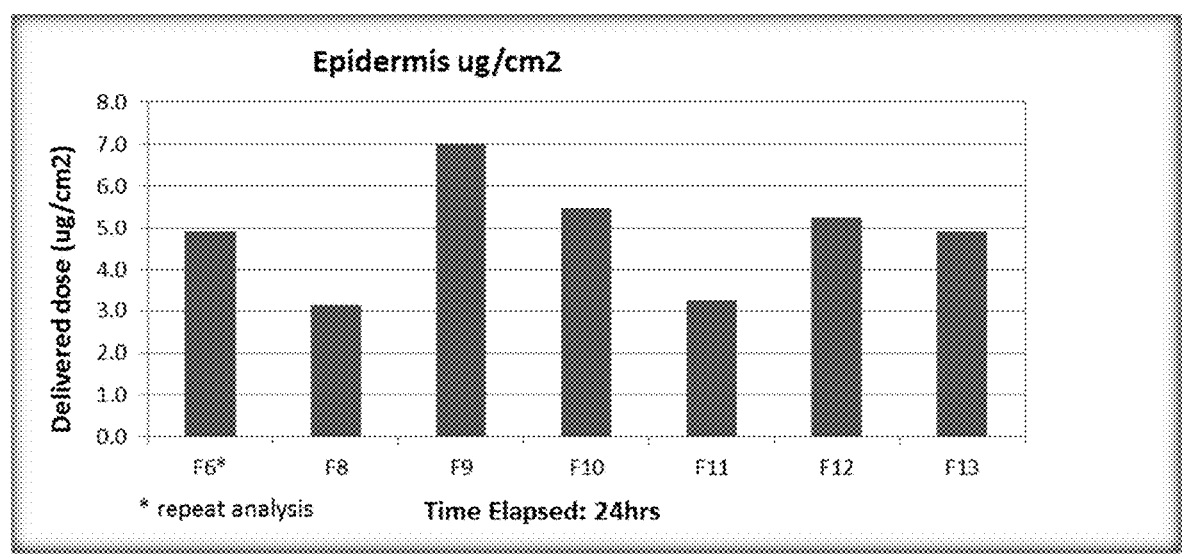
FIG. 2 graphically shows the concentration of paclitaxel (μg/cm2) delivered in vitro into the epidermis for formulas F6*(repeat analysis) and F8 through F13.
Figure 3:
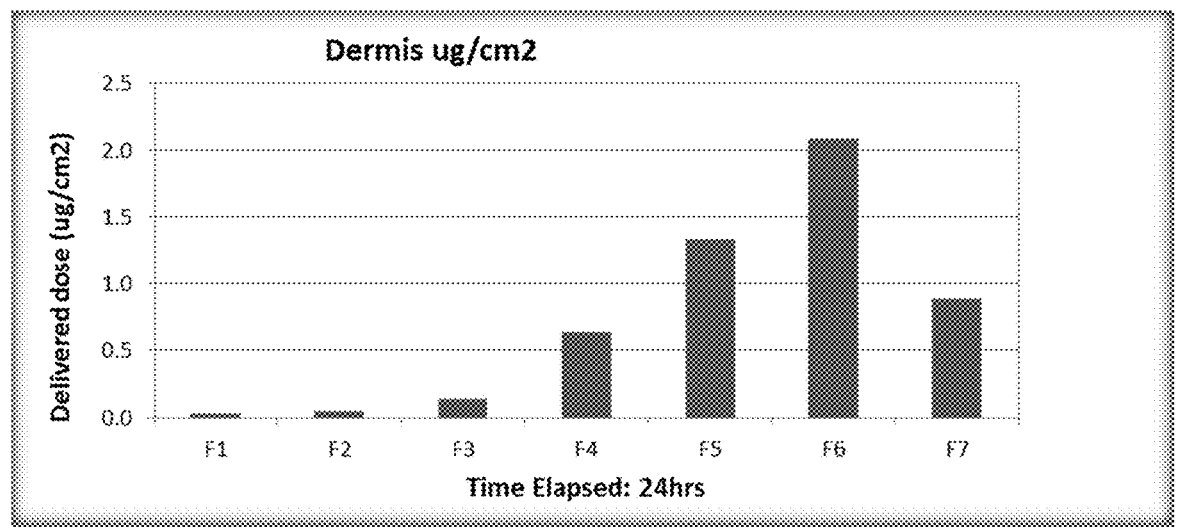
FIG. 3 graphically shows the concentration of paclitaxel (μg/cm2) delivered in vitro into the dermis for formulas F1 through F7.
Figure 4:
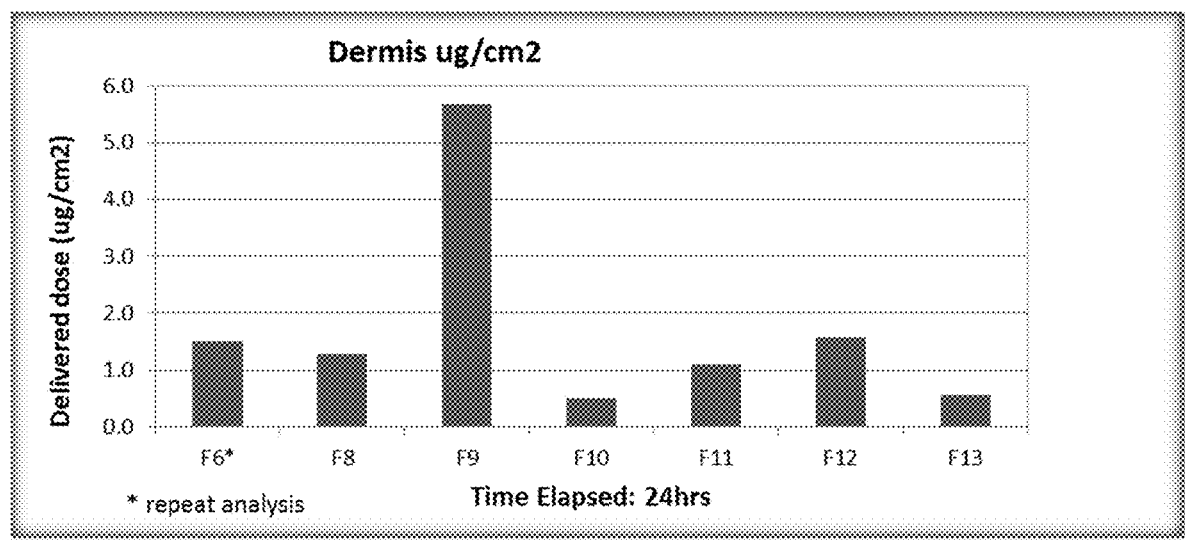
FIG. 4 graphically shows the concentration of paclitaxel (μg/cm2) delivered in vitro into the dermis for formulas F6*(repeat analysis) and F8 through F13.

Analysis of Samples: Sample aliquots were analyzed for paclitaxel using the analytical method as described above.
Results:

The results in Table 14 below show the delivered dose of paclitaxel (µg/cm²) in the receptor fluid at various time points (transdermal flux) and the concentration of paclitaxel (µg/cm²) delivered into the epidermis and dermis (penetration) after 24 hours elapsed time for formulations F1 through F13. FIG. 1 graphically shows the concentration of paclitaxel (µg/cm²) delivered into the epidermis for formulas F1 through F7. FIG. 2 graphically shows the concentration of paclitaxel (µg/cm²) delivered into the epidermis for formulas F6*(repeat analysis) and F8 through F13. FIG. 3 graphically shows the concentration of paclitaxel (µg/cm2) delivered into the dermis for formulas F1 through F7. FIG. 4 graphically shows the concentration of paclitaxel (µg/cm2) delivered into the dermis for formulas F6*(repeat analysis) and F8 through F13.

Note: Formulas F1 through F6 were tested in one in vitro study, and formulas F6* and F8 through F13 were tested in a second separate in vitro study, with different cadaver skin lots. Analysis of formula F6 was repeated in the second study (and notated as F6*) so that it could be evaluated and compared with the other formulas in the second study.

TABLE 14

| | Paclitaxel Delivered Dose (µg/cm²) | | | | | |
|---|---|---|---|---|---|---|
| Formula | Receptor Fluid 3 hrs | Receptor Fluid 6 hrs | Receptor Fluid 12 hrs | Receptor Fluid 24 hrs | Epidermis | Dermis |
| F1 | 0.000 | 0.000 | 0.000 | 0.000 | 0.202 | 0.030 |
| F2 | 0.000 | 0.000 | 0.000 | 0.000 | 0.161 | 0.042 |
| F3 | 0.000 | 0.000 | 0.000 | 0.000 | 0.056 | 0.138 |
| F4 | 0.000 | 0.000 | 0.000 | 0.000 | 0.690 | 0.639 |
| F5 | 0.000 | 0.000 | 0.000 | 0.004 | 0.780 | 1.337 |
| F6 | 0.000 | 0.000 | 0.000 | 0.000 | 1.927 | 2.088 |
| F7 | 0.000 | 0.000 | 0.000 | 0.000 | 0.633 | 0.882 |
| F6* | 0.000 | 0.000 | 0.000 | 0.000 | 4.910 | 1.508 |
| F8 | 0.000 | 0.000 | 0.000 | 0.000 | 3.155 | 1.296 |
| F9 | 0.000 | 0.000 | 0.000 | 0.000 | 7.010 | 5.679 |
| F10 | 0.000 | 0.000 | 0.000 | 0.000 | 5.470 | 0.494 |
| F11 | 0.000 | 0.000 | 0.000 | 0.000 | 3.262 | 1.098 |
| F12 | 0.000 | 0.000 | 0.000 | 0.000 | 5.269 | 1.571 |
| F13 | 0.000 | 0.000 | 0.000 | 0.000 | 4.903 | 0.548 |

*repeat analysis

As can be seen by the results in Table 14, the transdermal flux of the paclitaxel through the skin (epidermis and dermis) was none or only a negligible amount, i.e., less than 0.01 µg/cm². As can be seen by the results in Table 14 and FIGS. 1, 2, 3 & 4, the penetration of paclitaxel into the skin (epidermis and dermis) was far greater with the anhydrous hydrophobic formulations (F4 through F13) than with the aqueous formulations (F1 through F3), even though the aqueous formulations contained the skin penetration enhancer DGME (TRANSCUTOL P). The results also show that the anhydrous hydrophobic formulations with cyclomethicone exhibited greater skin penetration (epidermis and dermis) over the anhydrous hydrophobic formulations without cyclomethicone. Additionally, the results show that the addition of other skin penetration enhancers to the anhydrous hydrophobic formulations containing cyclomethicone had little or no effect on the skin penetration (epidermis and dermis) of these compositions.

Example 10—Formulations for CIN and Cervical Cancer Studies

The following ointment formulations shown in Table 15 were prepared for use in CIN and cervical cancer studies.

TABLE 15

| Component (% w/w) | F14 (0.15%) | F15 (0.3%) | F16 (1%) | F17 (2%) |
|---|---|---|---|---|
| Paclitaxel Nanoparticles | 0.15 | 0.3 | 1.0 | 2.0 |
| Mineral Oil USP | 5.0 | 5.0 | 5.0 | 5.0 |
| ST-Cyclomethicone 5 NF (Dow Corning) | 13.0 | 13.0 | 13.0 | 13.0 |
| Paraffin Wax NF | 5.0 | 5.0 | 5.0 | 5.0 |
| White Petrolatum USP (Spectrum) | qs ad 100 | qs ad 100 | qs ad 100 | qs ad 100 |

The formulas listed in Table 15 containing paclitaxel nanoparticles were manufactured each in a 6 kg batch size. The formulas were then packaged in 15 gm laminate tubes.

The manufacturing processes for lots F14, F15, and F16 were as follows: The petrolatum, mineral oil, paraffin wax, and a portion of the cyclomethicone were added to a vessel and heated to 52±3° C. while mixing with a propeller mixer until melted and homogeneous. The paclitaxel nanoparticles were added to a vessel containing another portion of cyclomethicone and first mixed with a spatula to wet the nanoparticles, then mixed with an IKA Ultra Turrax Homogenizer with a S25-25G dispersing tool until a homogeneous slurry is obtained while keeping the container in an ice/water bath. The slurry was then added to the petrolatum/paraffin wax container while mixing with the propeller mixer followed by rinsing with the remaining portion of cyclomethicone and mixed until the batch was visually homogeneous while at 52±3° C. The batch was then homogenized using a Silverson homogenizer. Afterward, the batch was mixed with a propeller mixer until a homogeneous ointment was formed and the batch cooled to 35° C. or below.

The manufacturing process for lot F17 was as follows: The petrolatum and paraffin wax were added to a vessel and heated to 52±3° C. while mixing with a propeller mixer until melted and homogeneous. The paclitaxel nanoparticles were added to a vessel containing the cyclomethicone and a portion of mineral oil, and first mixed with a spatula to wet the nanoparticles, then mixed with an IKA Ultra Turrax Homogenizer with a S25-25G dispersing tool until a homogeneous slurry is obtained while keeping the container in an ice/water bath. The slurry was then added to the petrolatum/paraffin wax container while mixing with the propeller mixer followed by rinsing with the remaining portion of mineral oil and mixed until the batch was visually homogeneous while at 52±3° C. The batch was then homogenized using a Silverson homogenizer. Afterward, the batch was mixed with a propeller mixer until a homogeneous ointment was formed and the batch cooled to 35° C. or below.

The chemical and physical analytical results for each formula in Table 15 are shown in Tables 16-19 for T=0, 1 month, and 3 months at 25° C.

TABLE 16

| Test | Formula No. F14 (0.15%) | | |
|---|---|---|---|
| | T = 0 | 1 month | 3 month |
| Appearance (note1) | conforms | conforms | conforms |
| Assay, % target | 103.4 | 103.2 | 101.1 |
| Viscosity (note 2) | 131000 cps | 147000 cps | 159500 cps |
| Mean Particle Size (number) | 0.71 μm | 0.70 μm | 0.70 μm |

Note
1: Off-white to yellow ointment
Note
2: Brookfield RV viscometer on a helipath stand with the helipath on, with a T-E spindle at 10 RPM at room temperature for 45 seconds.

TABLE 17

| Test | Formula No. F15 (0.3%) | | |
|---|---|---|---|
| | T = 0 | 1 month | 3 month |
| Appearance (note1) | conforms | conforms | conforms |
| Assay, % target | 101.2 | 101.9 | 102.5 |
| Viscosity (note 2) | 195500 cps | 154000 cps | 153500 cps |
| Mean Particle Size (number) | 0.72 μm | 0.71 μm | 0.70 μm |

Note
1: Off-white to yellow ointment
Note
2: Brookfield RV viscometer on a helipath stand with the helipath on, with a T-E spindle at 10 RPM at room temperature for 45 seconds.

TABLE 18

| Test | Formula No. F16 (1%) | | |
|---|---|---|---|
| | T = 0 | 1 month | 3 month |
| Appearance (note1) | conforms | conforms | conforms |
| Assay, % target | 102.1 | 102.2 | 102.7 |
| Viscosity (note 2) | 205000 cps | 218000 cps | 180000 cps |
| Mean Particle Size (number) | 0.70 μm | 0.70 μm | 0.70 μm |

Note
1: Off-white to yellow ointment
Note
2: Brookfield RV viscometer on a helipath stand with the helipath on, with a T-E spindle at 10 RPM at room temperature for 45 seconds.

TABLE 19

| Test | Formula No. F17 (2%) | | |
|---|---|---|---|
| | T = 0 | 1 month | 3 month |
| Appearance (note1) | conforms | conforms | conforms |
| Assay, % target | 101.7 | 101.1 | 105.0 |
| Viscosity (note 2) | 158000 cps | 177000 cps | 162000 cps |
| Mean Particle Size (number) | 0.70 μm | 0.69 μm | 0.69 μm |

Note
1: Off-white to yellow ointment
Note
2: Brookfield RV viscometer on a helipath stand with the helipath on, with a T-E spindle at 10 RPM at room temperature for 45 seconds.

Example 11—Dose-Rising, Efficacy, Safety and Tolerability Study for Cervical Intraepithelial Neoplasia (CIN)

The topical formulations in Table 15 are to be used in a Phase II dose-rising, safety study for cervical intraepithelial neoplasia (CIN) in humans. The study will compare the safety and efficacy of the 4 formulations from Table 15: F14 (0.15%), F15 (0.3%), F16 (1.0%), and F17 (2.0%) applied topically to the ectocervix of subjects with CIN. A cervical cap may or may not be used to maintain localization of the formulations to the cervix for at least 7 days, and up to 14 days. Subjects with biopsy proven CIN 2 or 3 scheduled for removal of CIN will be enrolled in four dose-escalating cohorts of 3 subjects assigned consecutively as follows: Cohort 1: 3 subjects with F14 (0.15%); Cohort 2: 3 subjects with F15 (0.3%); Cohort 3: 3 subjects with F16 (1.0%); Cohort 4: 3 subjects with F17 (2.0%). Up to 1 ml of the formulations will be applied topically to the ectocervix on Day 1 as a single treatment. During the follow-up period, subjects will return to the clinic 8, 15, and 28 days after treatment, at which point the subject will exit the study. At the final study visit (28 days after treatment) subjects will undergo an excision or punch biopsy to record the stage of CIN. PK samples will be obtained on Day 1 at 1, 2, 4, 8, and 24 hours post-injection, and at each clinic visit thereafter. The Medical Monitor will review all available data prior to dose escalation. Dose-escalation of the formulations will be determined by the Medical Monitor. This will be repeated for each escalated dose until all dose levels have been enrolled or a dose is determined unsafe.

Safety will be assessed in an ongoing manner and formal safety reviews will be conducted twice for each cohort: after Day 15 and after Day 28 of the last subject in the cohort. The next dose level cohort will enroll upon a finding of safety and tolerability at the previous cohort's first safety review. If a safety and tolerability issue becomes apparent in a cohort, an additional three subjects will be enrolled at that dose-level, for a maximum of six subjects in that cohort. If ≥1 of the same safety and tolerability issue recurs in the additional 3 subjects, the prior dose-level will be determined to be the highest dose with an acceptable safety and tolerability profile. If no further safety and tolerability issues are identified in the expanded cohort, dose-escalation will continue. Once the highest dose with an acceptable safety and tolerability profile has been determined by the Medical Monitor, PI, and Sponsor Medical Director, a further 3 subjects will be enrolled to that dose level in order to increase the subject numbers. The study will be stopped after these final 3 subjects.

Efficacy will be assessed as the change in CIN status between the initial diagnostic biopsy performed prior to enrollment in the study, and the CIN status from an excisional or punch biopsy obtained 28 days after the single application of the formulation.

The primary objective of this study is to evaluate the safety and tolerability of the topical formulations applied to the ectocervix in subjects with cervical intraepithelial neoplasia (CIN) as assessed by Treatment Emergent Adverse Events (TEAEs), vital signs, laboratory results, and physical examination. Secondary objectives are (a) to describe the pharmacokinetics of the topical formulations applied to the ectocervix, and (b) to obtain preliminary information on the efficacy of the topical formulations applied to CIN defined by regression or clearance of CIN, and by colposcopic changes as defined by the modified Reid Colposcopic Index (RCI).

The population of the study will be a minimum of 15 and a maximum of 24 eligible subjects across two sites with CIN 2 or 3 confirmed by histology.

The primary endpoint will be safety and tolerability, as assessed by adverse events, changes in vital signs, laboratory results, and physical examination. The secondary endpoints will be PK parameters and preliminary efficacy of the topical formulations applied to the ectocervix, as defined by:
(a) change in grade of CIN lesion as determined by biopsy;
(b) change in the modified Reid Colposcopic Index (RCI) between baseline (Day 1), and Day 28; (c) reduction in size of the CIN lesions, measured as a reduction of the longest diameter of the lesion, or sum of longest diameters of the lesions; and (d) proportion of subjects defined as Complete Responders (CR) and Partial Responders (PR) to the formulations at Day 28 (see Table 20 below). The criteria for classification of CIN is as follows:
CIN 1: Mild dysplasia or mild dyskaryosis. Good maturation of cells through the depth of the cervical epithelium, with minimal nuclear abnormalities and few mitotic figures. Undifferentiated cells are confined to the deeper/lower third of the epithelium. Mitotic figures are not very numerous. Cytopathic changes due to HPV infection may be observed in the full thickness of the epithelium.
CIN 2: Moderate dysplasia or moderate dyskaryosis. Dysplastic changes mostly restricted to the lower half or two-thirds of the epithelium, with more marked nuclear abnormalities than CIN 1. Mitotic figures are seen through the lower half of the epithelium.
CIN 3: Severe dysplasia or severe dyskaryosis. Differentiation and stratification may be totally absent or present only in the superficial quarter of the epithelium with numerous mitotic figures. Nuclear abnormalities extend throughout the thickness of the epithelium. Many mitotic figures have abnormal forms.

The Clinical Response is defined by changes in CIN between baseline and 28 days. Baseline is defined as the CIN classification obtained by biopsy within 2 weeks prior to entry into the study, and within 4 weeks prior to administration of the formulations. The Clinical Response as defined by Histological Response is shown in Table 20.

TABLE 20

| Clinical Response | Histological Response |
| --- | --- |
| Stable Disease (SD) | No change. |
| Partial Response (PR) | CIN 3 to CIN 1 or within normal limits (WNL). |
| | CIN 2 to CIN 1 or within normal limits (WNL). |
| Complete Response (CR) | CIN 3 or CIN 2 to within normal limits (WNL). |
| Progressive Disease (PD) | CIN 2 to CIN 3, CIS, microinvasion, invasion, or increased lesion size with stable disease (SD). |

The proportion of subjects who respond to the formulations will be compared to non-responders. A "Responder" is defined as a CR or PR. A non-responder is defined as SD or PD.

The modified Reid Colposcopic Index (RCI) is a colposcopic grading system that will be used to grade cervical epithelium at all study visits. The system applies 0-2 points to four colposcopic signs: color, lesion margin and surface configuration, vessels, and iodine staining. A change in the overall RCI score on days 8, 15 and 28 will be compared to baseline. Baseline is defined as the average RCI score of colposcopy findings determined at the screening visit and the treatment visit (Day 1). The criteria for the modified Reid Colposcopic Index is shown in Table 21.

TABLE 21

| Colposcopic signs | Zero point | One point | Two points |
| --- | --- | --- | --- |
| Color | Low-intensity acetowhitening (not completely opaque); indistinct acetowhitening; transparent or translucent acetowhitening. Acetowhitening beyond the margin of the transformation zone. Pure snow-white color with intense surface shine | Intermediate shade-grey/white color and shiny surface (most lesions should be scored in this category) | Dull, opaque, oyster white; grey |
| Lesion margin and surface configuration | Microcondylomatous or micropapillary contour. Flat lesions with indistinct margins. | Regular-shaped, symmetrical lesions with smooth, straight | Rolled, peeling edges. Internal demarcations between areas of differing |

TABLE 21-continued

| Colposcopic signs | Zero point | One point | Two points |
|---|---|---|---|
|  | Feathered or finely scalloped margins, Angular, jagged lesions. Satellite lesions beyond the margin of the transformation zone | outlines | colposcopic appearance-a central area of high-grade change and peripheral area of low-grade change |
| Vessels | Fine/uniform-calibre vessels-closely and uniformly placed. Poorly formed patterns of fine punctation and/or mosaic. Vessels beyond the margin of the transformation zone. Fine vessels within microcondylomatous or micropapillary lesions | Absent vessels | Well defined coarse punctation or mosaic, sharply demarcated-and randomly and widely placed |
| Iodine staining | Positive iodine uptake giving mahogany-brown color. Negative uptake of insignificant lesion, i.e., yellow staining by a lesion scoring three points or less on the first three criteria, Areas beyond the margin of the transformation zone, conspicuous on colposcopy, evident as iodine-negative areas (such areas are frequently due to parakeratosis) | Partial iodine uptake-variegated, speckled appearance | Negative iodine uptake of significant lesion, i.e., yellow staining by a lesion already scoring four points or more on the first three criteria |

Photographs of all target CIN lesions will be taken at all visits. These photographs will be reviewed at the end of the study for efficacy and local toxicity.

Example 12—Dose-Rising, Efficacy, Safety and Tolerability Study for Cervical Cancer The topical formulations in Table 15 are to be used in a Phase II dose-rising, safety study for cervical cancer in humans. The study will compare the safety and efficacy of the 4 formulations from Table 15: F14 (0.15%), F15 (0.3%), F16 (1.0%), and F17 (2.0%) applied topically to the ectocervix and endocervical canal of subjects with cervical cancer. A cervical cap may or may not be used to maintain localization of the formulations to the cervix for at least 7 days, and up to 14 days. Subjects with biopsy proven cervical cancer scheduled for total abdominal hysterectomy and bilateral lymph node dissection will be enrolled in four dose-escalating cohorts of 3 subjects assigned consecutively as follows: Cohort 1: 3 subjects with F14 (0.15%); Cohort 2: 3 subjects with F15 (0.3%); Cohort 3: 3 subjects with F16 (1.0%); Cohort 4: 3 subjects with F17 (2.0%). Up to 1 ml of the formulations will be applied topically to the ectocervix and endocervical canal on Day 1 as a single treatment. During the follow-up period, subjects will return to the clinic 8, 15, and 28 days after treatment, at which point the subject will undergo total abdominal hysterectomy and bilateral lymph node dissection and exit the study. PK samples will be obtained on Day 1 at 1, 2, 4, 8, and 24 hours post-injection, and at each clinic visit thereafter. The Medical Monitor will review all available data prior to dose escalation. Dose-escalation of the formulations will be determined by the Medical Monitor. This will be repeated for each escalated dose until all dose levels have been enrolled or a dose is determined unsafe.

Safety will be assessed in an ongoing manner and formal safety reviews will be conducted twice for each cohort: after Day 15 and after Day 28 of the last subject in the cohort. The next dose level cohort will enroll upon a finding of safety and tolerability at the previous cohort's first safety review. If a safety and tolerability issue becomes apparent in a cohort, an additional three subjects will be enrolled at that dose-level, for a maximum of six subjects in that cohort. If ≥1 of the same safety and tolerability issue recurs in the additional 3 subjects, the prior dose-level will be determined to be the highest dose with an acceptable safety and tolerability profile. If no further safety and tolerability issues are identified in the expanded cohort, dose-escalation will continue. Once the highest dose with an acceptable safety and tolerability profile has been determined by the Medical Monitor, PI, and Sponsor Medical Director, a further 3 subjects will be enrolled to that dose level in order to increase the subject numbers. The study will be stopped after these final 3 subjects.

Efficacy will be assessed as the change in cervical cancer status between the initial diagnostic biopsy performed prior to enrollment in the study, and the pathologic evaluation of the cervix after hysterectomy (28 days after the single application of the formulation).

The primary objective of this study is to evaluate the safety and tolerability of the topical formulations applied to the ectocervix and endocervical canal in subjects with cervical cancer as assessed by Treatment Emergent Adverse Events (TEAEs), vital signs, laboratory results, and physical examination. Secondary objectives are (a) to describe the pharmacokinetics of the topical formulations applied to the ectocervix and endocervical canal, (b) to determine the effect of the topical formulations on the pelvic lymph nodes and (c) to obtain preliminary information on the efficacy of the topical formulations applied to cervical cancer.

The population of the study will be a minimum of 15 and a maximum of 24 eligible subjects across two sites with cervical cancer confirmed by histology.

The primary endpoint will be safety and tolerability, as assessed by adverse events, changes in vital signs, laboratory results, and physical examination. The secondary endpoints will be (a) PK parameters; (b) change in presence of cancer as determined by basement membrane evaluation seen on biopsy; (c) presence or absence of tumor cells in pelvic lymph nodes at the time of hysterectomy; (d) presence or absence of paclitaxel in pelvic lymph nodes at the time of hysterectomy and (d) proportion of subjects defined as Complete Responders (CR) and Partial Responders (PR) to the formulations at Day 28 (clinical response is defined by presence or absence of cervical cancer at the time of hysterectomy).

Example 13—Dermal Toxicity Study

A dermal toxicity study was conducted using the formulations shown in Table 22.

TABLE 22

| Component (% w/w) | Formula No. | | | |
|---|---|---|---|---|
| | F18 (0.0%) Placebo | F19 (0.3%) | F20 (1%) | F21 (3%) |
| Paclitaxel Nanoparticles | 0.0 | 0.3 | 1.0 | 3.0 |
| Mineral Oil USP | 5.0 | 5.0 | 5.0 | 5.0 |
| ST-Cyclomethicone 5 NF (Dow Corning) | 13.0 | 13.0 | 13.0 | 13.0 |
| Paraffin Wax NF | 5.0 | 5.0 | 5.0 | 5.0 |
| White Petrolatum USP (Spectrum) | qs ad 100 | qs ad 100 | qs ad 100 | qs ad 100 |

The GLP-compliant study was conducted in Gottingen minipigs to characterize the toxicity of the formulations applied topically to 10% body surface area daily for 28 days. The 4 formulations shown in Table 22 were applied at the maximal feasible volume of 2 mL/kg, correlating to dose concentrations of 0.0, 0.3, 1.0, and 3%, which translate to dose levels of 0, 4.9, 16.5, and 49.9 mg/kg/day respectively. Reversibility of findings was also evaluated following a 2-week recovery period. Parameters evaluated included clinical observations, mortality and moribundity checks, dermal scoring, body weight, food consumption, eye examinations, test site photographs, electrocardiology, clinical pathology, bioanalysis and toxicokinetic evaluation, organ weights, macroscopic pathology and histopathology. There were no formulation-related effects on survival, clinical signs, dermal irritation, body weights, body weight gains, food consumption, ophthalmic findings, or cardiology parameters. Minimal dermal irritation was observed in all groups during the dosing phase and was considered vehicle or procedurally related as the frequency and severity of the findings were comparable between the placebo controls and active formulation-treated groups. Thus, the presence of the paclitaxel nanoparticles in the formulations had a negligible effect on dermal irritation.

The invention claimed is:

1. A method of treating cervical intraepithelial neoplasia (CIN) or cervical cancer in a subject in need of treatment, the method comprising topically administering to an affected area of the subject a hydrophobic composition comprising a plurality of taxane nanoparticles, thereby treating the CIN or the cervical cancer, wherein the taxane nanoparticles are uncoated (neat) individual particles of paclitaxel or docetaxel that are not encapsulated in, bound to, or conjugated to any substance.

2. The method of claim 1, wherein the taxane nanoparticles have a mean particle size (number) from 0.1 microns to 1.5 microns.

3. The method of claim 1, wherein the composition comprises 0.1% w/w to 5% w/w of the plurality of the taxane nanoparticles.

4. The method of claim 1, wherein the taxane nanoparticles are suspended within the composition.

5. The method of claim 1, wherein the paclitaxel nanoparticles or docetaxel nanoparticles have a specific surface area (SSA) of at least 18 $m^2/g$.

6. The method of claim 1, wherein the taxane nanoparticles are paclitaxel nanoparticles.

7. The method of claim 6, wherein the paclitaxel nanoparticles have a specific surface area (SSA) of 18 $m^2/g$ to 50 $m^2/g$.

8. The method of claim 6, wherein the paclitaxel nanoparticles contain not less than 90% paclitaxel.

9. The method of claim 1, wherein the composition is an anhydrous composition.

10. The method of claim 1, wherein the hydrophobic composition comprises a hydrophobic carrier.

11. The method of claim 10, wherein the hydrophobic carrier comprises petrolatum, mineral oil, or paraffin was, or mixtures thereof.

12. The method of claim 10, wherein the hydrophobic carrier is greater than 50% w/w of the composition.

13. The method of claim 1, wherein the hydrophobic composition comprises one or more volatile silicone fluids.

14. The method of claim 13, wherein the concentration of the one or more volatile silicone fluids is from 5 to 24% w/w of the composition.

15. The method of claim 13, wherein the one or more volatile silicone fluids is cyclomethicone.

16. The method of claim 1, wherein the subject has CIN, and wherein the CIN is treated.

17. The method of claim 1, wherein the subject has cervical cancer, and wherein the cervical cancer is treated.

18. A method of enhancing penetration of taxane nanoparticles into a cervical intraepithelial neoplasia (CIN) or cervical cancer of a subject, the method comprising topically applying to the affected area a hydrophobic composition comprising a continuous hydrophobic carrier, one or more volatile silicone fluids, and a plurality of taxane nanoparticles, wherein the taxane nanoparticles are uncoated (neat) individual particles of paclitaxel or docetaxel that are not encapsulated in, bound to, or conjugated to any substance.

* * * * *

UNITED STATES PATENT AND TRADEMARK OFFICE
CERTIFICATE OF CORRECTION

| | | |
|---|---|---|
| PATENT NO. | : 11,497,726 B2 | Page 1 of 1 |
| APPLICATION NO. | : 16/978820 | |
| DATED | : November 15, 2022 | |
| INVENTOR(S) | : Gere Dizerega | |

It is certified that error appears in the above-identified patent and that said Letters Patent is hereby corrected as shown below:

On the Title Page

Item (73) Replace "DFB SORIA, LL." with -- DFB SORIA, LLC --

Signed and Sealed this
Fourth Day of April, 2023

Katherine Kelly Vidal
*Director of the United States Patent and Trademark Office*